(12) United States Patent
Von Hirschheydt et al.

(10) Patent No.: US 11,945,839 B2
(45) Date of Patent: Apr. 2, 2024

(54) DEPLETION OF LIGHT CHAIN MISPAIRED ANTIBODY VARIANTS BY HYDROPHOBIC INTERACTION CHROMATOGRAPHY

(71) Applicant: Hoffmann-La Roche Inc., Little Falls, NJ (US)

(72) Inventors: Thomas Von Hirschheydt, Penzberg (DE); Petra Rueger, Penzberg (DE); Birgit Weydanz, Penzberg (DE); Hubert Hertenberger, Weilheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 141 days.

(21) Appl. No.: 16/955,776

(22) PCT Filed: Dec. 20, 2018

(86) PCT No.: PCT/EP2018/086059
§ 371 (c)(1),
(2) Date: Jun. 19, 2020

(87) PCT Pub. No.: WO2019/122054
PCT Pub. Date: Jun. 27, 2019

(65) Prior Publication Data
US 2020/0369719 A1 Nov. 26, 2020

(30) Foreign Application Priority Data
Dec. 22, 2017 (EP) .................... 17210376

(51) Int. Cl.
*C07K 1/20* (2006.01)
*C07K 16/28* (2006.01)
*C07K 16/40* (2006.01)

(52) U.S. Cl.
CPC ............ *C07K 1/20* (2013.01); *C07K 16/2878* (2013.01); *C07K 16/40* (2013.01); *C07K 2317/31* (2013.01); *C07K 2317/55* (2013.01); *C07K 2317/66* (2013.01)

(58) Field of Classification Search
None
See application file for complete search history.

(56) References Cited

U.S. PATENT DOCUMENTS

| | | | | |
|---|---|---|---|---|
| 9,249,182 | B2 * | 2/2016 | Herigstad ................ | C07K 1/36 |
| 2014/0017244 | A1 * | 1/2014 | Duerr ...................... | A61P 27/06 |
| | | | | 435/69.6 |
| 2016/0159894 | A1 * | 6/2016 | Hartmann ............ | C07K 16/468 |
| | | | | 530/387.3 |
| 2016/0326241 | A1 * | 11/2016 | Auer ..................... | C07K 16/244 |
| 2016/0326253 | A1 * | 11/2016 | Ueda ........................ | C07K 1/18 |
| 2017/0037121 | A1 * | 2/2017 | Schlothauer ............ | A61P 43/00 |
| 2017/0247441 | A1 * | 8/2017 | Dengl ................ | A61K 39/3955 |

FOREIGN PATENT DOCUMENTS

| | | |
|---|---|---|
| EP | 0821695 A1 | 2/1998 |
| WO | 2013093720 A2 | 6/2013 |
| WO | 2015/024896 A1 | 2/2015 |
| WO | 2016/075035 A1 | 5/2016 |
| WO | 2017/218977 A2 | 12/2017 |

OTHER PUBLICATIONS

CaptoTM Phenyl ImpRes and Capto Butyl ImpRes, GE Healthcare Life Sciences, p. 1-4. (Year: 2013).*
Phenyl Sepharose High Performance Butyl Sepharose High Performance GE healthcare Bio-Sciences AB, p. 1-8 (Year: 2014).*
Ghose et al., mAbs 5(5): 795-800 (Year: 2013).*
International Search Report and Written Opinion of the International Searching Authority in International Application No. PCT/EP2018/086059, dated Mar. 13, 2019.
Aran F. Labrijn et al., "Controlled Fab-arm Exchange for the Generation of Stable Bispecific IgG1", Nature Protocols, 2014, pp. 2450-2463, vol. 9, No. 10.
Hui-Min Zhang, et al., "Structural and Functional Characterization of a Hole-Hole Homodimer Variant in a 'Knob-Into-Knob' Bispecific Antibody", Analytical Chemistry, 2017, pp. 13494-13501, vol. 89, No. 24.
Ulrich Brinkmann et al., "The Making of Bispecific Antibodies", MABS, 2017, pp. 182-212, vol. 9, No. 2.
Yi Feng Lee et al., "Modeling of Bispecific Antibody Elution in Mixed-Mode Cation-Exchange Chromatography", Journal of Separation Science, 2017, pp. 3632-3645, vol. 40, No. 18.
Oliver Manzke et al., "Single-Step Purification of Bispecific Monoclonal Antibodies for Immunotherapeutic Use By Hydrophobic Interaction Chromatography", Journal of Immunological Methods, 1997, pp. 65-73, vol. 208, No. 1.

* cited by examiner

*Primary Examiner* — Phuong Huynh
(74) *Attorney, Agent, or Firm* — Grimes & Yvon LLP

(57) ABSTRACT

The present invention relates to methods for separating multispecific CrossMab antibodies from light chain mispaired variants thereof in a solution comprising CrossMab bispecific antibodies and mispaired antibody variants thereof by hydrophobic interaction chromatography.

17 Claims, 19 Drawing Sheets

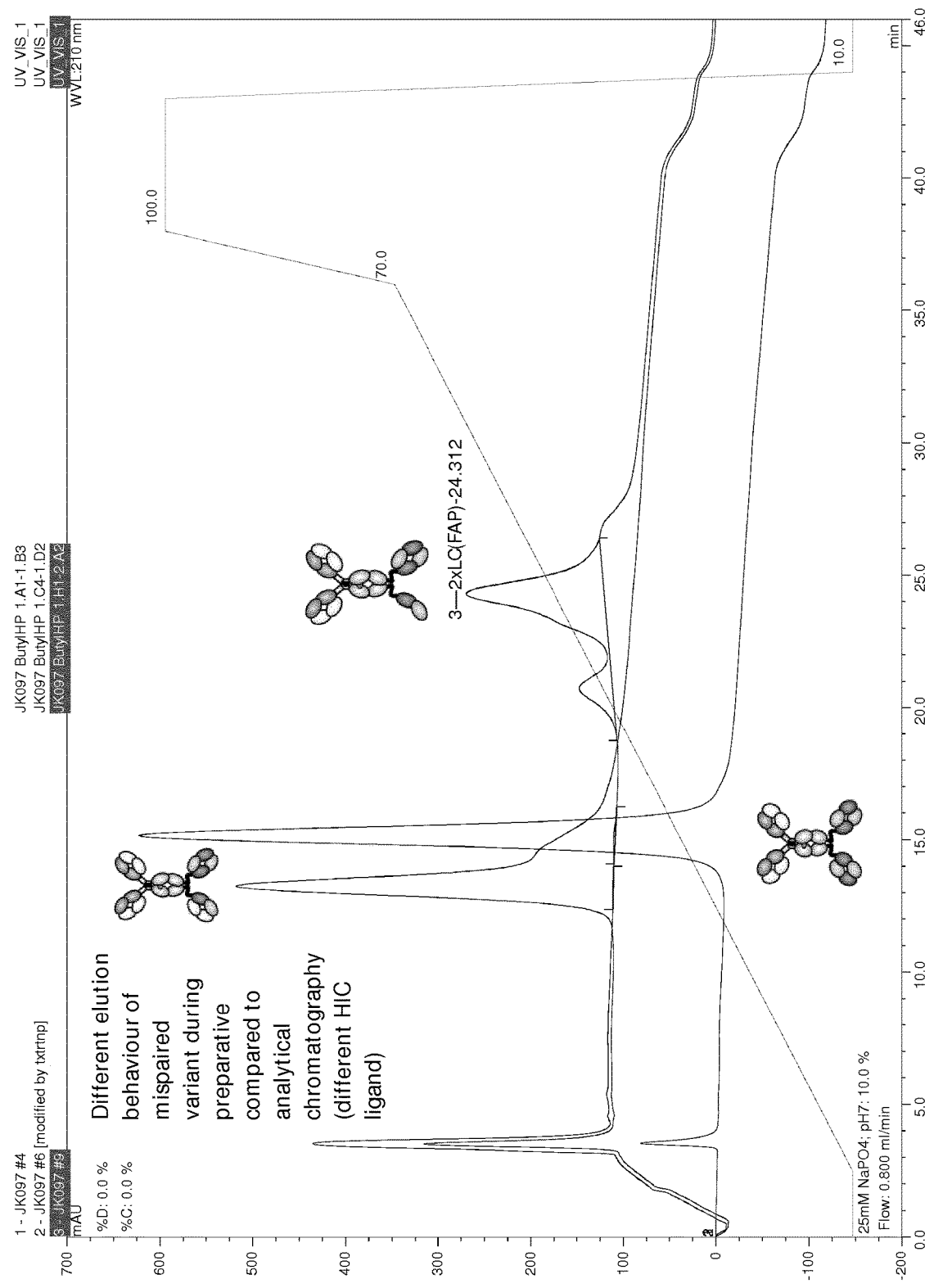

Toyopearl PPG 600M

Butyl Sepharose HP

DEPLETION OF LIGHT CHAIN MISPAIRED ANTIBODY VARIANTS BY HYDROPHOBIC INTERACTION CHROMATOGRAPHY

CROSS-REFERENCE TO RELATED APPLICATIONS

This application is National Stage of International Application No. PCT/EP2018/086059, filed on Dec. 20, 2018, which claims the benefit of priority to EP Application No. 17210376.4, filed on Dec. 22, 2017, both of which are hereby incorporated by reference in their entireties for all purposes.

FIELD OF THE INVENTION

The present invention concerns the use of hydrophobic interaction chromatography for separating a multispecific CrossMab antibody from light chain mispaired variants thereof in a solution comprising CrossMab multispecific antibodies and mispaired antibody variants thereof. Light chain mispaired variants include variants of the antibody with one or more light chains paired to the wrong heavy chain of the multispecific CrossMab antibody. Thus, the methods of the present invention comprise the separation of a multispecific CrossMab antibody from one or more mispaired variants thereof. The hydrophobic interaction chromatography method of the invention may be used alone or may be further combined with standard purification as known in the art to achieve any level of purity of multispecific CrossMab antibody necessary, e.g. for a pharmaceutical composition comprising said multispecific CrossMab antibody obtained by said methods for use in therapeutic and/or diagnostic applications.

BACKGROUND OF THE INVENTION

Engineered proteins, such as multispecific antibodies capable of binding two or more antigens can be generated using cell fusion, chemical conjugation, or recombinant DNA techniques. A wide variety of recombinant multispecific antibody formats have been developed, e.g. tetravalent bispecific antibodies by fusion of, e.g. an IgG antibody format and single chain domains (see e.g. Coloma, M. J., et. al., Nature Biotech. 15 (1997) 159-163; WO 2001/077342; and Morrison, S. L., Nature Biotech. 25 (2007) 1233-1234).

The therapeutic potential of bispecific antibodies has long been recognized. Bispecific antibodies offer an IgG like platform that is able to bind two antigens or two epitopes simultaneously. Thus, bispecific antibodies offer a potential tool to modulate the interaction of at least two molecules and/or the interaction of at least two systems comprising the molecules. Such modulation may be, for example, modulation of the interaction of two cells where the recognized antigen, antigens and/or epitopes are expressed on the surface of the cells. Examples of the therapeutic use of bispecific antibodies include, for example, the modulation of cell signaling (e.g., by promoting or interfering with the interaction of desired surface receptors or ligands) and cancer therapies (e.g., aiding in the targeting of immune cells to cancer cells). For example, WO 2014/161845 provides bispecific antibodies comprising a first antigen binding site specific for Death Receptor 5 (DR5) and a second antigen binding site specific for Fibroblast Activation Protein (FAP) for use in cancer therapy.

Despite the interest in the therapeutic use of bispecific antibodies, their commercial production has proven to be problematic. Early approaches focused on bispecific antibodies that are very similar to natural antibodies and that have been produced using the quadroma technology (see Milstein, C. and Cuello, A. C., Nature 305 (1983) 537-540) which is based on the somatic fusion of two different hybridoma cell lines expressing murine monoclonal antibodies with the desired specificities of the bispecific antibody. Using quadroma expressed antibody molecules, it was immediately apparent that the expressed molecules contained varying combinations of the two parental heavy and two parental light chains. The simultaneous expression of all four parental chains leads to a mixture of 10 different variants of almost identical molecules, wherein only 1 of the 10 (i.e., only a minor fraction of all molecules expressed) contained the properly paired heavy and light chains necessary to exhibit the desired bispecific activity (see, e.g., Suresh et al, Methods Enzymol. 121(1986), 210-228). Accordingly, attention turned to alternate bispecific antibody-based constructs in an attempt to eliminate the production problems, e.g., single-chain fusions of antibody variable domains. However, many of these formats differ significantly from the archetypical antibody structure and were found to exhibit therapeutic disadvantages such as poor pharmacokinetic properties and/or loss of effector activity (e.g., due to absence of Fc domains). Further, many constructs also exhibited a tendency to aggregate and an increased potential for immunogenicity due to the presence of non-human or artificial domains such as linker regions. In addition, the production of a standard antibody relies on the dimerization of identical heavy-chain/light-chain subunits. In contrast, the production of a bispecific antibody requires the dimerization of two different heavy-chain/light-chain subunits, each comprising a different heavy chain as well as a different light chain. Thus, bispecific antibody production requires the proper interaction of up to four peptide chains. Accordingly, chain mispairings (e.g., homo-dimerization of identical heavy chain peptides or improper heavy-chain/light-chain associations) are often observed.

Thus, one drawback in production of multispecific antibodies is formation of various undesired side products apart from the desired functional molecule. Mispairing includes the pairing of wrong heavy chains with each other as well as pairing of a light chain with a wrong heavy chain counterpart or undesired pairing of light chains.

In view of these drawbacks and the limitation of alternate bispecific formats, interest in bispecific antibodies having the archetypical antibody architecture remains (in particular, IgG-like architecture). Principally, two problems arise during the production of a desired bispecific antibody having IgG-like architecture. Because such a molecule requires the proper association of 2 different heavy chains and 2 different light chains, it is necessary (1) to induce hetero-dimerization of the two different heavy chains as a preferred reaction over homo-dimerization, and (2) to optimize the discrimination among the possible light-chain/heavy-chain combinations interactions such that the expressed molecule contains only the desired light-chain/heavy-chain interactions.

In this regard, strategies based on forcing the heterodimerization of two heavy chains have been explored. A first approach coined 'knobs into holes' (sometimes also referred to as 'knob in hole', 'knob-hole' or 'KiH' or the like) aims at forcing the pairing of two different IgG heavy chains by introducing mutations into the CH3 domains to modify the contact interface (Ridgway J B et al., Protein Eng 1996; 9: 617-621). For example, WO 98/50431 uses different heavy chains which are heterodimerized via the so-called 'knobs-into-holes' technology (Ridgway, J. B., Protein Eng. 9

(1996) 617-621; and WO 96/027011). Using this technology, amino acids with large side chains were introduced on one chain, to create a 'knob'. Conversely, bulky amino acids were replaced by amino acids with short side chains to create a 'hole' into the other CH3 domain. By co-expressing these two heavy chains, high yields of antibodies with heterodimerized ('knob-hole') heavy chains was observed. However, some homodimer formation ('hole-hole' or 'knob-knob') was also observed. Therefore, downstream purification procedures capable of removing the homodimers from the heterodimers are still required.

The percentage of heterodimerized heavy chains could be further increased by remodeling the interaction surfaces of the two CH3 domains using a phage display approach and introducing a disulfide bridge between both CH3 domains in order to stabilize the heterodimers (Merchant A. M, et al., Nature Biotech 16 (1998) 677-681; Atwell, S., et al., J. Mol. Biol. 270 (1997) 26-35). New approaches using the principle of the knobs-into-holes technology are described e.g. in EP 1870459A1. One important constraint of this strategy is that the light chains of the two parent antibodies have to be 100% identical to prevent mispairing and formation of inactive molecules. The development of common light chains fitting to de novo generated antibodies is still challenging. Another potential issue of the KiH approach is that the mutated domains are not fully human and can lead to immunogenicity and might also affect the domain stability and aggregation propensity of the molecule. As KiH strategies allow for the forced paring of the heavy chains, the different light chains can randomly pair with any of the two heavy chains and lead to the generation of different antibodies that need to be purified from one another.

Thus, this technique is not appropriate for easily developing recombinant, bispecific antibodies against two antigens starting from two different antibodies against the first and the second antigen, as either the heavy chains of these antibodies and/or the identical light chains have to be optimized. Consequently, this technique is also not appropriate as a basis for easily developing recombinant, tri- or tetraspecific antibodies against three or four antigens starting from two antibodies against the first and the second antigen, as either the heavy chains of these antibodies and/or the identical light chains have to be optimized first and then further antigen binding peptides against the third and fourth antigen have to be added.

One approach of circumventing the problem of mispaired variants of bispecific antibodies aims at forcing the pairing of a light chain polypeptide with its correct heavy chain counterpart. This approach, known as the "CrossMab technology" is based on a domain crossover between heavy and light chains thereby creating different domain arrangements for heavy chains and light chains of different specificity. WO 2009/080251, WO 2009/080252, WO 2009/080253, WO 2009/080254 and Schaefer, W. et al, PNAS, 108 (2011) 11187-1191 relate to bivalent, bispecific IgG antibodies with a domain crossover. WO 2010/145792 relates to tetravalent antigen binding proteins with a domain crossover. The multispecific antibodies with a VH/VL replacement/exchange in one binding site to prevent light chain mispairing (CrossMab$^{VH-VL}$), which are described in WO 2009/080252 (see also Schaefer, W. et al, PNAS, 108 (2011) 11187-1191), clearly reduce the production of mispaired variants caused by the mismatch of a light chain against a first antigen with the wrong heavy chain against the second antigen (compared to approaches without such domain exchange).

With respect to the separation of incomplete assembled antibodies, most commercial antibody production and purification schemes are used in conjunction with affinity chromatography for commercial antibody purification standard chromatography methods that separate the protein of interest from undesired byproducts/impurities based on differences in size, charge (e.g., isoelectric point or "IEP"), solubility, and/or degree of hydrophobicity are used. For example, WO 2015/024896 provides a method comprising the use of hydroxyapatite chromatography of separating a bispecific antibody from a solution that also comprises one or more byproducts specific to the production of bispecific antibodies (bispecific antibody specific byproducts, "BASB") including fragments of the bispecific antibody and heavier molecular weight variants of the antibody. However, as these byproducts have a higher or lower molecular weight than the bispecific antibody of interest, light chain mispaired antibodies have not been addressed by these prior art techniques which are based on separation by molecular weight.

The present inventors have found that despite recent advantages in the production of multispecific antibodies and separation of incomplete antibodies from the multispecific antibodies, the separation of multispecific CrossMab antibodies from light chain mispaired variants thereof represents unique challenges. Such incomplete assembly commonly include but are not limited to ½ antibodies (comprising a single heavy-chain/light-chain pair) and ¾ antibodies (comprising a complete antibody lacking a single light chain). Both byproducts (light chain mispaired and incomplete antibodies) may exhibit particularly disadvantageous activity should they remain in the final purified product. For example, the functionality of the bispecific molecule may depend on a single molecule exhibiting binding activity to two different antigens. Where a molecule exhibits binding activity to only one target antigen (e.g., as in a ½ or ¾ antibody or light chain mispaired antibody as described above), its binding to this target antigen would block the binding of a fully functional bispecific antibody, potentially antagonizing the desired activity of the bispecific molecule. At the very least, the monospecific byproducts of bispecific antibody production would likely reduce efficacy of the final bispecific formulation if not separated. Additionally, many of the byproducts as described herein, having exposed regions that normally promote peptide-peptide interaction, may exhibit a tendency to immunogenicity and aggregation.

Hence, there is still a need for separating light chain mispaired antibodies from desired antibodies since the preparation is not completely free of such side products which is based on the interaction of the wrong light chain with the domain-exchanged heavy chain.

SUMMARY OF THE INVENTION

The present invention thus relates to methods for separating so-called CrossMab antibodies and light chain mispaired variants thereof in a solution comprising CrossMab multispecific (particularly bispecific) antibodies and mispaired antibody variants thereof by hydrophobic interaction chromatography (HIC). The present inventors have surprisingly found that particular HIC media are able to separate the unwanted mispaired species from the desired correctly-paired CrossMab antibody.

Hence, the present invention relates to a method for separating a multispecific CrossMab antibody from a mispaired variant thereof by using a hydrophobic interaction chromatography (HIC) medium, the medium comprising a matrix of particles substituted with ligands, (i) wherein said particles have an average size of 50 μm or less, preferably 45 μm or less, more preferably between 34 μm and 40 μm in diameter and said ligands are butyl groups;

(ii) wherein said particles have an average size of from 35 μm to 60 μm, preferably between 35 μm and 50 μm, more preferably between 35 μm and 45 μm, most preferably 40 μm in diameter and said ligands are phenyl groups; or (iii) wherein said particles have an average size of from 35 μm to 100 μm, preferably between 60 μm and 70 μm, most preferably 65 μm in diameter and said ligands are polypropylene glycol groups.

More in particular, the present invention pertains to a method for separating a multispecific CrossMab antibody from a mispaired variant thereof, comprising subjecting a solution comprising said CrossMab antibody and said mispaired variant thereof to a hydrophobic interaction chromatography (HIC) step, thereby obtaining said CrossMab antibody depleted of said mispaired variant thereof, wherein the chromatographic medium used in said HIC step comprises a matrix of particles substituted with ligands, (i) wherein said particles have an average size of 50 μm or less, preferably 45 μm or less, more preferably between 34 μm and 40 μm in diameter and said ligands are butyl groups;

(ii) wherein said particles have an average size of from 35 μm to 60 μm, preferably between 35 μm and 50 μm, more preferably between 35 μm and 45 μm, most preferably 40 μm in diameter and said ligands are phenyl groups; or (iii) wherein said particles have an average size of from 35 μm to 100 μm, preferably between 60 μm and 70 μm, most preferably 65 μm in diameter and said ligands are polypropylene glycol (PPG) groups.

The present invention also relates to the use of a hydrophobic interaction chromatography (HIC) medium in a method for separating a multispecific CrossMab antibody from a mispaired variant thereof according to the invention.

The HIC medium may in some aspects be selected from the group consisting of Butyl Sepharose HP, Capto Butyl ImpRes, Capto Phenyl ImpRes (all available from GE Healthcare) and PPG-600M (available as "Toyopearl 600M" from Tosoh). In a particular aspect of the present invention, the HIC medium may be selected from the group consisting of Butyl Sepharose HP, Capto Butyl ImpRes and Capto Phenyl ImpRes or it may have the same selectivity as Butyl Sepharose HP, Capto Butyl ImpRes, Capto Phenyl ImpRes or (Toyopearl) PPG-600M.

In the context of the present invention, said multispecific CrossMab antibody may be a multispecific antibody comprising (a) a first antigen binding region specifically binding to a first antigen, wherein the first antigen binding region comprises the light chain and heavy chain of an antibody specifically binding to a first antigen, and (b) a second antigen binding region specifically binding to a second antigen, wherein in the second antigen binding region comprises the light chain and heavy chain of an antibody specifically binding to a second antigen, wherein in the second antigen binding region (i) the constant domains CL and CH1 are replaced by each other, and/or (ii) the constant domains VL and VH are replaced by each other.

The mispaired variant of the CrossMab antibody herein in particular comprises at least one light chain of the multispecific CrossMab antibody thereof that is replaced by another light chain of said multispecific CrossMab antibody, i.e. at least one of the light chains of said variant does not pair with its complementary heavy chain.

It may particularly be a bispecific bivalent antibody, a bispecific trivalent or a bispecific, tetravalent antibody. For example, it may be bivalent for the first antigen and bivalent for the second antigen.

In a particular aspect of the present invention the multispecific CrossMab is a bispecific antibody comprising at least one antigen binding region specific for death receptor 5 (DR5), and at least one antigen binding region specific for Fibroblast Activation Protein (FAP), wherein the antigen binding region specific for DR5 comprises a variable heavy chain comprising the amino acid sequence of SEQ ID NO.: 7 of WO 2014/161845 A1 and a variable light chain comprising the amino acid sequence of SEQ ID NO.: 8 of WO 2014/161845 A1; and the antigen binding region specific for FAP comprises a heavy chain variable region comprising the amino acid sequence of SEQ ID NO.: 15 of WO 2014/161845 A1 and a light chain variable region comprising the amino acid sequence of SEQ ID NO.: 16 of WO 2014/161845 A1. In this context, said antibody may comprise two of each of said antigen binding regions specific for DR5 and antigen binding regions specific antigen binding region specific for FAP.

Using the method of the present invention, the multispecific CrossMab antibody and said mispaired variant thereof may be separately eluted from the HIC medium, thereby separating the multispecific CrossMab antibody from the mispaired variant thereof in the solution based on hydrophobicity.

The present invention also pertains to the use of a hydrophobic interaction chromatography (HIC) medium for separating a multispecific CrossMab antibody from a mispaired variant thereof, wherein the medium comprises a matrix of particles substituted with ligands, (i) wherein said particles have an average size of 50 μm or less, preferably 45 μm or less, more preferably between 34 μm and 40 μm in diameter and said ligands are butyl groups;

(i) wherein said particles have an average size of from 35 μm to 60 μm, preferably between 35 μm and 50 μm, more preferably between 35 μm and 45 μm, most preferably 40 μm in diameter and said ligands are phenyl groups; or (iii) wherein said particles have an average size of from 35 μm to 100 μm, preferably between 60 μm and 70 μm, most preferably 65 μm in diameter and said ligands are polypropylene glycol groups.

Preferably, the present invention also pertains to the use of a hydrophobic interaction chromatography (HIC) medium for separating a multispecific CrossMab antibody from a mispaired variant thereof, wherein the medium comprises a matrix of particles substituted with ligands, (i) wherein said particles have an average size of 50 μm or less, preferably 45 μm or less, more preferably between 34 μm and 40 μm in diameter and said ligands are butyl groups;

(ii) wherein said particles have an average size of from 35 μm to 60 μm, preferably between 35 μm and 50 μm, more preferably between 35 µm and 45 µm, most preferably 40 µm in diameter and said ligands are phenyl groups.

BRIEF DESCRIPTION OF THE DRAWINGS

FIG. 5: Analytical HI-HPLC showing a different elution behavior of $LC_{DR5}$ mispaired antibody variants during preparative compared to analytical chromatography. The $LC_{DR5}$ mispaired antibody variants elute before the intact product of the anti-DR5/anti-FAP antibodies.

DETAILED DESCRIPTION OF THE INVENTION

CrossMab Antibodies

The present invention pertains to the purification of so-called "CrossMab" antibodies from mispaired light chain variants thereof using particular HIC media. CrossMab antibodies are multispecific (i.e. at least bispecific) antibodies in which correct association of the light chains and their cognate heavy chains is achieved by exchange of heavy-chain and light-chain domains within the antigen binding region (Fab) of at least one Fab of the multispecific antibody wherein no such exchange is performed in at least one other Fab region so that mispairing is avoided in these at least two Fab regions. In the case of bispecific CrossMab antibodies, correct association of the light chains and their cognate heavy chains can, thus, be achieved by exchange of heavy-chain and light-chain domains within the Fab region of one half of the bispecific antibody while the other half remains unchained or has a different exchange. The terms "Fab region" and "Fab fragment" (or just "Fab" as the case may be) mean the same and are used interchangeably herein.

Therefore, the term "CrossMab antibody" refers to a multispecific antibody (or a suitable multispecific fragment thereof), wherein either the variable regions and/or the constant regions of the heavy and light chain are exchanged. For example, the CrossMab antibody can be any of the CrossMab antibodies described or claimed in WO 2009/080252, WO 2009/080253, WO 2009/080251, WO 2009/080254, WO 2010/136172, WO 2010/145792 and WO 2013/026831.

The term "CrossMab" antibody is generally recognized in the art; e.g. see Brinkmann, U. & Kontermann, R., MAbs 9(2):182-212 (2017); Kontermann, R. & Brinkmann, U., Drug Discovery Today 20(7):838-846 (2015); Schaefer, W. et al, PNAS, 108 (2011) 11187-1191; Klein, C. et al., MAbs 8(6):1010-1020 (2016); Klein, C. et al., MAbs 4(6):653-663 (2012).

Figure 1:
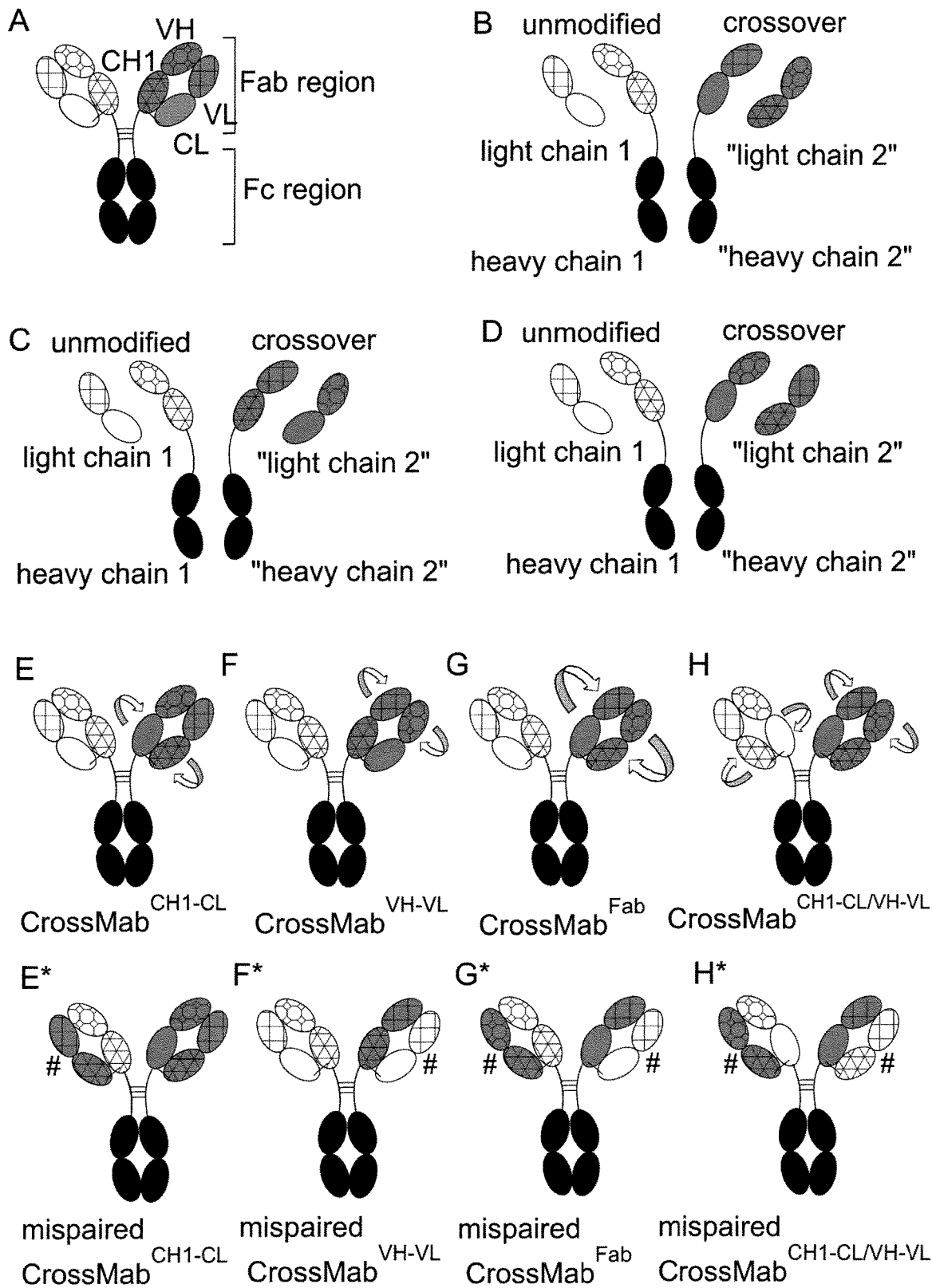
FIG. 1 A-H. Schematic representation of a bivalent, bispecific antibody (A) and crossover of the complete Fab region (A), the CH1-CL domain and the VH-VL domain resulting in the generation of a CrossMab bispecific antibody. Overview of bivalent, bispecific antibodies enabled by CrossMab technology (E-H). The drawings represent only examples, since in many cases crossed and uncrossed Fab regions can be assembled in various ways. Side products resulting from Bence-Jones interaction of the wrong light chain with the heavy chain or the domain-exchanged heavy chain (E*-H*) are shown. Fc region is colored in black, the first Fab region is colored in white and the second Fab region is colored in gray, wherein the CL domain is colored uniformly, the VL domain is colored with a squares pattern, the CH1 domain is colored in a triangle pattern and the VH domain is colored in an octagon pattern.

In the case of a bispecific bivalent CrossMab, three different chain compositions of a crossover antibody are possible: With respect to the first composition, the variable domains of the heavy and light chain of the antibody are exchanged, i.e. the antibody comprises in one Fab region a peptide chain composed of the light chain variable domain (VL) and the heavy chain constant domain (CH1), and a peptide chain composed of the heavy chain variable domain (VH) and the light chain constant domain (CL). This antibody is also referred to as CrossMab$^{VL-VH}$ (FIG. 1 D). With respect to the second composition, when the constant domains of the heavy and light chain of the antibody in one Fab region are exchanged, the antibody comprises in this Fab region a peptide chain composed of the heavy chain variable domain (VH) and the light chain constant domain (CL), and a peptide chain composed of the light chain variable domain (VL) and the heavy chain constant domain (CH1). This antibody is also referred to as CrossMab$^{CL-CH1}$ (FIG. 1 C). With respect to the third composition, the heavy chain of the antibody comprising the constant and the variable domains and the light chain of the antibody comprising the constant and the variable domain are exchanged, i.e. the antibody comprises a peptide chain composed of the light chain variable domain (VH) and the heavy chain constant domain (VL), and a peptide chain composed of the heavy chain variable domain (VL) and the light chain constant domain (CH1). This antibody is also referred to as CrossFab$^{Fab-Fab}$ (FIG. 1 B).

CrossMab antibodies are monoclonal antibodies. The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. Preferably, the monoclonal antibodies to be used in accordance with the present invention may be made by recombinant DNA methods.

CrossMab antibodies herein also encompass functional fragments thereof, i.e. fragments that retain their multispecificity. A "fragment" of a CrossMab antibody therefore refers to a molecule other than an intact CrossMab antibody that comprises a portion of an intact antibody that binds the antigens to which the intact antibody binds. Examples of CrossMab antibody fragments include but are not limited to F(ab')$_2$ multispecific CrossMab antibodies.

"Fab" fragments containing each the heavy- and light-chain variable domains and also the constant domain of the light chain and the first constant domain (CH1) of the heavy chain. As discussed herein above, the terms "Fab fragment", "Fab region" or simply "Fab" are used interchangeably, and are used herein to describe the antigen-binding portion of an antibody. The Fab fragment is heterodimeric, composed of two polypeptides, a light chain having a variable (VL) and constant (CL) domain, and a heavy chain having a variable (VH) and a first constant domain (CH1) and may also include the upper hinge region, particularly if the Fab is of a IgG1 subclass. The polypeptide chains are not linked to one another by a peptide bond but associate with one another by non-covalent interactions and by a disulfide bond if the upper hinge region of the heavy chain is present. As used herein, the term "Fab heavy chain" denotes a polypeptide composed of a VH domain and a CH1 domain but does not contain a CH2 domain or a CH3 domain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group.

The term "mispaired variants thereof" refers to a multispecific CrossMab antibody that is paired with at least one wrong light chain with the domain-exchanged heavy chain as described above with respect to the CrossMab antibody. In other words, at least one of the light chains of said variant does not pair with its complementary heavy chain, e.g. an "unmodified" light chain comprising CL and VL mispairs with a "modified" heavy chain having CH1 and VL or a "modified" light chain comprising CH1 and VL mispairs with an "unmodified" heavy chain having CH1 and VH etc. In this context "complementary" domains are the normally pairing heavy and light chain domains, i.e. CH1 normally pairs with CL and VH normally pairs with VL. Vice versa, "non-complementary" domains are the wrong pairing heavy and light chain domains. For example, the wrong light chain of the pair of heavy and light chain domains may refer to a light chain, wherein the variable and/or constant domains of the light chain are exchanged, whereas in the heavy chain the variable and/or constant domains of the heavy chain are not exchanged. As another example, the wrong pairing of heavy and light chain domains may refer to a situation in which the variable and/or constant domains of the light chain are not exchanged, and the variable and/or constant domains of the heavy chain are exchanged. As used herein, the term "non-complementary" does not refer to incompletely assembled antibodies, such as but not limited to antibodies in which one light chain or a fragment thereof is missing.

In one embodiment, the mispaired variant thereof is a variant of said multispecific CrossMab antibody, wherein one or more light chains are paired with a non-complementary heavy chain. The CrossMab antibody herein is a multispecific antibody comprising two or more specific antigen binding sites. The specific antigen binging sites may be on the same or different antigens. Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168).

As used herein, the term in "antigen-binding site" of an antibody refers to the part of the antibody that specifically binds to an antigenic determinant. More particularly, the term "antigen-binding site" refers the part of an antibody that comprises the area which specifically binds to and is complementary to part or all of an antigen. Where an antigen is large, an antigen binding molecule may only bind to a particular part of the antigen, which part is termed an epitope. An antigen-binding site may be provided by, for example, one or more variable domains (also called variable regions).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Thus, an epitope is a region of an antigen that is bound by an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. In certain embodiments, an antibody is said to specifically bind an antigen when it preferentially recognizes its target antigen in a complex mixture of proteins and/or macromolecules. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)).

An example of a multispecific antibody is a bispecific, trispecific or tetraspecific antibody which has two specific antigen hinging sites, three specific antigen binging sites or four specific antigen binding sites.

A bispecific CrossMab antibody that is monovalent for each antigen (or different epitope on the same antigen) is referred to as a "1+1 format". Similarly, a tetraspecific antibody that is bivalent for each antigen (or different epitope on the same antigen) is referred to as a "2+2 format". A trivalent bispecific antibody is referred to as a "2+1 format" and so on.

In a particular aspect, the invention is directed to the purification of bispecific CrossMab antibodies, which comprise two different heavy chains (each derived from a different antibody) and two different light chains (each derived from a different antibody), and/or heavy and light chains each comprising fragments from two or more different antibodies. Thus, the bispecific antibody herein may comprise heavy and/or light chains from de-immunized, murine, chimeric, humanized and human antibodies, as well as combinations heavy and/or light chains from de-immunized, murine, chimeric, humanized, human antibodies and fragments thereof (e.g., variable and/or constant domains thereof). Bispecific CrossMab antibodies herein denotes antibodies that comprise two binding sites each of which bind to different epitopes of the same antigen or a different antigen.

Of particular interest herein are bispecific CrossMab antibodies binding death receptor 5 (DR5) and Human Fibroblast Activation Protein (FAP). A bispecific CrossMab antibody binding DR5 and FAP refers to a bispecific CrossMab antibody that is capable of binding DR5 and FAP with sufficient affinity such that the antibody is useful as a diagnostic and/or therapeutic agent in targeting cells expressing DR5 and FAP. Specifically, a bispecific CrossMab antibody binding DR5 and FAP refers to a bispecific CrossMab antibody targeting DR5 on a tumor cell and FAP in the stroma surrounding said tumor. The extent of binding of a bispecific antibody that specifically binds death receptor 5 (DR5) and Fibroblast Activation Protein (FAP) to an unrelated, non-FAP or non-DR5 protein may be measured, e.g., by a Enzyme-linked immunosorbent assay (ELISA), surface plasmon resonance (SPR) based assays (e.g. Biacore) or flow cytometry (FACS). A bispecific antibody may specifically bind death receptor 5 (DR5) and Fibroblast Activation Protein (FAP) to an epitope of DR5 or FAP that is conserved among DR5 or FAP from different species.

In preferred embodiments, the multispecific antibody herein comprises an Fc domain. The terms "Fc domain", "Fc region" and analogous terms as used herein refer to the C-terminal region of an IgG antibody, in particular, the C-terminal region of the heavy chain(s) of an IgG antibody, containing the CH2/CH3 domains of the IgG heavy chain. Although the boundaries of the Fc region of an IgG heavy chain can vary slightly, the Fc domain is typically defined as spanning from about amino acid residue Cys226 to the carboxyl-terminus of an IgG heavy chain(s). A "subunit" of Fc region as used herein refers to one of the two polypeptides forming the dimeric Fc region, i.e. a polypeptide comprising C-terminal constant regions of an immunoglobulin heavy chain, capable of stable self-association.

The presence of an Fc domain renders the bispecific antibody amenable to purification using Fc-binding moieties such as, but not limited to, Protein A, Protein G, and/or Protein A/G. The particular structure and amino acid sequence of the CH1-hinge-CH2-CH3 domains of the heavy chains determines the immunoglobulin type and subclass. The multispecific antibodies herein may be of any type (e.g., IgG, IgE, IgM, IgD, IgA and IgY), class (e.g., $IgG_1$ $IgG_2$, $IgG_3$, $IgG_4$, $IgA_1$ and $IgA_2$) or subclass.

The term "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The "variable domain" (variable domain of a light chain (VL), variable domain of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention. Unless otherwise specified herein, numbering of amino acid residues in the variable region or constant region is according to the EU numbering system, also called the EU index, as described in Kabat et al., Sequences of Proteins of Immunological Interest, 5$^{th}$ Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of LI, 50-55 of L2, 89-96 of L3, 31-35B of HI, 50-58 of H2, and 95-102 of H3. (See Almagro and Fransson, Front. Biosci. 13: 1619-1633 (2008).

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E. A., et al., Sequences of Proteins of Immunological Interest, 5$^{th}$ ed., Public Health Service, National Institutes of Health, Bethesda, MD, 1991.

The term "full-length antibody" denotes an antibody consisting of two "full-length antibody heavy chains" and two "full-length antibody light chains". A "full-length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full-length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains.

The term "peptide linker" denotes a peptide with amino acid sequences, which is preferably of synthetic origin. These peptides are used to connect the C-terminus of the Fab region with the N-terminus of a Fab region of a full-length antibody or to connect the N-terminus of a Fab region with the C-terminus of a Fc region of a full-length antibody. The peptide linker is a peptide with an amino acid sequence with a length of at least 30 amino acids, preferably with a length of 32 to 50 amino acids. In one the peptide linker is a peptide with an amino acid sequence with a length of 32 to 40 amino acids. In one embodiment said linker is $(G \times S)n$ with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_6G_2$.

The term "valent" as used within the current application denotes the presence of a specified number of binding sites in an antibody molecule. As such, the terms "bivalent", "trivalent", "tetravalent", and "hexavalent" denote the presence of two binding site, three binding sites, four binding sites, and six binding sites, respectively, in an antibody molecule. The multispecific CrossMab antibodies (including the bispecific CrossMab antibodies) herein are preferably "bivalent", "trivalent" or "tetravalent", more preferably "bivalent" or "tetravalent". Bispecific antibodies are at least "bivalent" and may be "trivalent" or "multivalent" (e.g. "tetravalent" or "hexavalent"). In a particular aspect, the antibodies herein have two or more binding sites and are bispecific. That is, the antibodies may be bispecific even in cases where there are more than two binding sites (i.e. that the antibody is trivalent or multivalent).

The term "chimeric antibody" refers to an antibody comprising a variable region, i.e., binding region, from one source or species and at least a portion of a constant region derived from a different source or species, usually prepared by recombinant DNA techniques. Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. Methods for producing humanized antibodies involve conventional recombinant DNA and gene transfection techniques are well known in the art. See, e.g., Riechmann, L., et al., Nature 332 (1988) 323-327; and Neuberger, M. S., et al., Nature 314 (1985) 268-270.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem.

Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95).

The multispecific CrossMab antibody herein is an antibody in which at least one of the Fab regions of said antibody is a "Crossfab" Fab region, wherein the variable and/or constant domains of the Fab heavy and light chain are exchanged. Such modifications reduce mispairing of heavy and light chains from different Fab fragments, thereby improving the yield and purity of the bispecific antigen binding molecule of the invention in recombinant production. In other words, the mispairing of heavy and light chain in multispecific antibody production is reduced by the exchange of heavy and light chain variable and/or constant domains within one or more Fab regions of the multispecific antigen binding molecule, so that Fab regions of different specificity do not have identical domain arrangement and consequently do not "interchange" light chains.

Possible replacements include the following: (i) the variable domains of the Fab heavy and light chain (VH and VL) are replaced by each other; (ii) the constant domains of the Fab heavy and light chain (CH1 and CL) are replaced by each other; or (iii) the Fab heavy and light chain (VH-CH1 and VL-CL) are replaced by each other (FIG. 1 B-D). As used herein, the term "replacement" refers to the exchange of the variable and/or the constant domain(s) of the Fab heavy and the Fab light chain as used in the context of the present invention. In other words, the terms "replacement" and "exchange" of the variable and/or the constant domain(s) of the Fab heavy and the Fab light chain are used interchangeably and refer to the domain cross-over of the variable and/or the constant domain(s) of the Fab heavy and the Fab light chain as used in the context of the present invention. Examples for cross-over of the variable and/or the constant domain(s) of the Fab heavy and Fab light chain of CrossMab antibodies are given in FIG. 1 A-H, FIG. 2 A-H and FIG. 3 A-D. Mispaired CrossMab antibodies, i.e. wrong pairing of the Fab light and/or Fab heavy chain are indicated by an asterisk.

In one aspect of the present invention, at least one of the Fab regions of said antibody is a Fab region, in which the variable and/or constant domains of the heavy and light chain are exchanged and provided that not the same exchange is made in Fab regions of different binding specificity and provided that the same exchange is made in Fab regions having the same binding specificity.

To achieve the desired result, i.e. prevention of mispairing of heavy and light chains of different specificity, not the same replacement must be made in Fab regions of different specificity. For example, a bispecific CrossMab antibody with a Fab region which specifically binds to a first antigen, the heavy and light chain variable domains may be exchanged, while in a Fab region which specifically binds to a second antigen, the heavy and light chain constant region may not be exchanged. As another example, in a Fab region which specifically binds to a first antigen, no replacement may be made, while in a Fab region which specifically binds to a second antigen, the heavy and light chain variable domains may be exchanged.

In one embodiments of the methods of the present invention, the replacement in a Fab region of an antibody or fragment thereof is a replacement of (i) the variable domains VL and VH by each other; (ii) the constant domains CL and CH1 by each other; or (iii) both the variable and constant domains VL-CL and VH-CH1 by each other.

In a particular preferred embodiment of the present invention, the same replacement is made in Fab regions of the same specificity (i.e. in Fab regions which specifically bind to the same antigen). According to the methods of the present invention, the replacement need not be made in all Fab regions comprised in the bispecific antigen binding molecule. For example, in embodiments wherein there are three Fab regions, it is sufficient to make a replacement only in the Fab region having a different specificity from the other two Fab regions. Specifically, in embodiments wherein the bispecific antigen binding molecule comprises a third Fab region which binds to the first antigen, a replacement is made only in the second Fab region. Similarly, in embodiments wherein the bispecific antigen binding molecule comprises a third Fab region which binds to the second antigen, a replacement is made only in the first Fab region. Thus, in a preferred embodiment of the present invention, the replacement in a Fab region of an antibody or fragment thereof is (i) the variable domains VL and VH by each other; (ii) the constant domains CL and CH1 by each other; or (iii) both the variable and constant domains VL-CL and VH-CH1 by each other; provided that not the same replacement is made in the Fab region having different binding specificity and/or provided that the same replacement is made in Fab regions having the same binding specificity. In a particularly preferred embodiment of the present invention, the replacement in a Fab region of an antibody or fragment thereof is made in all Fab region of an antibody or fragment thereof having the same binding specificity, wherein the replacement is made in said Fab regions comprising the smallest number of Fab regions of the antibody and/or fragment thereof having the same binding specificity. As used herein, the CrossMab antibody of the present invention is a multispecific CrossMab antibody. In a preferred embodiment of the present invention, the multispecific CrossMab antibody is bispecific, trispecific or a tetraspecific antibody. In a particularly preferred embodiment of the present invention, the multispecific CrossMab antibody is a bispecific or a tetraspecific antibody. As used herein, a bispecific antibody comprises a first heavy and a first light chain (originating from an antibody against a first antigen) specifically binding together to a first antigen, and, a second heavy and a second light chain (originating from an antibody against a second antigen) specifically binding together to a second antigen. As used herein, a trispecific antibody comprises a first heavy and a first light chain (originating from an antibody against a first antigen) specifically binding together to a first antigen, a second heavy and a second light chain (originating from an antibody against a second antigen) a specifically binding together to a second antigen, and, a third heavy and a third light chain (originating from an antibody against a third antigen) specifically binding together to a third antigen. As used herein, a tetraspecific antibody comprises a first heavy and a first light chain (originating from an antibody against a first antigen) specifically binding together to a first antigen, a second heavy and a second light chain (originating from an antibody against a second antigen) a specifically binding together to a second antigen, and, a third heavy, a third light chain (originating from an antibody against a third antigen) specifically binding together to a third antigen, and, a fourth light chain (originating from an antibody against a fourth antigen) specifically binding together to a fourth antigen. Thus, a bispecific CrossMab antibody can bind to two antigen molecules at the same time, a trispecific antibody can bind to three antigen molecules at the same time, and a tetraspecific antibody can bind to four antigen molecules at the same time.

Multispecific antibodies, e.g. bispecific antibodies can be derived from full-length antibodies and/or antibody fragments (e.g. F(ab')$_2$ bispecific antibodies). In a preferred embodiment of the present invention, multispecific CrossMab antibodies may be derived from full-length antibodies.

Methods for making multispecific (including bispecific) antibodies are known in the art. Traditional production of full-length bispecific antibodies is based on the coexpression of two immunoglobulin heavy chain-light chain pairs, where the two chains have different specificities (Millstein and Cuello, Nature, 305:537-539[1983]). Purification of the correct molecule can be done by affinity chromatography steps. Similar procedures are disclosed in WO 93/08829, published 13 May 1993, and in Traunecker et al., EMBO J., 10:3655-3659 (1991).

Multispecific antibodies can also be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibodies.

In one particular aspect, the invention purifies bispecific antibodies comprising a first antigen binding site specific for death receptor 5 (DR5) and a second antigen binding site specific for Fibroblast Activation Protein (FAP).

In one embodiment, the bispecific antibody comprises at least one antigen binding site specific for DR5, comprising a variable heavy chain comprising an amino acid sequence of SEQ ID NO.:7 of WO 2014/161845 A1 and a variable light chain comprising an amino acid sequence of SEQ ID NO.:8 of WO 2014/161845 A1; and at least one antigen binding site specific for FAP, comprising a heavy chain variable region comprising an amino acid sequence of SEQ ID NO.: 15 of WO 2014/161845 A1 and a light chain variable region comprising an amino acid sequence of SEQ ID NO.: 16 of WO 2014/161845 A1.

The multispecific CrossMab antibody can for instance be a bivalent, trivalent or tetravalent antibody. 1+1, 2+2 and 2+1 formats as explained above are preferred in the context of the present invention. In one embodiment of the present invention, the multispecific CrossMab antibody is a bispecific bivalent antibody. In another embodiment of the present invention, the multispecific CrossMab antibody is a bispecific trivalent antibody, wherein said bispecific trivalent antibody is monovalent for a first and bivalent for a second antigen binding site or a bispecific tetravalent antibody. In another embodiment of the present invention, the multispecific CrossMab antibody is a bispecific tetravalent antibody is bivalent for a first and second antigen binding site or wherein said bispecific tetravalent antibody is monovalent for a first and trivalent for a second antigen binding site. Thus, in one preferred embodiment, the multispecific CrossMab antibody is a bivalent antibody comprising:

a) one core antibody formed by a full length antibody, the full length antibody comprising two Fab regions, the first Fab region specifically binding to a first antigen and the second Fab region specifically binding to a second antigen; wherein either
the Fab fragments specifically binding to the first antigen, or
the Fab fragments specifically binding to the second antigen comprise a domain crossover such that the variable heavy chain domain (VH) and the variable light chain domain (VL) are replaced by each other.

In one aspect said multispecific CrossMab antibody is a bispecific, tetravalent antibody. It may be bivalent for the first antigen and bivalent for the second antigen. In this case the antibody may comprise
(a) two of said first antigen binding regions; and
(b) two of said second antigen binding regions,
wherein each of said second antigen binding regions is fused via a peptide connector either at the C- or N-terminus of the heavy chain of one of said first antigen binding regions. This antibody may for instance be an IgG antibody and the heavy chains of said first antigen binding regions comprise CH2 and CH3 domains, and wherein each of said second antigen binding regions is fused via a peptide connector to the C-terminus of the heavy chain of one of said first antigen binding regions.

In a particular aspect, the bispecific tetravalent CrossMab antibody comprises
a) two light chains and two heavy chains of an antibody, which specifically binds to a first antigen and comprises two Fab regions;
b) two additional Fab regions of an antibody which specifically binds to a second antigen, wherein said additional Fab regions are fused both via a peptide connector either at the C- or N-termini of the heavy chains of a); wherein in the Fab regions the following modifications are performed:
i) in both Fab regions of a), or in both Fab regions of b), the variable domains VL and VH are replaced by each other, and/or the constant domains CL and CH1 are replaced by each other,
ii) in both Fab regions of a) the variable domains VL and VH are replaced by each other, and the constant domains CL and CH1 are replaced by each other, and in both Fab regions of b) the variable domains VL and VH are replaced by each other, or the constant domains CL and CH1 are replaced by each other,
iii) in both Fab regions of a) the variable domains VL and VH are replaced by each other, or the constant domains CL and CH1 are replaced by each other, and in both Fab regions of b) the variable domains VL and VH are replaced by each other, and the constant domains CL and CH1 are replaced by each other,
iv) in both Fab regions of a) the variable domains VL and VH are replaced by each other, and in both Fab regions of b) the constant domains CL and CH1 are replaced by each other, or v) in both Fab regions of a) the constant domains CL and CH1 are replaced by each other, and in both Fab regions of b) the variable domains VL and VH are replaced by each other.

The components of the bivalent multispecific antibody can be fused to each other in a variety of configurations. Exemplary configurations of bivalent, bispecific CrossMab antibodies are depicted in FIG. 1 A-H.

In particular embodiments, the first Fab region is fused at its C-terminus of its constant domain to the N-terminus of the first subunit of the Fc region. In other embodiments, the second Fab region is fused at its C-terminus of its constant domain to the N-terminus of the second subunit of the Fc region. In a more specific embodiment, the second Fab region is fused at the C-terminus of its constant domain to the N-terminus of the subunit of the first Fc region, which is in turn fused at its N-terminus to the C-terminus of the constant domain of the subunit of the first Fab region.

In a particular embodiment of the present invention, the multispecific CrossMab antibody is a trivalent antibody comprising:
a) one core antibody formed by a full length antibody, the full length antibody comprising two Fab regions, both Fab regions specifically binding to a first antigen; or the first Fab region specifically binding to a first antigen and the second Fab region specifically binding to a second antigen, and
b) one additional Fab region, wherein said additional Fab region is fused either at the C-termini or the N-termini of the heavy chains of the core antibody, wherein the additional Fab region specifically binds to a second antigen provided that the Fab regions according to a) both specifically bind to a first antigen; or wherein the additional Fab region specifically binds to a third antigen provided that the Fab regions according to a) comprise the first Fab region specifically binding to a first antigen and the second Fab region specifically binding to a second antigen,
i) wherein either
the Fab regions specifically binding to the first antigen, the Fab regions specifically binding to the second antigen and/or the Fab regions specifically binding to the third antigen comprise a domain crossover such that the variable heavy chain domain (VH) and the variable light chain domain (VL) are replaced by each other,
provided that not the same replacement is made in the Fab region specifically binding to different antigens and provided that the same replacement is made in the Fab region specifically binding to the same antigens.

Figure 2:
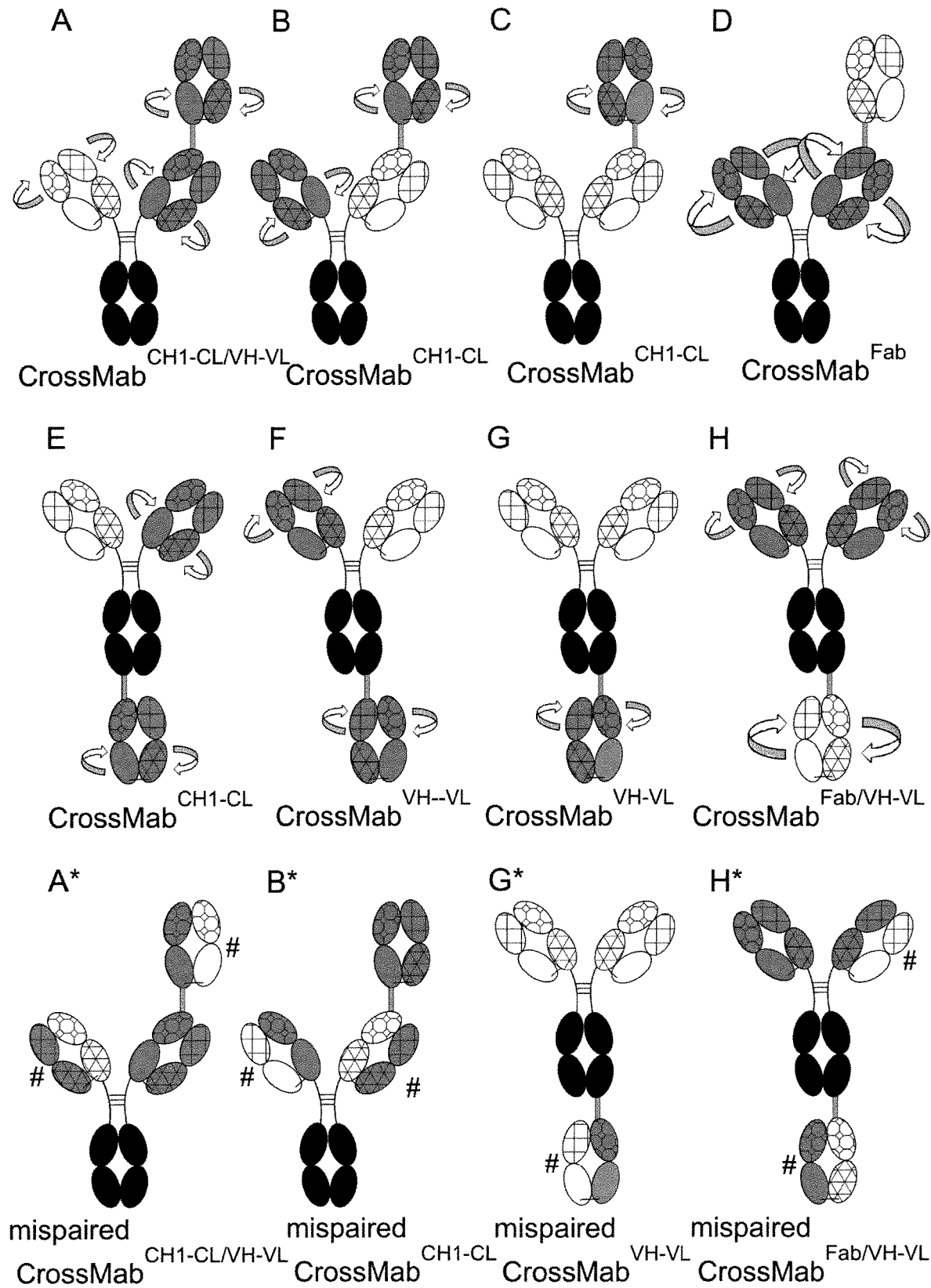
FIG. 2 A-H. Overview of trivalent, bispecific antibodies enabled by CrossMab technology (A-H). The drawings represent only examples, since in many cases crossed and uncrossed Fab regions can be assembled in various ways. Side products resulting from Bence-Jones interaction of the wrong light chain with the heavy chain or the domain-exchanged heavy chain (A* and B*; G* and H*) are shown. Fc region is colored in black, the first Fab region is colored in white and the second Fab region is colored in gray, wherein the CL domain is colored uniformly, the VL domain is colored with a squares pattern, the CH1 domain is colored in a triangle pattern and the VH domain is colored in an octagon pattern.

The components of the trivalent multispecific antibody can be fused to each other in a variety of configurations. Exemplary configurations of trivalent, bispecific CrossMab antibodies are depicted in FIG. 2 A-H.

In particular embodiments, the first Fab region is fused at its C-terminus of its constant domain to the N-terminus of the first subunit of the Fc region. In other embodiments, the second Fab region is fused at its C-terminus of its constant domain to the N-terminus of the second subunit of the Fc region. In a more specific embodiment, the second Fab region is fused at the C-terminus of its constant domain to the N-terminus of the subunit of the first Fc region, which is in turn fused at its N-terminus to the C-terminus of the constant domain of the subunit of the first Fab region.

In other embodiments, the third Fab region is fused at its C-terminus of its constant domain to the N-terminus of the variable domain of the first Fab region, which is in turn fused at its C-terminus of its constant domain to the N-terminus of the first subunit of the first Fc region. In a more specific embodiment, the third Fab region is fused at the C-terminus of its constant domain to the N-terminus of the variable domain of the first Fab region, which is in turn fused at its C-terminus of its constant domain to the N-terminus of the subunit of the first Fc region, and the second Fab region is fused at its C-terminus of the constant domain to the N-terminus of the subunit of the second Fc region.

In other embodiments, the third Fab region is fused at its N-terminus of its variable domain to the C-terminus of the subunit of the first Fc region, which is in turn fused at its N-terminus to the C-terminus of the constant domain of the first Fab region. In a more specific embodiment, the third Fab region is fused at its N-terminus of its variable domain to the C-terminus of the subunit of the first Fc region, which is in turn fused at its N-terminus to the C-terminus of the constant domain of the first Fab region and the second Fab region is fused at its C-terminus of the constant domain to the N-terminus of the subunit of the second Fc region.

In a particular embodiment of the present invention, the multispecific CrossMab antibody is a tetravalent antibody comprising:
a) one core antibody formed by a full length antibody, the full length antibody comprising two Fab regions, both Fab regions specifically binding to a first antigen; or the first Fab region specifically binding to a first antigen and the second Fab region specifically binding to a second antigen, and
b) two additional Fab regions, wherein said additional Fab regions are fused either at the C-termini or the N-termini of the heavy chains of the core antibody, wherein the additional Fab regions specifically bind to a second and/or third antigen provided that the Fab regions according to a) both specifically bind to a first antigen; or wherein the additional Fab regions specifically bind to a third and/or a fourth antigen provided that the Fab regions according to a) comprise the first Fab region specifically binding to a first antigen and the second Fab region specifically binding to a second antigen, wherein either
the Fab regions specifically binding to the first antigen, the Fab regions specifically binding to the second antigen, the Fab regions specifically binding to the third antigen and/or
the Fab regions specifically binding to the fourth antigen comprise a domain crossover such that the variable heavy chain domain (VH) and the variable light chain domain (VL) are replaced by each other,
provided that not the same replacement is made in the Fab region specifically binding to different antigens and provided that the same replacement is made in the Fab region specifically binding to the same antigens.

Figure 3:
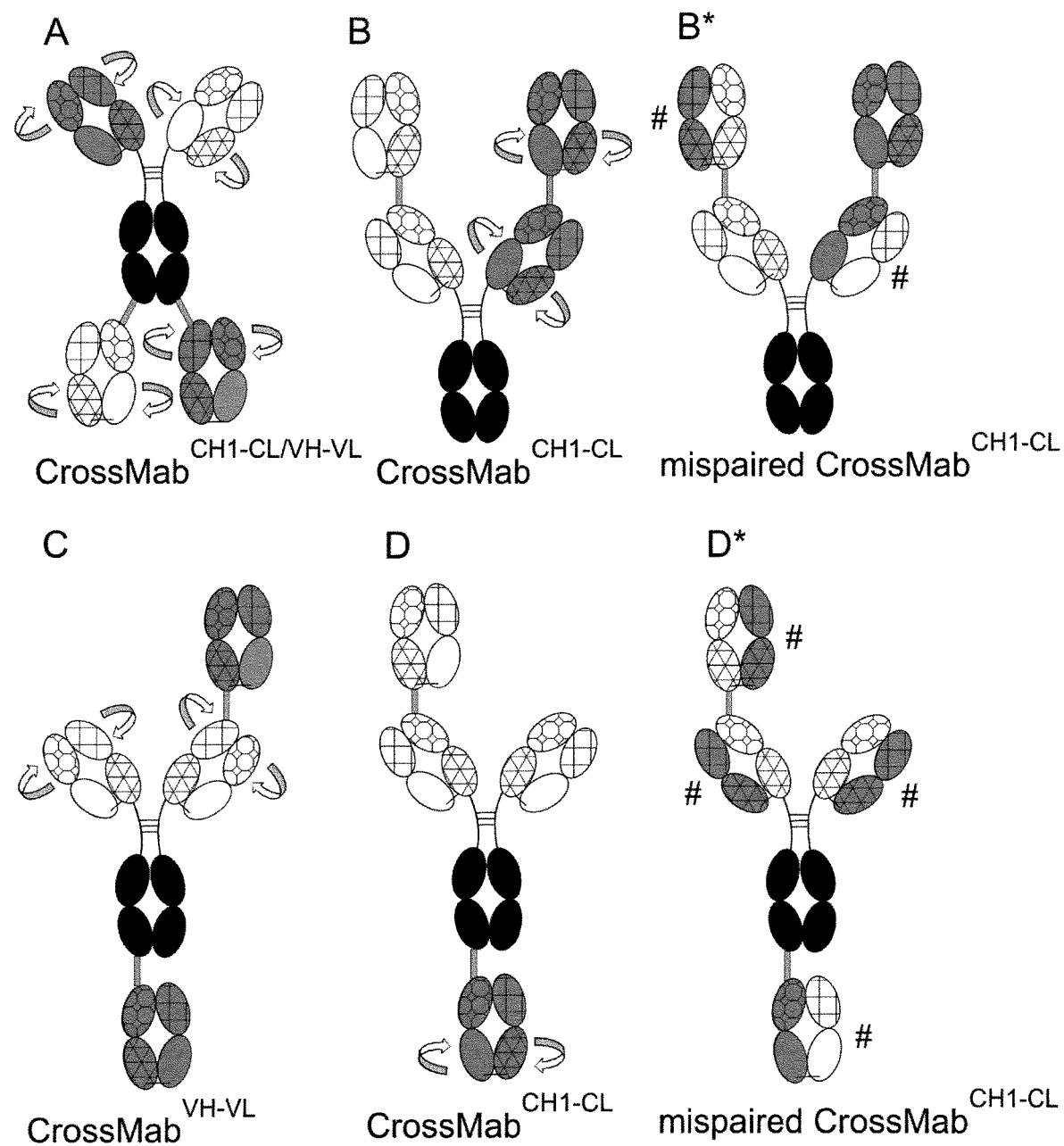
FIG. 3 A-D. Overview of tetravalent, bispecific antibodies (A-C) and a tetravalent, trispecific antibody enabled by CrossMab technology (D). The drawings represent only examples, since in many cases crossed and uncrossed Fab regions can be assembled in various ways. Side products resulting from Bence-Jones interaction of the wrong light chain with the heavy chain or the domain-exchanged heavy chain (A* and D*) are shown. Fc region is colored in black, the first Fab region is colored in white and the second Fab region is colored in gray, wherein the CL domain is colored uniformly, the VL domain is colored with a squares pattern, the CH1 domain is colored in a triangle pattern and the VH domain is colored in an octagon pattern.

The components of the tetravalent multispecific antibody can be fused to each other in a variety of configurations. Exemplary configurations of tetravalent, bispecific CrossMab antibodies are depicted in FIG. 3 A-D.

In particular embodiments, the first Fab region is fused at its C-terminus of its constant domain to the N-terminus of the first subunit of the Fc region. In other embodiments, the second Fab region is fused at its C-terminus of its constant domain to the N-terminus of the second subunit of the Fc region. In a more specific embodiment, the second Fab region is fused at the C-terminus of its constant domain to the N-terminus of the subunit of the first Fc region, which is in turn fused at its N-terminus to the C-terminus of the constant domain of the subunit of the first Fab region.

In other embodiments, the third Fab region is fused at its C-terminus of its constant domain to the N-terminus of the variable domain of the first Fab region, which is in turn fused at its C-terminus of its constant domain to the N-terminus of the first subunit of the first Fc region. In a more specific embodiment, the third Fab region is fused at the C-terminus of its constant domain to the N-terminus of the variable domain of the first Fab region, which is in turn fused at its C-terminus of its constant domain to the N-terminus of the subunit of the first Fc region, and the second Fab region is fused at its C-terminus of the constant domain to the N-terminus of the subunit of the second Fc region.

In other embodiments, the third Fab region is fused at its N-terminus of its variable domain to the C-terminus of the subunit of the first Fc region, which is in turn fused at its N-terminus to the C-terminus of the constant domain of the first Fab region. In a more specific embodiment, the third Fab region is fused at its N-terminus of its variable domain to the C-terminus of the subunit of the first Fc region, which is in turn fused at its N-terminus to the C-terminus of the constant domain of the first Fab region and the second Fab region is fused at its C-terminus of the constant domain to the N-terminus of the subunit of the second Fc region.

In other embodiments, the fourth Fab region is fused at its C-terminus of its constant domain to the N-terminus of the variable domain of the second Fab region, which is in turn fused at its C-terminus of its constant domain to the N-terminus of the second subunit of the first Fc region. In a more specific embodiment, the fourth Fab region is fused at the C-terminus of its constant domain to the N-terminus of the variable domain of the second Fab region, which is in turn fused at its C-terminus of its constant domain to the N-terminus of the subunit of the second Fc region, and the third Fab region is fused at its C-terminus of its constant domain to the N-terminus of the first Fab region, which is in turn fused at its C-terminus of the constant domain to the N-terminus of the subunit of the first Fc region. In an alternative embodiment, the fourth Fab region is fused at the C-terminus of its constant domain to the N-terminus of the variable domain of the second Fab region, which is in turn fused at its C-terminus of its constant domain to the N-terminus of the subunit of the second Fc region, and the third Fab region is fused at its N-terminus of its variable domain to the C-terminus of the subunit of the first Fc region, which is in turn fused at its N-terminus to the C-terminus of the constant domain of the first Fab region.

In other embodiments, the fourth Fab region is fused at its N-terminus of its variable domain to the C-terminus of the subunit of the second Fc region, which is in turn fused at its N-terminus to the C-terminus of the constant domain of the second Fab region. In a more specific embodiment, the fourth Fab region is fused at its N-terminus of its variable domain to the C-terminus of the subunit of the second Fc region, which is in turn fused at its N-terminus to the C-terminus of the constant domain of the second Fab region and the third Fab region is fused at the N-terminus of its variable domain to the C-terminus of the subunit of the first Fc region, which is in turn fused at its N-terminus to the C-terminus of the constant domain of the first Fab region. In a more specific embodiment, the fourth Fab region is fused at its N-terminus of its variable domain to the C-terminus of the subunit of the second Fc region, which is in turn fused at its N-terminus to the C-terminus of the constant domain of the second Fab region and the third Fab region is fused at the C-terminus of its constant domain to the N-terminus of the first Fab region, which is in turn fused at its C-terminus of the constant domain to the N-terminus of the subunit of the first Fc region.

According to any of the above embodiments, components of the multivalent, multispecific CrossMab antibody (e.g. Fab regions, Fc subunit) may be linked directly or through various linkers, particularly peptide linkers comprising one or more amino acids, typically about 2-20 amino acids, that are described herein or are known in the art. Suitable, non-immunogenic peptide linker include, for example, $(G_4S)_n$, $(SG_4)_n$, $(G_4S)_n$ or $G_4(SG_4)_n$ peptide linkers, wherein n is generally a number between 1 and 10, typically between 2 and 4. A particularly suitable peptide linker for fusing the light chains of the first and the second Fab fragment to each other is $(G_4S)_2$. Additionally, peptide linkers may comprise (a portion of) an immunoglobulin hinge region. An exemplary such linker is EPKSC(D)-$(G_4S)_2$. Particularly where a Fab region is linked to the N-terminus of a subunit of a Fc region, it may be linked via an immunoglobulin hinge region or a portion thereof, with or without an additional peptide linker. In one embodiment of the present invention, the N-terminus of the first and/or second Fab region and C-terminus of a third and/or fourth Fab region are fused to each other, optionally via a peptide linker. In a further embodiment of the present invention, the C-terminus of the subunit of the first and/or second Fc regions and the N-terminus of the third and/or fourth Fab region are fused to each other, optionally via a peptide linker.

The Fc region of the bispecific antigen binding molecule consists of a pair of polypeptide chains comprising heavy chain domains of an antibody molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. The bispecific antigen binding molecule of the invention comprises not more than one Fc domain. In one embodiment according to the invention the Fc domain of the bispecific antigen binding molecule is an IgG Fc region. In a particular embodiment the Fc domain is an $IgG_1$ Fc domain. In another embodiment the Fc domain is an $IgG_4$ Fc domain.

Bispecific antigen binding molecules according to the invention comprise different Fab regions, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of bispecific antigen binding molecules in recombinant production, it will thus be advantageous to introduce in the Fc domain of the bispecific antigen binding molecule a modification promoting the association of the desired polypeptides.

Accordingly, in particular embodiments, the Fc domain comprises a modification promoting the association of the first and the second Fc domain subunit. A modification may be present in the first Fc domain subunit and/or the second Fc domain subunit.

The site of most extensive protein-protein interaction between the two subunits of a human IgG Fc domain is in the CH3 domain of the Fc domain. Thus, in one embodiment said modification is in the CH3 domain of the Fc domain. Several approaches for CH3—modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein incorporated by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

In a specific embodiment said modification is a so-called "knob-into-hole" (KiH) modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first Fc domain subunit of the bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second Fc domain subunit an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

Apart from the "knob-into-hole technology" other techniques for modifying the CH3 domains of the heavy chains of a multi specific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody according to the invention.

These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the multispecific antibodies according to the invention which reduce light chain mispairing. However, the preparation of multispecific CrossMAb antibodies optionally in combination with KiH technology is not completely free of mispaired variants thereof. In one embodiment of the present invention, the mispaired variant thereof comprises at least one light chain of the multispecific CrossMab antibody thereof that is replaced by another light chain of said multispecific CrossMab antibody.

As used herein, in a bivalent, multispecific antibody, i.e. in a bivalent, bispecific antibody, binding of the unmodified light chain to the modified heavy chain and binding of the modified light chain to the unmodified heavy chain is possible. Alternatively, the binding of a first modified light chain to a second modified heavy chain and/or the binding a second modified light chain to a first modified heavy chain is possible. In other words, the binding of the first light chain to the second heavy chain and/or the binding of the second light chain to the first heavy chain is possible (see FIG. 1 A-H).

As used herein, in a trivalent, multispecific antibody, i.e. in a trivalent, bispecific antibody, binding of the unmodified light chain to the modified heavy chain and binding of the modified light chain to the unmodified heavy chain is possible. Alternatively, the binding of a first modified light chain to a second modified heavy chain and/or the binding a second modified light chain to a first modified heavy chain is possible. In other words, the binding of the first light chain to the second heavy chain and/or the binding of the second light chain to the first heavy chain is possible (see FIG. 2 A-H).

As used herein, in a tetravalent, multispecific antibody, i.e. in a tetravalent, bispecific antibody or a tetravalent, trispecific antibody, binding of the unmodified light chain to the modified heavy chain and binding of the modified light chain to the unmodified heavy chain is possible. Alternatively, the binding of a first modified light chain to a second modified heavy chain and/or the binding a second modified light chain to a first modified heavy chain is possible. In other words, the binding of the first light chain to the second heavy chain and/or the binding of the second light chain to the first heavy chain is possible (see FIG. 3 A-H).

Purification of CrossMab Antibodies

In particular, the invention encompasses the separation and/or purification of multispecific CrossMab antibodies, e.g., bispecific CrossMab antibodies, from the products of cells, cell lines and cell cultures. Such products typically include conditioned cell media and/or lysed and homogenized cells and cell cultures (e.g., homogenized cells and cell components within conditioned cell media). The methods of the invention are particularly suited to the processing of products from transgenic host cells, host cell lines and host cell cultures, wherein the transgenic cells, cell lines and cell cultures express the molecule of interest.

The term "host cell" as used in the current application denotes any kind of cellular system which can be engineered to generate the antibodies according to the current invention. In one embodiment HEK293 cells and CHO cells are used as host cells.

As used herein, the expressions "cell", "cell line", and "cell culture" are used interchangeably, and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., van der Eb, A. J., Virology 52 (1973) 546-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N., et al, PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

It is understood that the methods of the invention relate to the separation, purification and/or processing of a multispecific CrossMab antibody from a solution comprising the multispecific CrossMab antibody and the mispaired variant(s) thereof. The solution comprising the multispecific CrossMab antibody and the mispaired variant(s) thereof according to the methods of the present invention includes the loading buffer of a HIC process, e.g. the load applied to the HIC medium, e.g. as part of a purification scheme. Therefore, as used herein, the term) "solution" with reference to a liquid composition including the CrossMab multispecific antibody and the mispaired variant(s) thereof is a solution that is used for the implementation of the methods disclosed herein. As such, where the solution comprising the multispecific CrossMab antibody and the mispaired variant(s) thereof is cell culture medium or a fractionated or clarified part of cell a culture medium, it is understood that such a medium is necessarily conditioned cell culture medium (so as to comprise the multispecific CrossMab multispecific antibody). Therefore, as used herein, the term "cell culture solution" and analogous terms refer to any solution of a biological process or system expected to comprise the multispecific CrossMab antibody, including but not limited to, e.g., conditioned cell culture supernatant; clarified conditioned cell culture supernatant; clarified, homogenized/lysed cell cultures, etc. In a particular embodiment, the solution may comprise cell culture medium that is clarified and/or sterilized prior to implementation of the methods disclosed herein. As used herein, the term "clarified" and "clarification" refer to the removal of particulate matter from a solution, including but not limited to filtration sterilization and/or centrifugation. Thus, the solution is a "clarified harvest", referring to a liquid material containing CrossMab multispecific antibody and the mispaired variant thereof that has been extracted from cell culture, for example, a fermentation bioreactor, after undergoing centrifugation to remove large solid particles and/or subsequent filtration to remove finer solid particles and impurities from the material.

In various embodiments, the sample comprising the multispecific CrossMab antibody and mispaired variants thereof may be partially purified. For example, the solution may have already been subjected to any of a variety of art recognized purification techniques, such as chromatography, e.g., ion exchange chromatography, mixed mode chromatography, and/or affinity chromatography, or filtration, e.g., depth filtration, nanofiltration, ultrafiltration and/or absolute filtration.

Hence, in one aspect said method of the present invention further comprises one or more further purification step(s) prior and/or after the HIC step.

In particular, said method may comprise prior to said HIC step at least one purification step selected from the group consisting of affinity chromatography such as protein A affinity chromatography, ammonium sulfate precipitation, ion exchange chromatography and gel filtration. Moreover, said method may comprise after said HIC step at least one purification step selected from the group consisting of ion exchange chromatography, gel filtration and affinity chromatography.

Preferably, in the method according to the present invention, a protein A step is performed prior to the HIC step.

In one typical aspect, the HIC step herein is performed after a protein A step and is followed by a cation exchange step in bind-and-elute mode and an anion exchange step in flow-through mode.

The term "chromatography medium" as used herein refers to a solid phase material that is capable of selective binding to one or more components of an applied load fluid as is well known in the art. The invention encompasses, in particular, the use of HIC medium defined herein for the processing of the multispecific CrossMab antibody. The methods of the invention further encompass combination of the hydrophobic interaction chromatography with one or more further chromatographic processes (e.g., ion exchange chromatography) as part of a purification scheme for the separation of the molecule of interest, i.e., a multispecific CrossMab antibody, from one or more impurities and/or byproducts, e.g. from incomplete assembled antibodies. Examples of chromatographic unit operations with which the HIC can be combined according to the methods of the invention include, but are not limited to, chromatographic unit operations comprising the use of solid phases (e.g., resins) that selectively bind to one or more components of a load fluid via cation exchange, anion exchange, hydrophobic interaction, hydrophilic interaction, hydrogen bonding, pi-pi bonding, metal affinity and/or specific binding via biomolecules (e.g., affinity resins comprising immunoglobulins, immunoglobulin fragments, and enzymes). The solid phase can be a porous particle, nonporous particle, membrane, or monolith. It is within the ability of the person of skill in the art to develop appropriate conditions for these additional chromatographic unit operations and to integrate them with the invention disclosed herein to achieve purification of a particular bispecific antibody.

The term "hydrophobic interaction chromatography or "HIC" refers to a purification technique that exploits the interaction of HIC media with hydrophobic regions present on a protein of interest, such as an antibody, and/or those present on an impurity to separate a protein of interest present in a solution. HIC is often utilized in either a bind-elute mode, in which the protein of interest remains bound to the HIC media until eluted during an elution phase, or a flow through mode, in which the protein of interest flows through the column while the impurity binds to the media.

The term "applying to" or "subjecting to" or grammatical equivalents thereof denotes a partial step of a purification method, in particular on a HIC medium, in which a solution comprising the multispecific CrossMab antibody and mispaired variant(s) thereof, wherein the multispecific CrossMab antibody is to be purified, is brought into contact with a stationary phase. This denotes that said solution is added to a chromatographic device in which the stationary phase is located. The solution comprising the multispecific CrossMab antibody to be purified passes through the stationary phase allowing for interaction between the stationary phase and the substances in solution. Depending on the conditions, such as e.g. pH, conductivity, salt concentration, temperature, and/or flow rate, some substances of the solution are bound to the stationary phase and, thus, are removed from the solution. Other substances remain in solution. The substances remaining in solution can be found in the flow-through. The "flow-through" denotes the solution obtained after the passage of the chromatographic device irrespective of its origin. A washing step may be optionally applied to flush the column. Subsequently, the application of an eluting buffer may be used to cause the elution of one or more substances, i.e. the multispecific CrossMab antibody and/or the mispaired variant(s) thereof, bound to the stationary phase. The substance can be recovered from the solution after the HIC purification step by methods familiar to a person of skill in the art, such as e.g. precipitation, salting out, ultrafiltration, diafiltration, lyophilization, affinity chromatography, or solvent volume reduction to obtain the substance of interest in purified or even substantially homogeneous form.

The term "bind-and-elute mode" denotes a way to perform a HIC chromatography purification method. Herein a solution comprising the multispecific CrossMab antibody to be purified and mispaired variant(s) thereof is applied to a stationary phase, particularly a solid phase, whereby the multispecific CrossMab antibody and/or the mispaired variants thereof interact with the stationary phase and is retained thereon. Substances not of interest are removed with the flow-through or the supernatant, respectively. The multispecific CrossMab antibody is afterwards recovered from the stationary phase in a second step by applying an elution solution (typically a buffered solution), typically in a stepwise or linear gradient (or a combination thereof) such that the multispecific CrossMab elutes separately from the variant (more different variants) thereof.

As used herein, "buffer" refers to a buffered solution that resists changes in pH by the action of its acid-base conjugate components. The buffer for the hydrophobic interaction chromatography aspect of this invention may typically have a pH in a range of about 5.0-8.5, preferably about 5-7. Examples of buffers that will control the pH within this range include phosphate, acetate, citrate, sodium or ammonium buffers, or more than one. Typical buffers are citrate and ammonium buffers, e.g. ammonium sulfate, sodium sulfate or ammonium citrate buffers, in particular embodiments ammonium sulfate or ammonium citrate buffers. Optionally, the buffered solution may also comprise an additional inorganic salt. In one embodiment the inorganic salt is selected from sodium chloride, potassium chloride, potassium sulfate, sodium citrate, and potassium citrate. The "loading buffer" is that which is used to load the mixture of the antibody and contaminant on the HIC column and the "washing buffer" is that which is used to wash the HIC column in order to flush unbound material from the HIC column. "Elution buffer" is that which is used to elute the antibody from the column. Often the loading buffer and washing buffer will be the same. According to the methods of the present invention, the eluting buffer has a lower salt concentration than the loading and/or eluting buffer.

HIC is widely used in protein purification as a complement in a multi step purification sequence of other techniques that separate according to charge, size, biospecific recognition and the like. Generally, the position of a hydrophobic interaction chromatography is variable in a multi step purification sequence of an antibody and/or fragments thereof. Such methods in a multi step purification sequence for purifying an antibody and/or fragments thereof are well established and widespread used. They are employed either alone or in combination. Such methods are, for example, affinity chromatography using thiol ligands with complexed metal ions (e.g. with Ni(II)- and Cu(II)-affinity material) or microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), size exclusion chromatography, and preparative electrophoretic methods (such as gel electrophoresis, capillary electrophoresis).

For example, when using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In one embodiment of the present invention, upstream purification step(s) are selected from the group consisting of affinity chromatography, protein A affinity chromatography, ammonium sulfate precipitation, ion exchange chromatography and/or gel filtration.

The following purification process of immunoglobulins in general may comprise a multistep chromatographic part. In the first step non-immunoglobulin polypeptides and proteins may be separated from the immunoglobulin fraction by an affinity chromatography, e.g. with protein A. Afterwards an ion exchange chromatography can be performed to disunite the individual immunoglobulin classes and to remove traces of protein A, which has been co-eluted from the first column. Finally a third chromatographic step may be necessary to separate immunoglobulin monomers from multimers and fragments of the same class. Sometimes the amount of aggregates is high (5% or more) and it is not possible to separate them efficiently in the third purification step necessitating further purification steps.

Further examples of suitable purification steps include hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13[1983]). Protein G is recommended for all mouse isotypes and for human γ3 (Guss et al., EMBO J. 5:15671575[1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Hydrophobic Interaction Chromatography

Following any upstream purification step(s), the solution comprising the multispecific CrossMab antibody and the mispaired variant thereof is suspended in a loading buffer and subjected to the HIC medium.

In general, HIC separates proteins according to differences in their surface hydrophobicity by utilizing a reversible interaction between these proteins and the hydrophobic surface of a HIC medium. The interaction between hydrophobic proteins and a HIC medium is influenced significantly by the presence of certain salts in the buffer. A high salt concentration enhances the interaction while lowering the salt concentration weakens the interaction. For example, the interaction of a protein with a HIC medium is reversed as the ionic strength of the buffer is reduced and the protein with the lowest degree of hydrophobicity is eluted first. The most hydrophobicity protein elutes last, requiring a greater reduction in salt concentration to reverse interaction.

In detail, the solution comprising the multispecific CrossMab antibody and the mispaired variant thereof in a high salt buffer are loaded on the HIC column. In general, the salt in the buffer interacts with water molecules to reduce the solvation of the molecules in solution, thereby exposing hydrophobic regions in the sample molecules which are consequently adsorbed by the HIC column. The more hydrophobic the molecule, the less salt needed to promote binding. Usually, a decreasing salt gradient is used to elute molecules from the HIC column. As the ionic strength decreases, the exposure of the hydrophilic regions of the molecules increases and molecules elute from the column in order of increasing hydrophobicity. Elution of the molecules may also be achieved by the addition of mild organic modifiers or detergents to the elution buffer. HIC is reviewed in Protein Purification, 2d Ed., Springer-Verlag, New York, pgs 176-179 (1988).

The HIC technique is a common next step when samples have been subjected to ammonium sulfate precipitation or after separation by ion exchange chromatography. In both situations, the solution comprising the multispecific CrossMab antibody and mispaired variants thereof contains a high salt concentration and may be applied directly to the HIC medium with little or no additional preparation.

Therefore, one embodiment of the present invention comprises applying a solution comprising the multispecific CrossMab antibody and mispaired variants thereof to the HIC medium, wherein the multispecific CrossMab antibody and mispaired variant thereof are separately eluted from the HIC medium, thereby separating the multispecific CrossMab antibody from the mispaired variant thereof in the solution based on hydrophobicity.

In other words, the method of the present invention comprises separating a multispecific CrossMab antibody in a solution comprising the multispecific CrossMab antibody and mispaired variant thereof, comprising the following steps:

(a) subjecting the solution comprising the multispecific CrossMab antibody and mispaired variant thereof to a HIC medium, in the presence of a loading buffer wherein the multispecific CrossMab antibody and mispaired variant thereof binds to said HIC medium;

(b) optionally washing the HIC medium in the presence of a washing buffer, wherein the multispecific CrossMab antibody and mispaired variant thereof remains bound upon washing; and (c) selectively eluting the multispecific CrossMab antibody and mispaired antibody thereof from the HIC medium in the presence of an eluting buffer, utilizing eluting conditions that allow the separation of the multispecific CrossMab antibody and mispaired variant thereof based on hydrophobicity.

In an alternative embodiment of the present invention, conditions can be chosen to maximize the binding of contaminants, such as mispaired variants of the multispecific CrossMab antibody, and allow the target, i.e. the multispecific CrossMab antibody to pass through the column thus removing the contaminants, i.e. the mispaired variants of the multispecific CrossMab antibody.

In view of the above, the method of the present invention comprises separating a multispecific CrossMab antibody in a solution comprising the multispecific CrossMab antibody and mispaired variant thereof by HIC in a bind-and-elute mode. Alternatively, as described above, the method of the present invention comprises separating a multispecific CrossMab antibody in a solution comprising the multispecific CrossMab antibody and mispaired variant thereof by HIC in a flow-through mode.

Before each run of a HIC separation as described above, the medium may be equilibrated with a equilibrating buffer that fills the pores of the matrix and the space in between the particles. In one embodiment of the present invention, an equilibrating buffer comprising between 10 mM and 500 mM sodium acetate, more preferably between 10 mM and 50 mM sodium acetate, and between 1.0 and 2.0 M ammonium sulfate, more preferably between 1.0 and 1.5 M ammonium sulfate is subjected to the HIC medium prior to subjecting the solution comprising the multispecific CrossMab antibody and mispaired variant thereof the HIC medium. In a particular embodiment of the present invention, about 5-10 CV of the equilibrating buffer is subjected to the HIC medium. In a particularly preferred embodiment of the present invention, about 5-10 CV of the equilibrating buffer comprising between 10 mM and 500 mM sodium acetate, more preferably between 10 mM and 50 mM sodium acetate, and between 1.0 and 2.0 M ammonium sulfate, more preferably between 1.0 and 1.5 M ammonium sulfate, is subjected to the HIC medium. Since proteins to be purified commonly carry both hydrophilic and hydrophobic areas on their surface, protein precipitation having the same driving force as seen when hydrophobic proteins interact with a HIC medium may be enhanced by increased concentration of certain salts. Precipitation of the protein to be purified may impair their separation and thus, may reduce yield. Thus, before starting a HIC separation, the salt concentration in the buffers may need to be reduced in order to prevent precipitation during the run. By this means, the highest salt concentration at which the protein to be purified does not precipitate can be determined experimentally. For example, increasing concentrations of salt may be added to the sample in order to establish the concentration at which precipitation is caused. Thus, the salt concentration can be adjusted to a value below this concentration to avoid the risk of precipitation of the sample due to high salt concentrations when applied to a HIC medium.

Subsequent to the equilibrating buffer to the HIC medium, solution comprising the multispecific CrossMab antibody and mispaired variant thereof suspended in a loading buffer is subjected to the HIC medium. The medium may be packed into a column to form a packed bed. Increasing the column length may improve resolution when subjecting large ample volumes to the HIC medium. In particular, longer column lengths may improve resolution of closely-related proteins.

Although HIC media are described according to the type of ligand, and, sometimes, ligand density, the binding capacity of a HIC medium for a protein being purified is also of relevance for the hydrophobicity of a HIC medium. Herein, the density of the substituted ligands is preferably between 9 and 50 µmol per ml HIC medium. The binding capacity refers to the actual amount of protein that can bind to a HIC medium, under defined experimental conditions. The binding capacity of HIC media increases with increased ligand density up to a certain level. Furthermore, binding capacity is determined largely by the HIC medium, protein properties and the binding conditions, size and shape of molecules, particle size of the matrix and, to a lesser extent by flow rate, temperature and pH. If the defined conditions used for a HIC separation include the flow rate at which the buffers were subjected to the HIC medium, the amount bound is referred to as the dynamic binding capacity of the HIC medium. Thus, the dynamic binding capacity can be increased, for example, by decreasing or increasing the flow rates so that a balance must be found between achieving the maximum dynamic binding capacity and a fast separation, particularly when applying large sample volumes. The dynamic binding capacity is dependent on the properties of the HIC medium, the protein being purified and the experimental conditions such as salt concentration of the buffers, flow rate, temperature and, to a lesser extent, pH. The dynamic binding capacity of the HIC medium is according to the manufacturer's specifications often between 19 and 39 mg protein (typically determined using bovine serum albumin (BSA) at 10% break-through) per mL medium. However, due to the dependency of the dynamic binding capacity on several parameters as outlined above, the dynamic binding capacity of a HIC medium can be experimentally determined for a protein to be purified, e.g. an antibody as used in the context of the present invention.

As a binding technique, HIC is independent of sample volume as long as the salt content of the solution comprising the protein to be purified suspended in the loading buffer ensure adequate binding conditions. The amount of sample that can be applied to a HIC a column depends on the binding capacity of the medium and the degree of resolution required. Furthermore, the amount of sample may have an influence on resolution since the width of the peaks is directly related to the amount of substance present. Thus, in context of the methods of the present invention, the amount of protein applied and bound to the medium should not exceed the total binding capacity of the column.

In general, interaction between the protein and the HIC medium is promoted by moderately high salt concentrations, for example 1-2 M ammonium sulfate or 3 M NaCl. The type and the concentration of the loading buffer required are selected to ensure that the proteins of interest bind to the medium and that other less hydrophobic proteins and impurities pass directly through the column.

When using HIC media the ability of a particular salt of the buffer to promote hydrophobic interaction depends on the ionic species present and their concentration. In general, the eluting/precipitation strength of an ion can be described by the Hofmeister series. For example, sodium, potassium or ammonium sulfats produce relatively high precipitation. It is these salts that may effectively promote ligand-protein interaction on a HIC medium and may have a stabilizing influence on proteins structure. Hence, the commonly used salts are $(NH_4)_2SO_4$, $Na_2SO_4$, NaCl, KCl and $CH_3COONH_4$, $CH_3COONa$ and the like. As with media selection, each salt may differ in its ability to promote hydrophobic interactions. Thus, the correct choice of salt and salt concentration are important parameters that influence capacity and final selectivity of a HIC separation. In this context, as the concentration of salt increases, the amount of protein bound may increase almost linearly up to a specific salt concentration and may continue to increase in an exponential manner at higher concentrations. Selection of buffering ions is not critical for hydrophobic interaction. Phosphate buffers are most commonly used. The pH of the buffer chosen should be compatible with protein stability. The pH of the buffers should be chosen to be compatible with protein stability. However, between 5.0 and 8.5 pH values have very little significance on the final selectivity and resolution of a HIC separation. Thereby, an increase in pH weakens hydrophobic interactions and retention of protein changes more drastically at pH values above 8.5 or below 5.0. Optionally, buffer additives can be used to improve selectivity and resolution. Thereby, additives can influence a separation by improving protein solubility or promoting elution of bound proteins. For example, water-miscible alcohols, detergents, and chaotropic salts are commonly used additives in HIC separations.

Furthermore, the type and concentration of salt used in the buffers applied to the HIC medium may influence capacity, selectivity and resolution of a HIC separation. Therefore, improving the type and concentration of salt in said buffers may be essential for the binding process of the multispecific CrossMab antibody and/or mispaired variant thereof on a HIC medium and thus for achieving the required selectivity to bind these antibodies. For example, at a given concentration, ammonium sulfate in a buffer often gives the best resolution when compared to other salts may be used at concentrations up to 2 M. Commonly used salts in buffers used in HIC separation include but are not limited to sodium, potassium and/or ammonium sulfates effectively promoting ligand-protein interactions in HIC and have a stabilizing influence on protein structure.

The flow rate of the buffers subjected to the HIC medium can be varied according to the stage of the separation, i.e. the flow rate of the loading buffer, the washing buffer and/or the eluting buffer subjected to the HIC medium can be different. Lower flow rates allow time for binding and elution, higher flow rates could save time during equilibration. Flow rates are limited primarily by the rigidity of the media.

In one embodiment of the present invention, a loading buffer comprising the multispecific CrossMab antibody and mispaired variant thereof and comprising between 10 mM and 500 mM sodium acetate, more preferably between 10 mM and 50 mM sodium acetate, and between 1.0 and 2.0 M ammonium sulfate, more preferably between 1.0 and 1.5 M ammonium sulfate, is subjected to the HIC medium. In one embodiment of the present invention, the pH, salt concentrations and/or volumes subjected to the HIC medium of the loading buffer is substantially identical to the equilibrating buffer.

When loading of the solution comprising the multispecific CrossMab antibody and mispaired variant thereof is completed, the column is washed so that all non-bound proteins pass through the medium.

In one embodiment of the present invention, a washing buffer comprising between 10 mM and 500 mM sodium acetate, more preferably between 10 mM and 50 mM sodium acetate and between 1.0 and 2.0 M ammonium sulfate, more preferably between 1.0 and 1.5 M ammonium sulfate, is subjected to the HIC medium. In a preferred embodiment of the present invention, about 5-10 CV of the loading buffer is subjected to the HIC medium. In one embodiment of the present invention, the pH, salt concentrations and/or volumes subjected to the HIC medium of the washing buffer is substantially identical to the equilibrating buffer and/or the loading buffer.

In general, proteins are eluted by decreasing the salt concentration in the eluting buffer. As the level of salt decreases those proteins with the lowest hydrophobicity begin to elute from the column. By controlling the changes in salt concentration using gradients, proteins are eluted differentially in a purified, concentrated form. Those proteins with the highest degree of hydrophobicity will be most strongly retained and will be eluted last. The eluting buffer is commonly comprises substantially the same pH and salt concentration as the loading and/or the washing buffer, but with at least one salt concentration that is decreased compared to said at least one salt concentration in the loading and/or the washing buffer. The skilled person in the art is aware of the determination of salt concentration and buffer volumes required to elute the contaminating weaker binding substances. In one embodiment of the present invention, the salt concentration of at least one salt of the eluting buffer subjected to the HIC medium is reduced compared to said salt in the loading and/or washing buffer. Typically, the eluting buffer comprises the same salt types as the loading and/or washing buffer, wherein the salt concentration of at least one salt of the eluting buffer subjected to the HIC medium is reduced compared to said salt in the loading and/or washing buffer.

In one embodiment of the present invention, about 10-40 CV of the eluting buffer is subjected to the HIC medium in a linear or stepwise gradient to no or low salt conditions.

In a particular embodiment, about 10-30 CV of the eluting buffer is subjected to the HIC medium in a linear or stepwise gradient to no or low salt conditions.

In one embodiment of the present invention, the eluting buffer is subjected to the HIC medium in a linear gradient, a stepwise gradient, or a combination thereof in a linear-stepwise gradient. In a preferred embodiment of the present invention, the eluting buffer is subjected to the HIC medium in a linear gradient. Linear gradient elution is often used for high-resolution separation, whereas stepwise gradient elution may be used when a HIC separation has been optimized using linear gradient elution, changing to a step gradient elution speeds up separation times and reduces buffer consumption while retaining the required purity level. In any case, the salt concentration of the eluting gradient subjected to the HIC medium is reduced.

For a high-resolution of a HIC separation, a broad gradient may be used in order to bind as many proteins as possible and then elute them differentially to obtain a comprehensive profile.

Subsequent to the gradient, a washing-step in a salt-free buffer may be subjected to the HIC medium to remove most tightly bound proteins at the end of an elution. Preferably, a salt-free washing step at the end of each run should remove any molecules that are still bound to the HIC medium. As understood in the context of the present invention, a salt-free buffer refers to a buffer which do not substantially contain any salts or distilled water. If the hydrophobicity of the medium and the proteins in the sample have been judged correctly, all proteins will be eluted by this stage. Most bound proteins may be effectively eluted by simple washing the HIC medium with salt-free buffer. Occasionally, the hydrophobic interaction is so tight that harsher conditions may be required to remove all bound material, for example, 0.5-1.0 M NaOH, 70% ethanol or 30% isopropanol. As used in the context of the present invention, at least one washing-step in a salt-free buffer may be applied to the HIC medium. The salt-free buffer as used in accordance with the present invention may be (i) distilled water, (ii) about 1 M acetic acid and about 20% ethanol or (iii) about 0.1 M sodium hydroxide. In a preferred embodiment of the present invention, a first washing-step in a salt-free buffer comprising about 1 M acetic acid and about 20% ethanol is applied and a second washing-step in a salt-free buffer comprising 0.1 M sodium hydroxide is applied.

These washing-step(s) should be followed by a water or a salt-free buffer wash before re-equilibrating the column with the equilibrating buffer as described above, e.g. to avoid the risk of ethanol in the storage solution causing salt precipitation. Preferably, the column is re-equilibrated in equilibration buffer before applying the solution in a next run.

During HIC separation, the multispecific CrossMab antibody is purified and eluted in smaller volumes, thereby concentrating the multispecific CrossMab antibody so that it can go directly to downstream purification processes encompassing those known in the art, for example but not limited to gel filtration or, after a buffer exchange, to an ion exchange separation. The selection and combination of downstream purification step(s) depend upon the specific sample properties and the required level of purification.

In one embodiment of the present invention, downstream purification step(s) are selected from the group consisting of ion exchange chromatography, gel filtration, reversed phase chromatography, affinity chromatography and/or mixed-mode chromatography. As used herein, the method of the present invention comprises after said HIC step at least one purification step. Preferably, the method of the present invention comprises after said HIC step at least one purification step selected from the group consisting of ion exchange chromatography, gel filtration and affinity chromatography.

HIC media are composed of ligands containing alkyl or aryl groups coupled to an inert matrix of spherical particles. The ligand and the degree of ligand substitution on a HIC matrix contribute to the selectivity and, in addition, to the hydrophobicity of the medium. Thus, the type of ligand and the nature of the target protein are highly significant parameters in determining the selectivity of a HIC medium. The most common hydrophobic ligands of HIC media fall into two groups depending on their interactions with the sample components. Straight alkyl chains including butyl-, octyl-, ether- and/or isopropyl-groups and aryl ligands including phenyl-groups. In the context of the present invention, the ligands of HIC media used include phenyl-, butyl-groups and/or polypropylene glycol (PPG)-groups. Preferred are phenyl- and butyl-groups. In general, more hydrophobic proteins to be purified require less hydrophobic ligands for a successful separation. Conversely, more hydrophilic samples require strongly hydrophobic ligands in order to achieve sufficient binding for subsequent separation. In the context of the present invention, the multispecific CrossMab antibody may have a lower hydrophobicity than the mispaired variant thereof. For example, a light-chain mispaired antibody of the present invention, wherein the VL domain of the unmodified light chain is combined with the VL domain of the domain-exchanged heavy chain may result in less tightly associated domains so that hydrophobic residues are exposed to a greater extent than in correctly paired multispecific CrossMab antibodies thereof. Hence, the hydrophobic residues of the heavy chain of the Fab region exposed to the light chain of an antibody have a higher accessibility in mispaired antibodies of the multispecific CrossMab antibody since While ligands contribute significantly to the degree of hydrophobicity of a HIC medium, the matrix can also influence the final selectivity of a HIC medium. Chromatography media for hydrophobic interaction are made from porous matrices. In one embodiment of the present invention, the matrix comprises a polymeric or an agarose based matrix. In a preferred embodiment of the present invention, the matrix comprises agarose. In a particularly preferred embodiment of the invention, the agarose comprises between 4% and 6% of the medium. An optimal balance between porosity of the matrix and particle size offers a large surface area covered by ligands and so ensures a high binding capacity. The most suitable matrix can be selected according to the degree of resolution, binding capacity and flow rates required. For example, gradient elution on Sepharose HP having an average particle size of 34 µm will give a high resolution. In addition, the particle size is a significant factor in resolution. The resolution of a HIC separation is a combination of the degree of separation between two peaks eluted from the column, the ability of the column to produce narrow, symmetrical peaks and, the amount of sample applied. In general, the smallest particle size will produce the narrowest peaks under the correct elution conditions. Although resolution in terms if efficiency can be improved by decreasing the particle size of a matrix, using smaller particles often creates an increase in back pressure so that flow rates need to be decreased, lengthening the run time. Hence, it is preferable to adjust the average particle size of the HIC medium with the requirements for the purification.

In one embodiment of the present invention, the particles of the matrix have an average size of about (i) about 50 µm or less, preferably about 45 µm or less, more preferably between about 34 µm and about 40 µm in diameter and said ligands are butyl groups;

(ii) about 35 µm to about 60 µm, preferably between about 35 µm and about 50 µm, more preferably between about 35 µm and about 45 µm, most preferably about 40 µm in diameter and said ligands are phenyl groups; or (iii) about 35 µm to about 100 µm, preferably between about 60 µm and about 70 µm, most preferably about 65 µm in diameter and said ligands are polypropylene glycol groups.

In a preferred embodiment of the present invention, the particles of the matrix have an average size of about (i) about 50 µm or less, preferably about 45 µm or less, more preferably between about 34 µm and about 40 µm in diameter and said ligands are butyl groups;

(ii) about 35 µm to about 60 µm, preferably between about 35 µm and about 50 µm, more preferably between about 35 µm and about 45 µm, most preferably about 40 µm in diameter and said ligands are phenyl groups.

Hence, butyl-based HIC media with average particle sizes of about 34 µm and of about 40 µm are particularly preferred herein. Also, phenyl-based HIC media with average particle sizes of about 40 µm are particularly preferred herein.

In the context of the present invention, it has been found that a multispecific CrossMab antibody can be separated from a mispaired variant thereof by a hydrophobic interaction chromatography (HIC) medium.

It is generally known in the art that changes in temperature may affect protein structure and solubility, and, consequently, the interaction with other hydrophobic surfaces, such as those in HIC media. Moreover, rapid changes in temperature, for example, removing packed columns from a cold-room and then applying buffer at room temperature, may cause air bubbles in the packing and affect the separation. In practice, this means that HIC separation at a constant temperature may improve reproducibility. In this context, the temperature should be maintained constant through all HIC separations as used in the methods of the present invention to ensure consistent, reproducible results.

HIC media which are particularly useful in the context of the present invention are listed in the Table 1. Comparative HIC media which are not used in the method according to the present invention are listed in Table 2.

Hence, in the context of the present invention, the following HIC media are particularly preferred:

(a) A HIC medium which has an average particle size of about 34 µm, which has butyl groups as ligands and which comprises a matrix of cross-linked agarose. Preferably, said medium has a ligand density of about 50 µmol/ml medium. Preferably said HIC medium has a binding capacity of about 39 mg BSA/ml medium. Most preferably said medium is "Butyl Sepharose HP" (GE Healthcare). Further specifications of this medium are listed in Table 1.

(b) A HIC medium which has an average particle size of about 40 µm, which has butyl groups as ligands and which comprises a matrix of cross-linked agarose. Preferably said HIC medium has a binding capacity of about 37 mg BSA/ml medium. Most preferably said medium is "Capto Butyl ImpRes" (GE Healthcare). Further specifications of this medium are listed in Table 1.

(c) A HIC medium which has an average particle size of about 40 µm, which has phenyl groups as ligands and which comprises a matrix of cross-linked agarose. Preferably, said medium has a ligand density of about 9 µmol/ml medium. Preferably said HIC medium has a binding capacity of about 19 mg BSA/ml medium. Most preferably said medium is "Capto Phenyl ImpRes" (GE Healthcare). Further specifications of this medium are listed in Table 1.

In the context of the particular bispecific tetravalent CrossMab anti-DR5/anti-FAP antibody mentioned above, these HIC media (a) to (c) are particularly preferred.

The present invention also relates to a pharmaceutical composition comprising
(a) a bispecific CrossMab antibody comprising
  (i) at least one antigen binding region specific for death receptor 5 (DR5), and
  (ii) at least one antigen binding region specific for Fibroblast Activation Protein (FAP),
  wherein the antigen binding region specific for DR5 comprises a variable heavy chain comprising the amino acid sequence of SEQ ID NO.: 7 of WO 2014/161845 A1 and a variable light chain comprising the amino acid sequence of SEQ ID NO.: 8 of WO 2014/161845 A1;
  and the antigen binding region specific for FAP comprises a heavy chain variable region comprising the amino acid sequence of SEQ ID NO.: 15 of WO 2014/161845 A1 and a light chain variable region comprising the amino acid sequence of SEQ ID NO.: 16 of WO 2014/161845 A1; and
(b) and less than 5% of mispaired variants thereof, preferably less than 2% of mispaired variants thereof, more preferably less than 1% of mispaired variants thereof.

In this context, said antibody may comprise two of each of said antigen binding region specific for DR5 and antigen binding region specific antigen binding region specific for FAP Said pharmaceutical composition may be used in the treatment of cancer, particularly, wherein the cancer is pancreatic cancer or colorectal carcinoma.

TABLE 1

HIC media according to the invention

| Medium | Manufacturer | Ligand | Average particle size | Ligand density/ ml gel | Binding capacity/ml medium (at 10% breakthrough) | Matrix |
|---|---|---|---|---|---|---|
| Butyl Sepharose HP | GE Healthcare | Butyl | 34 µm | 50 µmol | 39 mg BSA | cross-linked agarose (6%) |
| Capto Butyl ImpRes | GE Healthcare | Butyl | 40 µm | | 37 mg BSA | cross-linked agarose |
| Capto Phenyl ImpRes | GE Healthcare | Phenyl | 40 µm | 9 µmol | 19 mg BSA | cross-linked agarose |
| TOYOPEARL PPG-600M | Tosoh | PPG | 65 µm | | | cross-linked polymethacrylate |

TABLE 2

Comparative HIC media

| Medium | Manufacturer | Ligand | Average particle size | Ligand density/ ml gel | Binding capacity/ml medium (at 10% breakthrough) | Matrix |
|---|---|---|---|---|---|---|
| Phenyl Sepharose HP | GE Healthcare | Phenyl | 34 µm | 25 µmol | 45 mg α-chymotrypsinogen | cross-linked agarose |
| Phenyl Sepharose 6FF (Low Sub) | GE Healthcare | Phenyl | 90 µm | 25 µmol | | cross-linked agarose |
| Capto Phenyl (High Sub) | GE Healthcare | Phenyl | 75 µm | 27 µmol | 27 mg BSA | cross-linked agarose |
| Fractogel EMD Phenyl (S) | EMD Millipore | Phenyl | 30 µm | | | cross-linked polymethacrylate |
| TOYOPEARL Ether 650M | Tosoh | Ether | 65 µm | | | cross-linked polymethacrylate |
| TOYOPEARL Butyl 650C | Tosoh | Butyl | 100 µm | | | cross-linked polymethacrylate |
| TOYOPEARL Phenyl 650M | Tosoh | Phenyl | 65 µm | | | cross-linked polymethacrylate |
| TOYOPEARL Hexyl 650C | Tosoh | Hexyl | 100 µm | | | cross-linked polymethacrylate |
| TOYOPEARL SuperButyl 550C | Tosoh | Butyl | 100 µm | | | cross-linked polymethacrylate |

TABLE 2-continued

Comparative HIC media

| Medium | Manufacturer | Ligand | Average particle size | Ligand density/ml gel | Binding capacity/ml medium (at 10% break-through) | Matrix |
|---|---|---|---|---|---|---|
| TOYOPEARL Butyl 600M | Tosoh | Butyl | 65 µm | | | cross-linked polymethacrylate |
| TOYOPEARL Butyl 650M | Tosoh | Butyl | 65 µm | | | cross-linked polymethacrylate |
| TOYOPEARL Phenyl 600M | Tosoh | Phenyl | 65 µm | | | cross-linked polymethacrylate |
| Butyl Sepharose 4FF | GE Healthcare | Butyl | 90 µm | 40 µmol | | cross-linked agarose (4%) |

The disclosures of all patent and scientific literature cited herein are expressly incorporated in their entirety by reference.

EXAMPLES

The following are examples of methods and compositions of the invention. It is understood that various other embodiments may be practiced, given the general description provided above. Although the foregoing invention has been described in some detail by way of illustration and example for purposes of clarity of understanding, the descriptions and examples should not be construed as limiting the scope of the invention.

General Methods
Recombinant DNA Techniques

For the production of multispecific CrossMab antibodies, standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. In particular, the tetravalent, bispecific anti-DR5/anti-FAP antibodies, RO6874813-000 (DR5FAP) were produced according to WO 2014/161845 (see reference to the particular VH and VL chains indicated herein above) and tetravalent, bispecific anti-pTau-PS422 antibodies (2+2 format; anti-pTau/anti-transferrin rezeptor (TfR)) were produced.

Antibody Expression

Tetravalent, bispecific anti-DR5/anti-FAP bispecific antibodies and tetravalent, bispecific anti-pTau-PS422 antibodies were designed according to the CrossMab and the knob in hole (KiH) technology as described, e.g., in Schaefer et al, PNAS USA 108(2011), 11187-11192.

Exemplary Purification Strategy

1) Protein A Affinity Chromatography:

The solution comprising anti-DR5/anti-FAP bispecific antibodies and $LC_{DR5}$ mispaired variants thereof were purified from the sterile filtered culture supernatants by affinity chromatography using a Protein A—Sepharose column (MabSelectSure—Sepharose™ (GE Healthcare, Sweden).

2) Hydrophobic Interaction Chromatography:

The protein A eluate comprising anti-DR5/anti-FAP bispecific antibodies and $LC_{DR5}$ mispaired variants thereof were subjected to a HIC medium. Different HIC media were used in the following examples as shown in Table 1. For example, Butyl Sepharose HP is based on highly cross-linked, 34 µm agarose beads modified with aliphatic butyl groups via uncharged, chemically stable ether linkages. Capto Phenyl and Capto Butyl ImpRes media are based on a high-flow agarose matrix which allows for high flow velocities. A beadsize of 40 µm is employed for Capto Phenyl and Capto Butyl ImpRes media allowing for increased resolution compared to HIC media based on larger beadsize. The hydrophobicity characteristics of Butyl Sepharose HP, Capto Phenyl and Capto Butyl ImpRes media can be analyzed by a selectivity test using different model proteins, such as α-chymotrypsinogen or lysozyme. As provided by the data sheet of GE Healthcare Life Sciences (data file 29-0319-25 AB), the retention times for the model protein α-chymotrypsinogen using Butyl Sepharose HP and Capto Butyl ImpRes media were similar. Considering all three HIC media, the relative hydrophobicity compared to other HIC media determined by these retention times according to the data sheet of GE Healthcare Life Sciences (data file 29-0319-25 AB) was shown to be similar.

TABLE 1

Media characteristics of HIC media provided by GE Healthcare Life Sciences.

| HIC medium | Average size of particle [µM] | Ligand density [µmol/ml medium] | ligand | structure | Dynamic binding capacity (mg/mL) |
|---|---|---|---|---|---|
| ButylSepharose HP | 34 | 50 | Butyl | —O—$(CH_3)_2$—$CH_2$ | 39 |
| CaptoButyl ImPres | 40 | n.a. | Butyl | —O—$(CH_3)_2$—$CH_2$ | 37 |

TABLE 1-continued

Media characteristics of HIC media provided by GE Healthcare Life Sciences.

| HIC medium | Average size of particle [μM] | Ligand density [μmol/ml medium] | ligand | structure | Dynamic binding capacity (mg/mL) |
|---|---|---|---|---|---|
| CaptoPhenyl ImPres | 40 | appox. 9 | Phenyl | 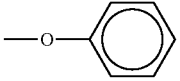 | 19 |
| CaptoButyl HighSub | 75 | approx. 53 | Butyl | —O—(CH$_3$)$_2$—CH$_2$ | n.a. |
| Toyo Ether-650M | 65 | n.a. | Ether | 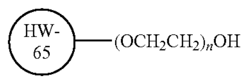 | n.a. |
| Toyo Butyl-650C | 100 | n.a. | Butyl | 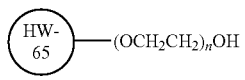 | n.a. |
| Toyo PPG-600M | 65 | n.a. | PPG | 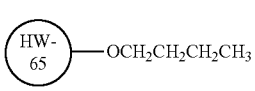 | n.a. |
| Toyo Phenyl-650M | 65 | n.a. | Phenyl | 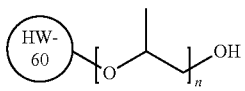 | n.a. |
| Toyo Superbutyl-550C | 100 | n.a. | Superbutyl | 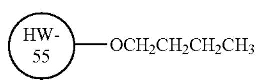 | n.a. |
| Toyo Butyl-600M | 65 | n.a. | Butyl | 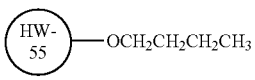 | n.a. |
| Hexyl-650C | 100 | n.a. | Hexyl | 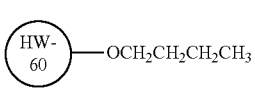 | n.a. |
| Phenyl-600M | 65 | n.a. | phenyl | 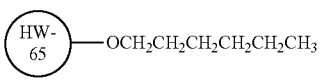 | n.a. |

*n.a. = not available

Analytical Strategy

Size-Exclusion Chromatography:

The TSKgel® G3000SW$_{xl}$ (Tosoh, Germany) was used as an analytical method for the characterization of the anti-DR5/anti-FAP antibodies and LC$_{DR5}$ mispaired variants thereof. Thereby, Table 2 shows parameters such as buffers, flow rates and load that may be applied in the context of the present invention:

TABLE 2

| SE-HPLC parameters. | |
|---|---|
| Column; ID × L, particle size | TSKgel ® G3000SW$_{xl}$; 7.8 mm × 300 mm; 5 μM |
| Buffer | 200 mM KPO$_4$, 250 mM KCl, pH 7.0 |
| Flow rate | 0.5 mL/min |
| Elution | isocratic |
| Pressure [p-max.] | 80 bar |
| Pressure [p-min.] | 5 bar |
| Load [μg] | 100 |

Hydrophobic Interaction Chromatography-High Performance Liquid Chromatography (HIC-HPLC):

The TSKgel® Ether-5PW was used to analyze the anti-DR5/anti-FAP antibodies and LC$_{DR5}$ mispaired variants thereof. Table 3 shows parameters such as buffers, gradients and load that may be applied in the context of the present invention:

TABLE 3

HIC-HPLC parameters.

| Column; ID × L, particle size | TSKgel ® Ether-5PW; 7.5 mm × 75 mm; 10 µM |
|---|---|
| Buffer-A | 25 mM NaO$_4$, 1.5M ammonium sulfate, pH 7.0 |
| Buffer-B | 25 mM NaO$_4$, pH 7.0 |
| Flow rate | 0.8 mL/min |
| Elution | Linear gradient 10%-70% B |
| Pressure [p-max.] | 20 bar |
| Load [µg] | 20 |

Structural Analysis

Size Exclusion Chromatography with Multi-Angle Static Light Scattering (SEC-MALS)

Size exclusion chromatography with multi-angle static light scattering (SEC-MALS) was used to measure masses of the anti-DR5/anti-FAP bispecific antibodies and LC$_{DR5}$ mispaired variants thereof.

SDS-Gel Capillary Electrophoresis (CE-SDS)

SDS-Gel Capillary Electrophoresis (CE-SDS) was used to determine the separation of the anti-DR5/anti-FAP antibodies and LC$_{DR5}$ mispaired variants thereof and/or of the anti-pTau/anti-TfR and LC$_{anti-TfR}$.

MS-Spectrometry:

The electrospray ionization mass spectrometry (ESI-MS) was used as another analytical method for the structural characterization of the anti-DR5/anti-FAP bispecific antibodies and LC$_{DR5}$ mispaired variants thereof. Table 4 shows parameters for sample treatment that may be applied in the context of the present invention:

TABLE 4

ESI-MS analytics MaXis UHR-TOF - Tandem mass spectrometer

| Device | MaXis UHR-TOF - Tandem mass spectrometer |
|---|---|
| protease | N-glucosidase F |
| Reducing agent | TCEP |
| buffer | 1 × PBS, pH 7.0 |
| Desalination column | Hi-Trap ® Desalting |

Example 1: Separation of Anti-DR5/Anti-FAP Antibodies from LC$_{DR5}$ Mispaired Variants Thereof Using Butyl Sepharose HP Anti-DR5/anti-FAP bispecific antibodies were expressed and purified from culture supernatant using Protein A affinity chromatography as described above and the solution comprising the anti-DR5/anti-FAP antibodies and LC$_{DR5}$ mispaired variants thereof were subjected to Butyl-Sepharose HP HIC medium with a negative ammonium sulfate gradient at pH5.5.

In detail, subsequent to the Protein A affinity purification as described above, protein A eluate comprising the anti-DR5/anti-FAP antibodies and LC$_{DR5}$ mispaired variants thereof were adjusted to 1 M ammonium sulfate with 3 M ammonium sulfate in 35 mM sodium acetate at pH 5.5. This solution was subjected to hydrophobic interaction chromatography (10×160 mm, CV=12.6 ml) according to the following procedure:

TABLE 5

Procedure of separating anti-DR5/anti-FAP antibodies from LC$_{DR5}$ mispaired variants thereof using Butyl Sepharose HP.

| Equilibration | 5 CV | 35 mM sodium acetate, 1M ammonium sulfate, pH 5.5 |
|---|---|---|
| Load | 16.7 mL | 10.0 mg/ml bed volume |
| Wash | 5 CV | 35 mM sodium acetate, 1M ammonium sulfate, pH 5.5 |
| Elution | 30 CV | linear gradient to 35 mM sodium acetate, pH 5.5 |
| | 5 CV | 35 mM sodium acetate, pH 5.5 |
| Cleaning 1 | 5 CV | Acetic acid, 20% ethanol pH 5.4 |

Figure 4:
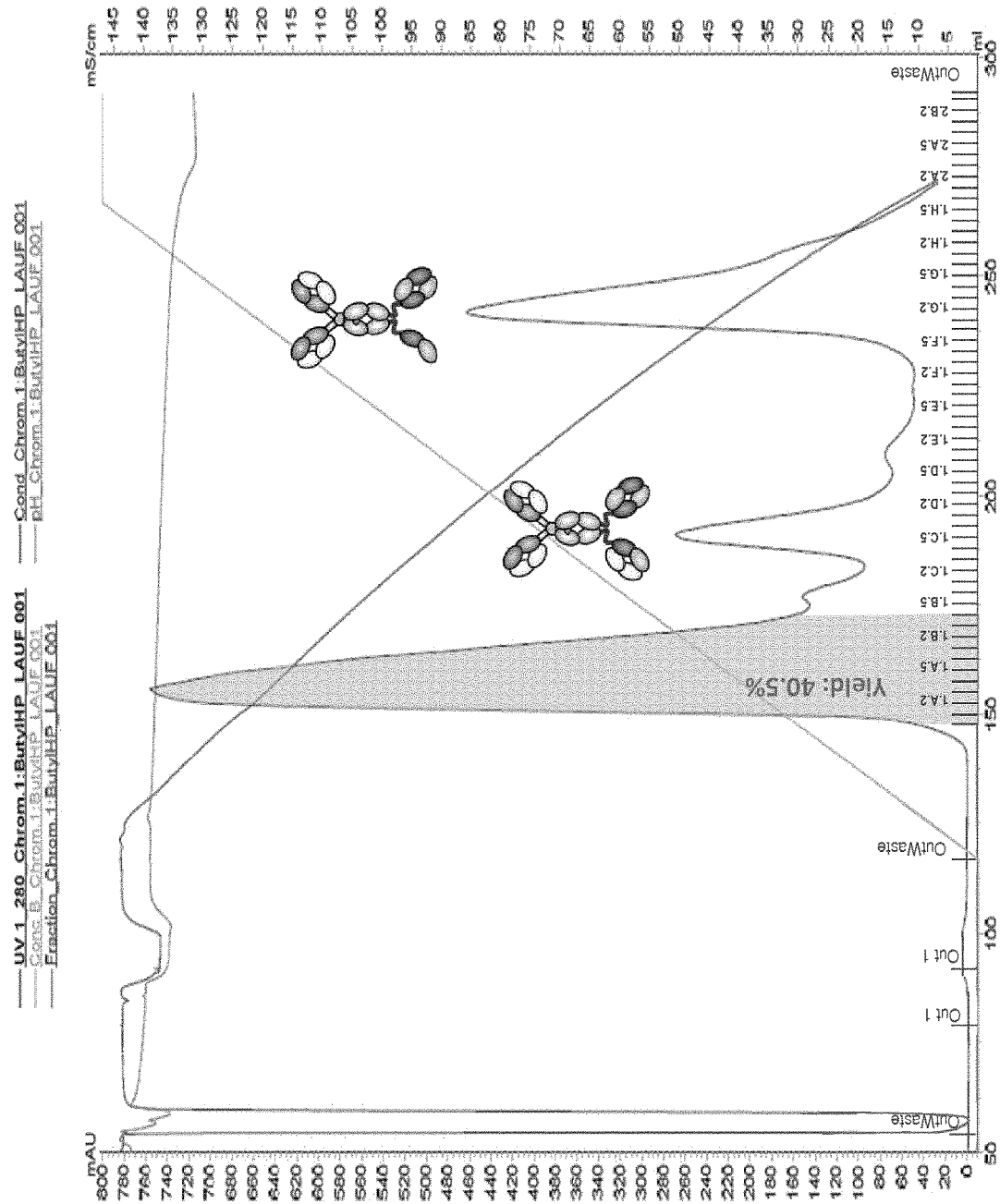
FIG. 4 A-C: Chromatogram of a HIC (A), SE-HPLC (B) and HI-HPLC (C). HIC was performed on a Butyl Sepharose HP medium with a linear, negative ammonium sulfate gradient sulfate in 35 mM sodium acetate at pH 5.5 (A). Peak 1, 2 and 3 refer to 1: anti-DR5/anti-FAP antibodies; 2: $LC_{DR5}$ mispaired variants thereof and 3: missing light-chain variants. The yield of the intact construct of the anti-DR5/anti-FAP antibodies is highlighted in peak 1. Fractions collected for the analysis with SE-HPLC (B) and HI-HPLC (C) are shown on the x-axis of FIG. 4 A. The intact product of the anti-DR5/anti-FAP antibodies is shown by the peak of the SE-HPLC (B) and HI-HPLC (C).
Figure 4:
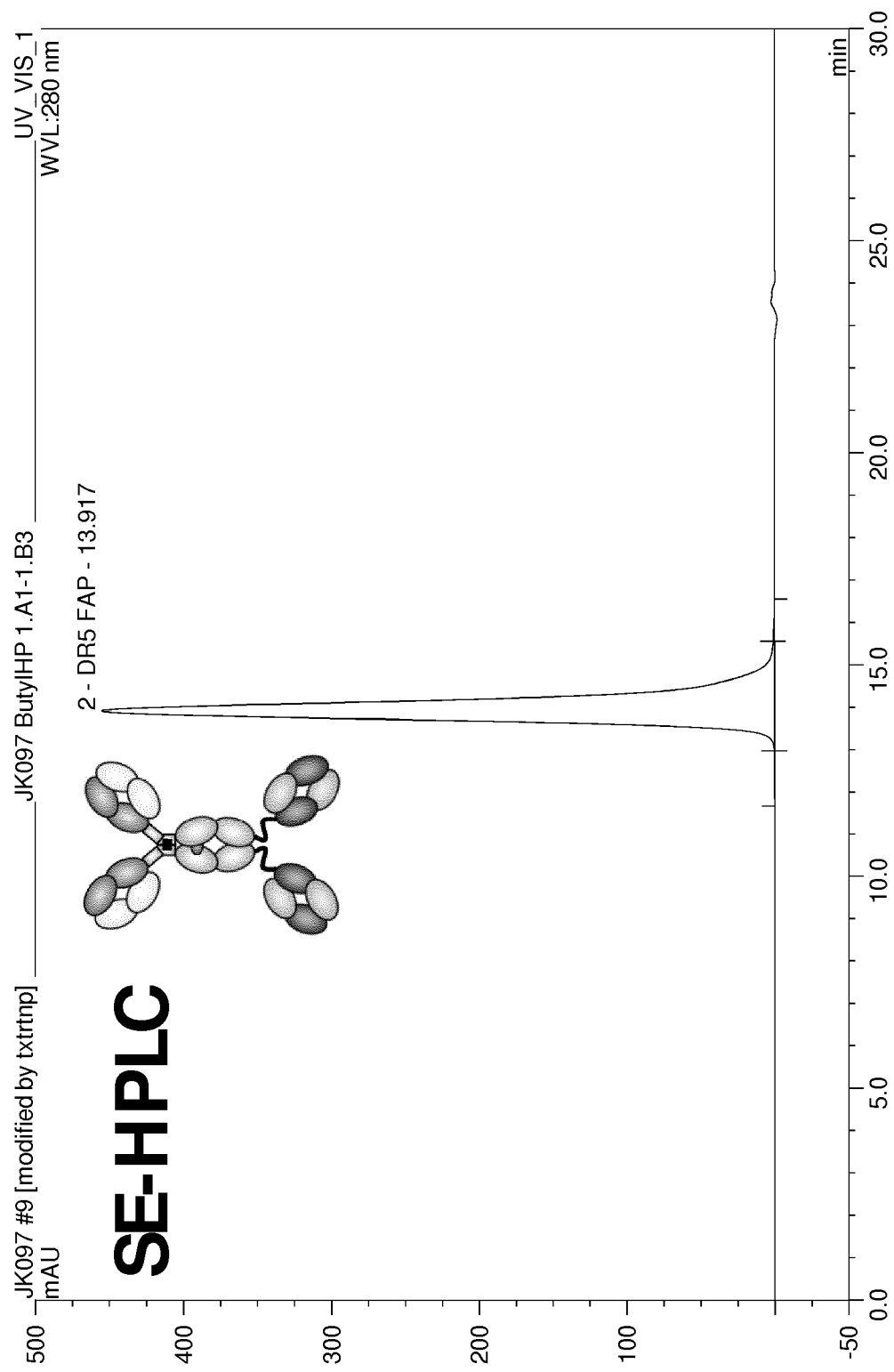
Figure 4:
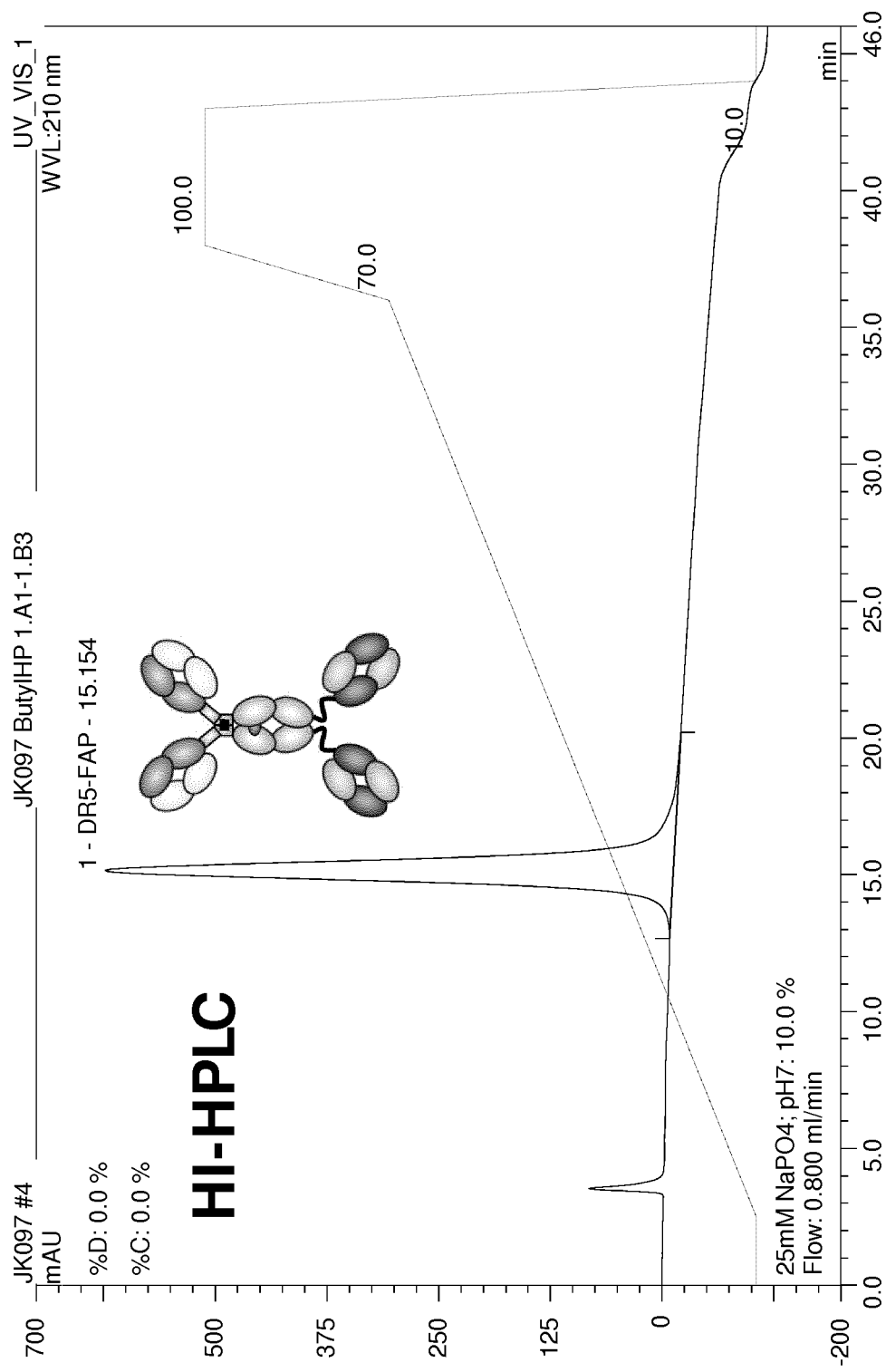
Figure 6A:
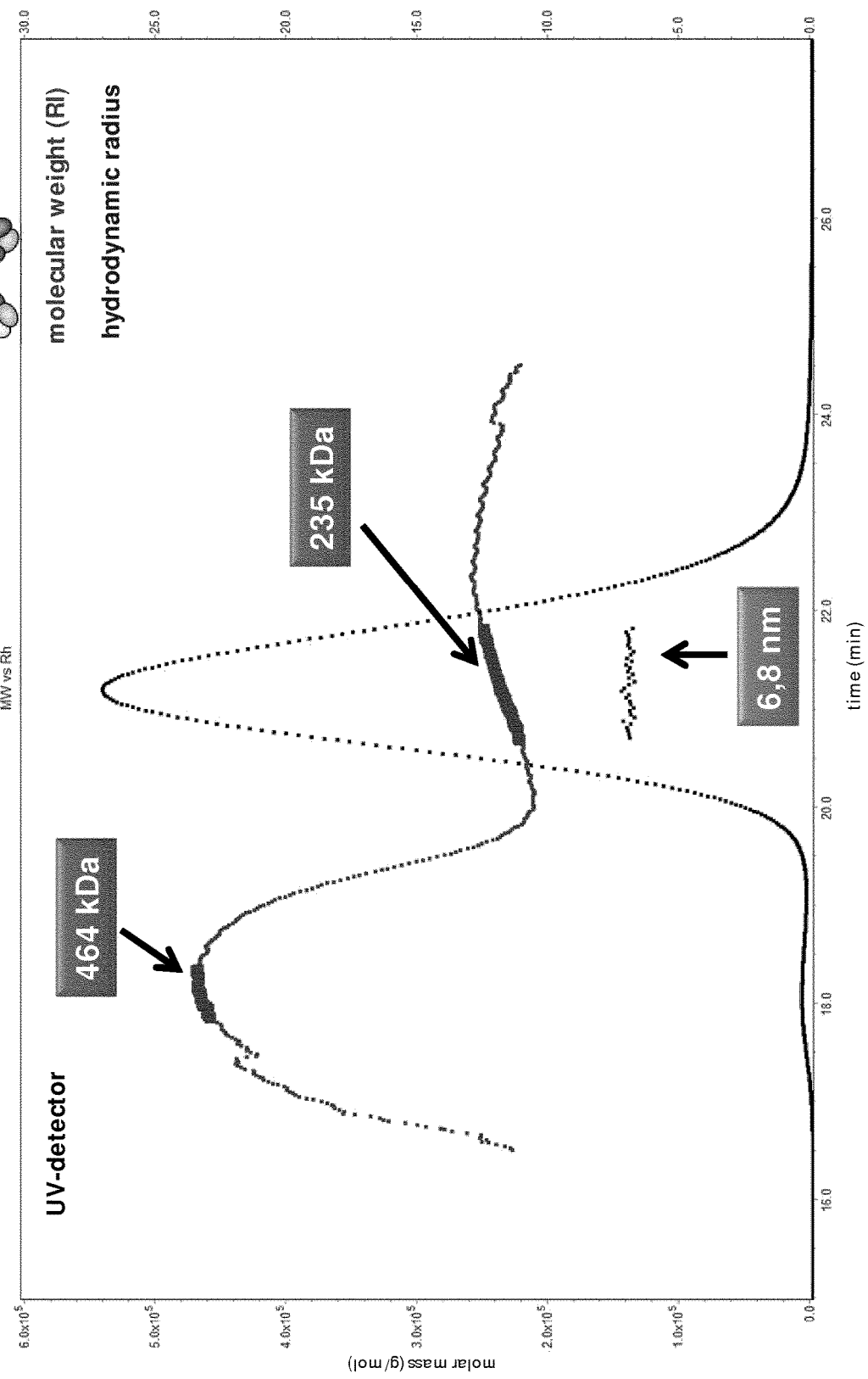
FIG. 6 A-B: SEC-MALS of TSKgel Ether-5PW pools of the $LC_{DR5}$ mispaired antibody variants and spectrogram of an ESI-MS of the $LC_{DR5}$ mispaired antibody variants of the anti-DR5/anti-FAP antibodies.
Figure 6:
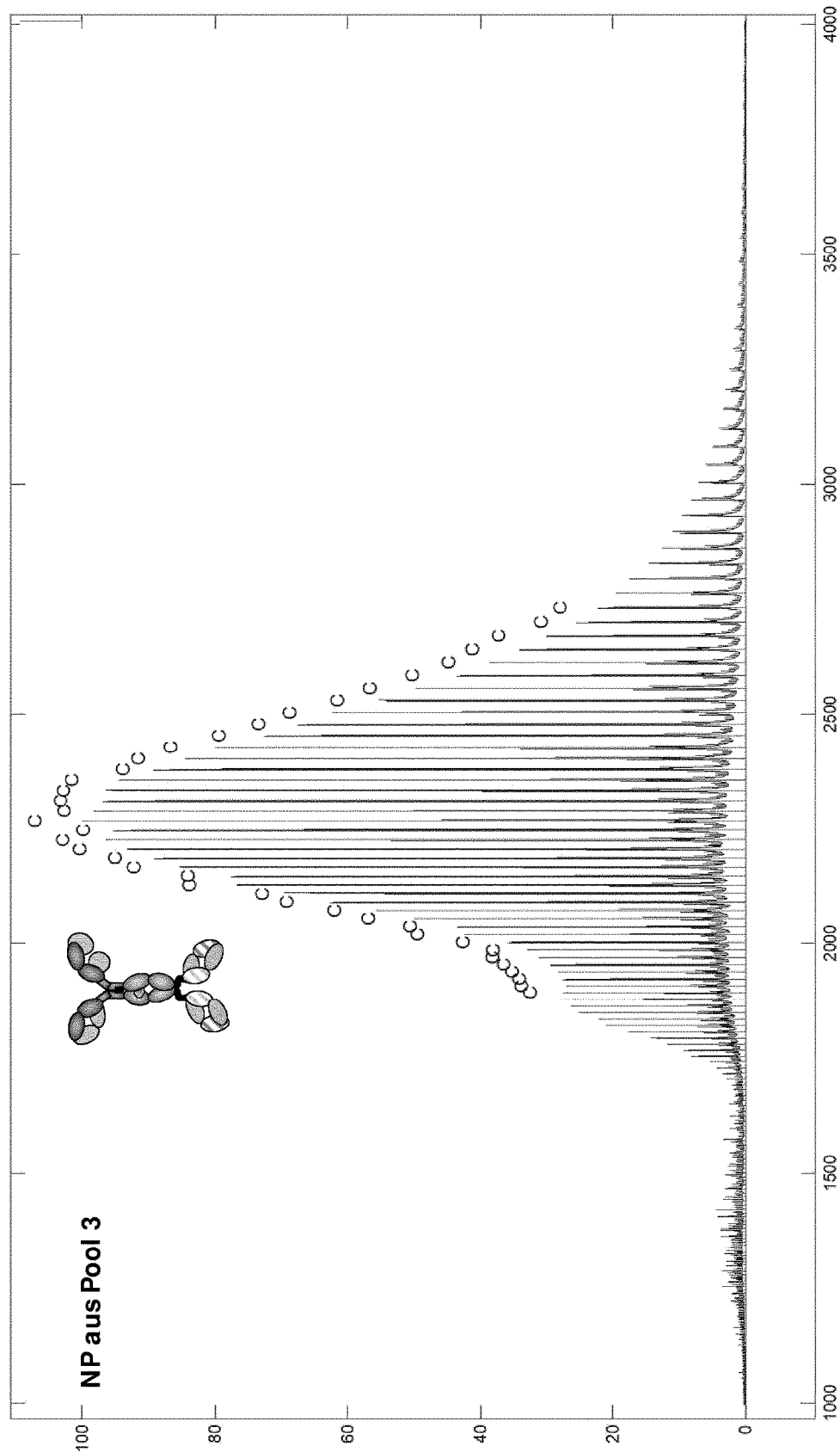

For analytical assessment, the eluate was fractionated by means of SE-HPLC and HIC-HPLC into peak 1, 2 and 3 pooled and characterized by analytical SEC-MALS and ESI-MS (FIG. 4 B-C; FIGS. 5, 6 A-B and 7 A-B). Structural analysis of the fractions shown in FIGS. 6 A and 4 A display the determination of the molecular weight via SEC-MALS. In comparison to the reference material with a molecular weight of 464 kDa, the lower molecular weight of 235 kDa would reflect the molecular weight of the LC$_{DR5}$ mispaired antibody variant (FIG. 6 A). Moreover, the molecular weight of 217 kDa compared to the reference molecular weight of 480 kDa would reflect molecular weight the light-chain missing antibody (FIG. 6 A). In combination with the results of the ESI-MS, the identification of these antibody variants could be confirmed (FIG. 6 B).

Contrary to the HIC separation described above, in the analytical HIC-HPLC, the anti-DR5/anti-FAP antibodies eluted after the LC$_{DR5}$ mispaired variants thereof (FIG. 5) owing to the HPLC medium used. In the HIC-HPLC, it could be confirmed by SEC-MALS and ESI-MS that peak 1 comprised the anti-DR5/anti-FAP antibodies and was clearly separated from peak 2 comprising LC$_{DR5}$ mispaired variants thereof visible by two distinct peaks in the elution profile of the HIC separation (FIG. 4 A). Furthermore, peak 3 was shown to comprise light-chain missing variants. Due to the mispaired light chain, the LC$_{DR5}$ mispaired variant possesses hydrophobic residues exposed to the surface of the antibody and thus, the LC$_{DR5}$ mispaired variant displayed a higher hydrophobicity than the anti-DR5/anti-FAP bispecific antibodies, wherein such hydrophobic residues are shielded by the correctly paired light chain. In this regard, the anti-DR5/anti-FAP bispecific antibodies eluted before the LC$_{DR5}$ mispaired variants thereof.

Structural analysis of the product pool of the SE-HPLC and HIC-HPLC comprising the anti-DR5/anti-FAP antibodies and the starting material comprising the protein A eluate was performed by SEC-MALS and ESI-MS (FIGS. 6 A-B and 7 A-B). When comparing the product pool and the starting material as shown in Table 6, the LC$_{DR5}$ mispaired variants were depleted in the product pool whereas 9% of such LC$_{DR5}$ mispaired variants remained in the starting material (Table 6). Other product-related byproducts, such as light-chain missing variants were reduced in the product pool compared to the starting material (Table 6). Furthermore, higher amounts of the anti-DR5/anti-FAP antibodies were identified in the product pool compared to the starting material (Table 6). Hence, the LC$_{DR5}$ mispaired antibody variants were depleted while the total amount of the desired product was increased and further product-related byproducts were reduced.

TABLE 6

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| | | Hydrophobic interaction HPLC | | |
|---|---|---|---|---|
| | Size Exclusion- HPLC Main [%] | anti-DR5/ anti-FAP bispecific antibodies [%] | $LC_{DR5}$ mispaired antibody variants [%] | product-related byproducts [%] |
| | Yield [%] | | | |
| Starting material | n. a. | 77.9 | 58.3 | 9.0 | 32.7 |
| Product pool | 43.3 | 91.3 | 97.3 | 0 | 2.7 |

Example 2: Separation of Anti-DR5/Anti-FAP Antibodies from $LC_{DR5}$ Mispaired Variants Thereof Using Capto Butyl ImpRes Anti-DR5/anti-FAP antibodies were expressed and purified as described in Example 1. The solution comprising the anti-DR5/anti-FAP antibodies and $LC_{DR5}$ mispaired variants thereof were subjected Capto Butyl Impres HIC medium with a negative ammonium sulfate gradient at pH5.5.

In detail, subsequent to the Protein A affinity purification as described above, protein A eluate comprising the anti-DR5/anti-FAP antibodies and $LC_{DR5}$ mispaired variants thereof were adjusted to 1 M ammonium sulfate with 3.5 M ammonium sulfate in 35 mM sodium acetate pH 5.5. This solution was subjected to hydrophobic interaction chromatography (11×206 mm, CV=19.6 ml) according to the following procedure:

TABLE 7

Procedure of separating anti-DR5/anti-FAP antibodies from $LC_{DR5}$ mispaired variants thereof using Capto Butyl ImpRes.

| Equilibration | 5 CV | 35 mM sodium acetate, 1M ammonium sulfate, pH 5.5 |
|---|---|---|
| Load | 72.6 mL | 24.4 mg/ml bed volume |
| Wash | 5 CV | 35 mM sodium acetate, 1M ammonium sulfate, pH 5.5 |
| Elution | 30 CV | linear gradient to 35 mM sodium acetate, pH 5.5 |
| | 5 CV | 35 mM sodium acetate, pH 5.5 |
| Cleaning 1 | 5 CV | 1M sodium acetate, 20% ethanol pH 5.4 |
| Rinse | 3 CV | 35 mM sodium acetate, pH 5.5 |
| Cleaning 2 | 3 CV | 0.1M sodium hydroxide |

Figure 7:
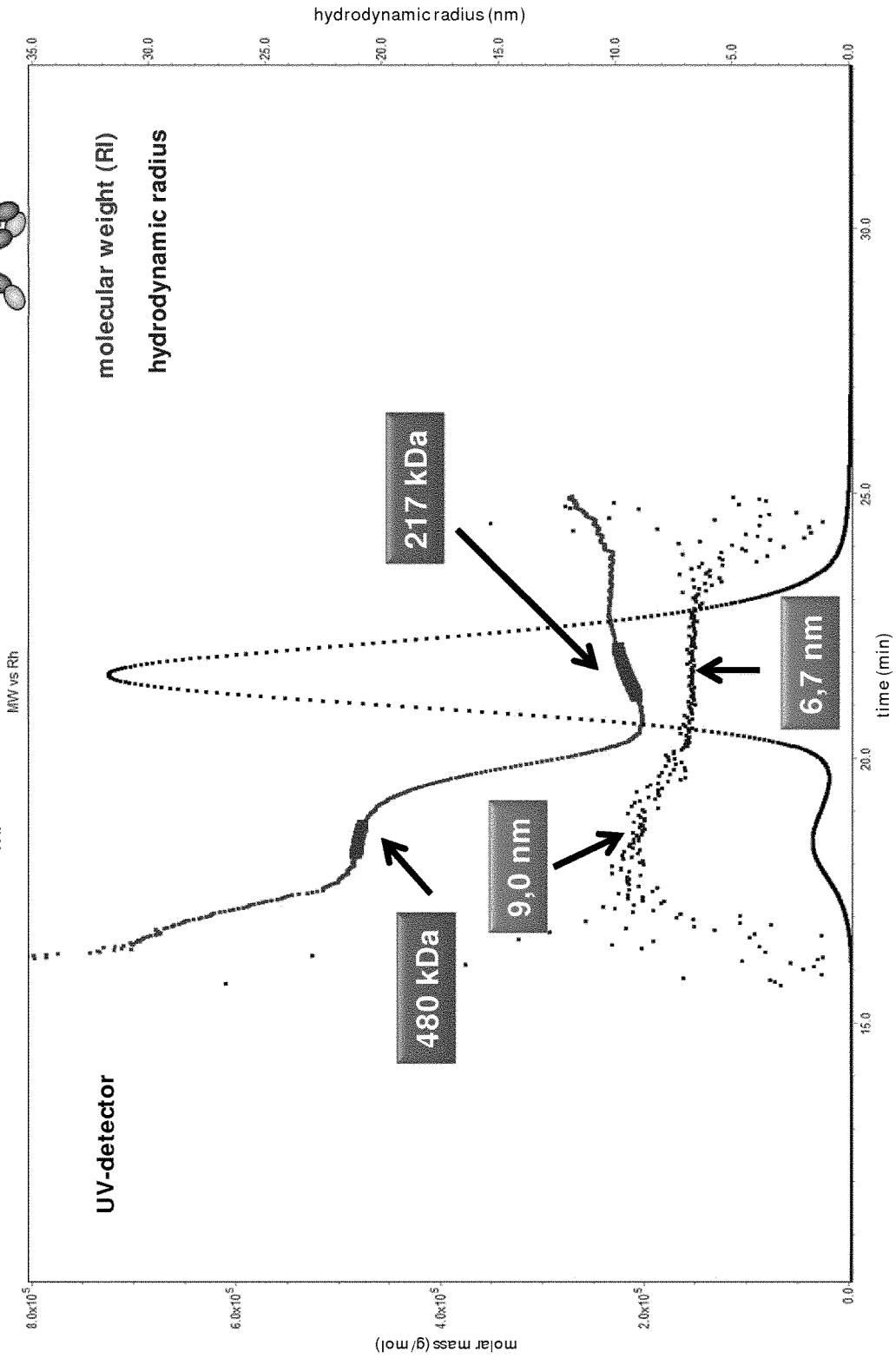
FIG. 7 A-B: SEC-MALS of TSKgel Ether-5PW pools of the missing light-chain antibody variants and spectrogram of an ESI-MS of the missing light-chain antibody variants of the anti-DR5/anti-FAP antibodies.
Figure 7:
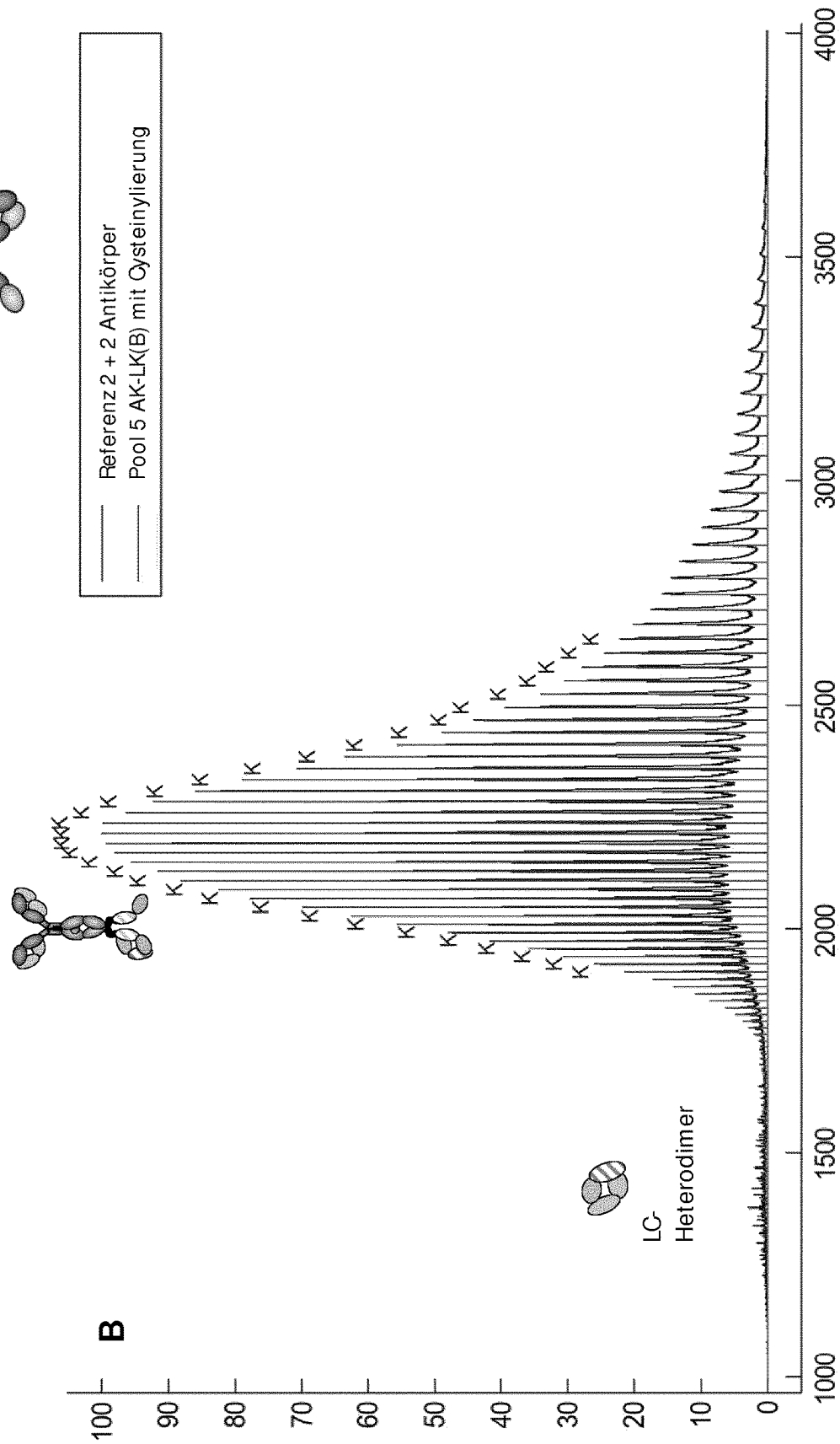
Figure 8:
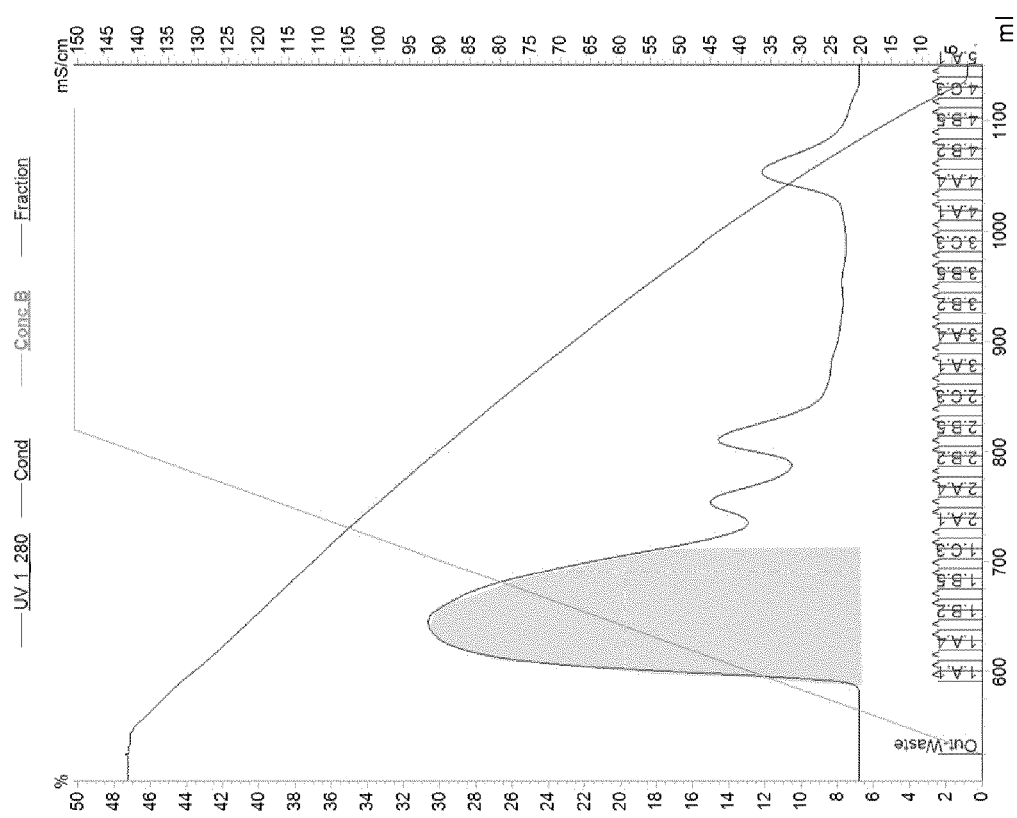
FIG. 8: Chromatogram of a HIC using Capto Butyl ImpRes HIC medium with a linear, negative ammonium sulfate gradient sulfate in 35 mM sodium acetate at pH 5.5. Fractions collected for the analysis with SE-HPLC (B) and HI-HPLC (C) are shown on the x-axis.
Figure 9:
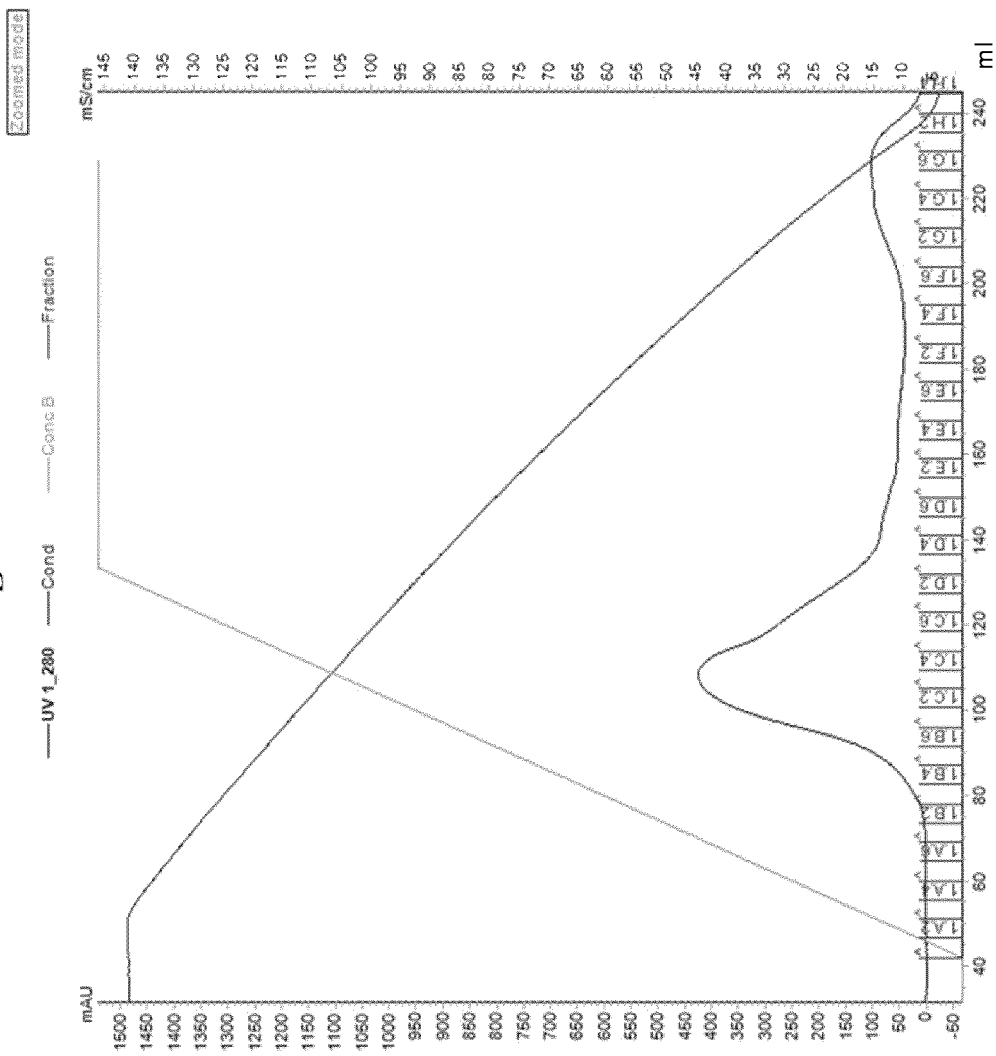
FIG. 9 A-B: Chromatogram of a HIC using Capto Butyl HIC medium (A) and Capto Phenyl ImpRes HIC medium (B) with a linear, negative ammonium sulfate gradient sulfate in 35 mM sodium acetate at pH 5.5. Fractions collected for the analysis with SE-HPLC (B) and HI-HPLC (C) are shown on the x-axis.
Figure 9:
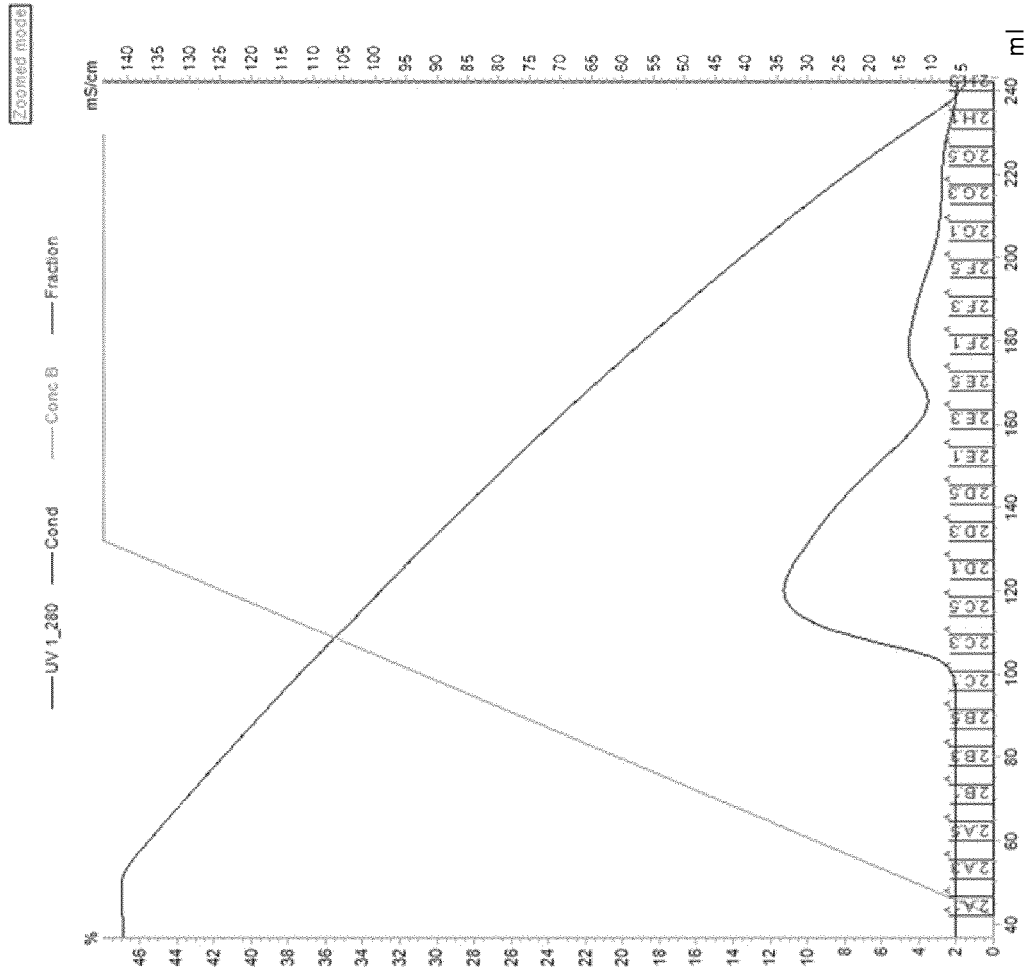

As in example 1, the eluate was fractionated by means of SE-HPLC and HIC-HPLC into peak 1, 2 and 3 pooled and characterized by analytical SEC-MALS and ESI-MS (FIGS. 7, 8 and 9 A-B). In the HIC-HPLC, it could be shown that the anti-DR5/anti-FAP antibodies were clearly separated from $LC_{DR5}$ mispaired variants thereof visible by a distinct peak in the elution profile of the HIC separation (FIG. 8).

As in example 1, structural analysis of the product pool of the SE-HPLC and HIC-HPLC comprising the anti-DR5/anti-FAP antibodies and the starting material comprising the protein A eluate was performed by SEC-MALS and ESI-MS. When comparing the starting material of the protein A eluate and the product pool as shown in Table 8, the $LC_{DR5}$ mispaired variants were depleted in the product pool whereas 6.7% of such $LC_{DR5}$ mispaired variants remained in the starting material. Other product-related byproducts, such as light-chain missing variants, were also depleted in the product pool compared to the starting material (23.5%) (Table 8). Furthermore, 100% of the anti-DR5/anti-FAP antibodies were identified in the product pool compared to the starting material, wherein 69.8% of the anti-DR5/anti-FAP antibodies were identified (Table 8). Hence, the $LC_{DR5}$ mispaired antibody variants and further product-related byproducts were depleted while the total amount of the desired product was maintained.

TABLE 8

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| | | Hydrophobic interaction HPLC | | |
|---|---|---|---|---|
| | Size Exclusion- HPLC Main [%] | anti-DR5/anti-FAP bispecific antibodies [%] | $LC_{DR5}$ mispaired antibody variants [%] | product-related byproducts [%] |
| | Yield [%] | | | |
| Starting material | n.a. | n.d. | 69.8 | 6.7 | 23.5 |
| Product pool | 62.3 | 100 | 100 | 0 | 0 |

Example 3: Separation of Anti-DR5/Anti-FAP Antibodies from $LC_{DR5}$ Mispaired Variants Thereof Using Capto Butyl and Capto Phenyl ImpRes Anti-DR5/anti-FAP antibodies were expressed and purified as described in Example 1. The solution comprising the anti-DR5/anti-FAP antibodies and $LC_{DR5}$ mispaired variants thereof were subjected to Capto Butyl HIC medium or Capto Phenyl ImpRes HIC medium with a negative ammonium sulfate gradient at pH5.5.

In detail, subsequent to the Protein A affinity purification as described above, protein A eluate comprising the anti-DR5/anti-FAP antibodies and $LC_{DR5}$ mispaired variants thereof was adjusted to 1.5 M ammonium sulfate with 3.5 M ammonium sulfate in 35 mM sodium acetate at pH 5.5. This solution was subjected to hydrophobic interaction chromatography (8×100 mm, CV=4.7 ml) according to the following procedure:

TABLE 9

Procedure of separating anti-DR5/anti-FAP antibodies from $LC_{DR5}$ mispaired variants thereof using Capto Butyl and Capto Phenyl ImpRes.

| Equilibration | 10 CV | 35 mM sodium acetate, 1.5M ammonium sulfate, pH 5.5 |
|---|---|---|
| Load | 5.0 mL | 19.6 mg/ml bed volume |
| Wash | 5 CV | 35 mM sodium acetate, 1.5M ammonium sulfate, pH 5.5 |
| Elution | 40 CV | linear gradient to 35 mM sodium acetate, pH 5.5 |
| | 5 CV | 35 mM sodium acetate, pH 5.5 |
| Cleaning 1 | 3 CV | 0.1M sodium hydroxide |
| Cleaning 2 | 3 CV | 1M Acetic acid, 20% ethanol |

As in example 1, the eluate was fractionated by means of SE-HPLC and HIC-HPLC into fractions as shown in FIGS. 9 A and B and characterized by analytical SEC-MALS and ESI-MS. In the HIC-HPLC of the HIC separation using Capto Phenyl ImpRes, it could be shown that the anti-DR5/anti-FAP antibodies were separated from $LC_{DR5}$ mispaired variants thereof visible two peaks in the elution profile of the HIC separation (FIG. 9 B). However, in the HIC-HPLC of the HIC separation using Capto Butyl, only one main peak was visible and thus the anti-DR5/anti-FAP antibodies were not visible separated from $LC_{DR5}$ mispaired variants thereof (FIG. 9 A).

Figure 10:
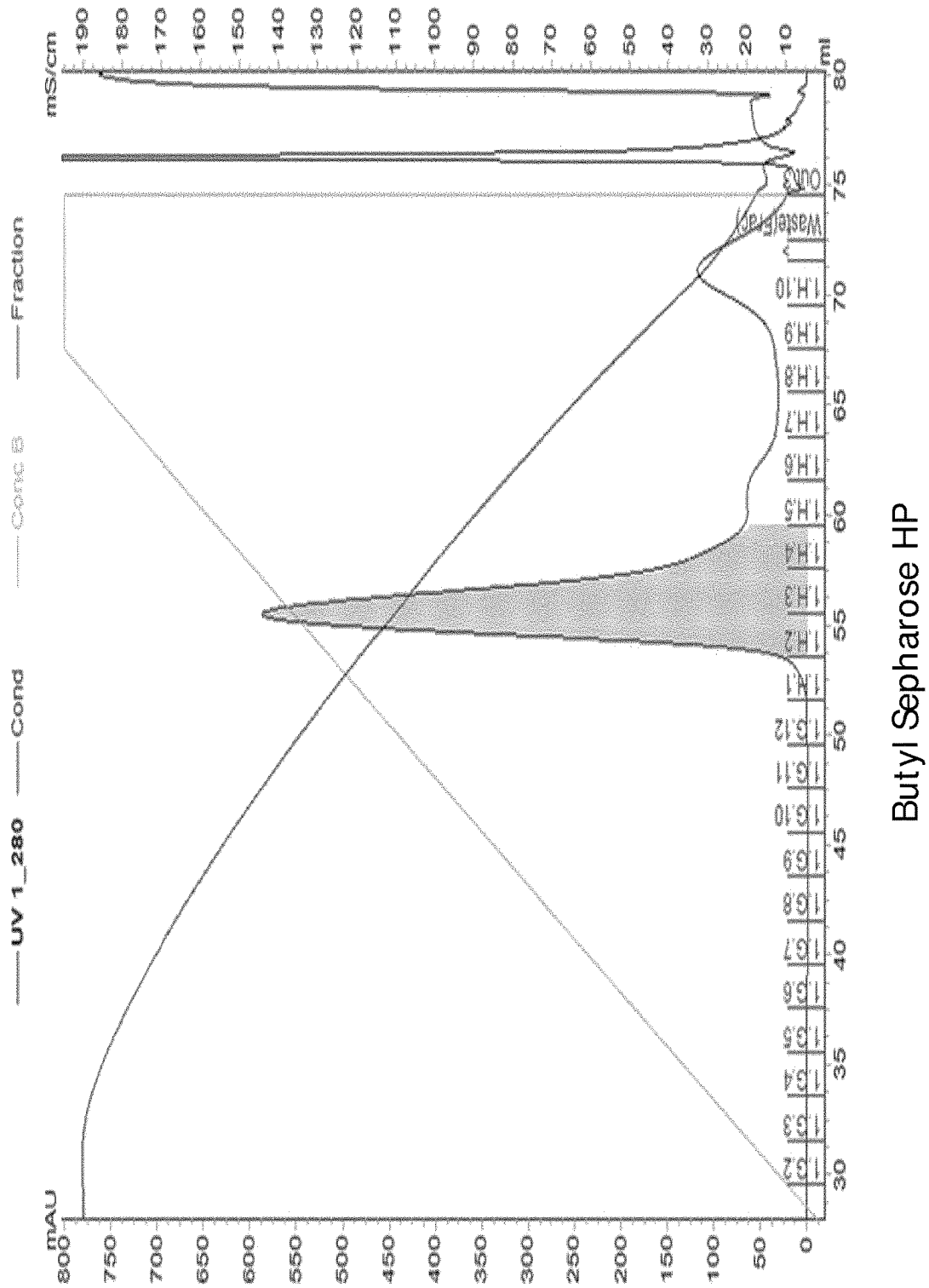
FIG. 10 A-B: Chromatogram of a HIC using Butyl Sepharose HP (A) and Toyopearl PPG 600M (B) with a linear, negative ammonium sulfate gradient sulfate in 35 mM sodium acetate at pH 5.5. Fractions collected for the analysis with SE-HPLC (B) and HI-HPLC (C) are shown on the x-axis.
Figure 10:
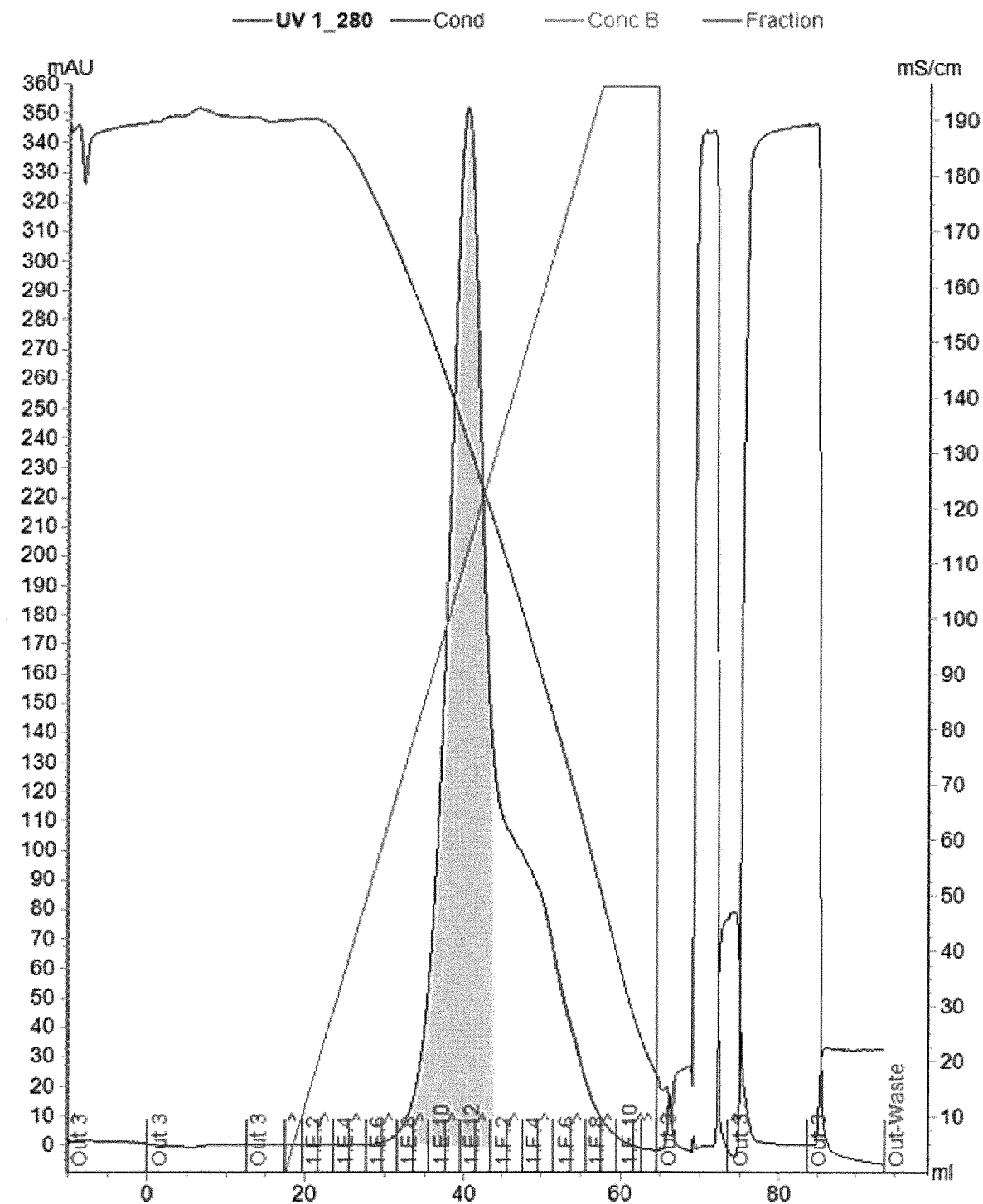

Structural analysis of the fractions of the SE-HPLC and HIC-HPLC of the Capto Phenyl ImpRes and the Capto Butyl HIC separation as shown in FIGS. 10 A and B and the starting material comprising the protein A eluate were performed by SEC-MALS and ESI-MS. When comparing the starting material of the protein A eluate and the product pool of the Capto Phenyl ImpRes HIC and Capto Butyl HIC as shown in Table 10 and Table 11, the $LC_{DR5}$ mispaired variants were depleted in some of the fractions, wherein the anti-DR5/anti-FAP bispecific antibodies were present in high yield and the product-related byproducts were significantly reduced in such fractions depleted of $LC_{DR5}$ mispaired variants.

TABLE 10

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| Capto Phenyl ImpRes | Size Exclusion-HPLC Main [%] | Hydrophobic interaction HPLC | | |
| --- | --- | --- | --- | --- |
| | | anti-DR5/anti-FAP bispecific antibodies [%] | $LC_{DR5}$ mispaired antibody variants [%] | product-related byproducts [%] |
| Starting material | 79.2 | 55.9 | 3.0 | 41.1 |
| Fraction 2.C.2 | 61.0 | 62.5 | 33.9 | 3.6 |
| Fraction 2.C.3 | 87.4 | 87.5 | 6.5 | 6.0 |
| Fraction 2.C.4 | 94.7 | 93.1 | 1.1 | 5.8 |
| Fraction 2.C.5 | 97.5 | 94.6 | 0.8 | 4.6 |
| Fraction 2.C.6 | 97.5 | 95.9 | 0.4 | 3.7 |
| Fraction 2.D.1 | 98.0 | 96.5 | 0 | 3.5 |
| Fraction 2.D.2 | 98.1 | 96.7 | 0 | 3.3 |
| Fraction 2.D.3 | 97.9 | 97.0 | 0 | 3.0 |
| Fraction 2.D.4 | 98.5 | 96.3 | 0 | 3.7 |
| Fraction 2.D.5 | 98.1 | 96.2 | 0 | 3.8 |
| Fraction 2.D.6 | 98.1 | 92.9 | 1.9 | 5.2 |
| Fraction 2.E.1 | 97.8 | 87.6 | 6.4 | 6.0 |
| Fraction 2.E.2 | 97.4 | 69.1 | 21.1 | 9.8 |
| Fraction 2.E.3 | 94.8 | 57.3 | 23.3 | 19.4 |
| Fraction 2.E.4 | 83.3 | 45.7 | 17.9 | 36.4 |
| Fraction 2.E.5 | 61.7 | 30.3 | 12.9 | 56.8 |
| Fraction 2.E.6 | 53.0 | 24.8 | 9.3 | 65.9 |

TABLE 11

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| Capto Phenyl | Size Exclusion-HPLC Main [%] | Hydrophobic interaction HPLC | | |
| --- | --- | --- | --- | --- |
| | | anti-DR5/anti-FAP bispecific antibodies [%] | $LC_{DR5}$ mispaired antibody variants [%] | product-related byproducts [%] |
| Starting material | 79.2 | 55.9 | 3.0 | 41.1 |
| Fraction 1.B.2 | 92.2 | 86.1 | 8.9 | 5.0 |
| Fraction 1.B.3 | 95.2 | 94.6 | 2.4 | 3.0 |

TABLE 11-continued

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| Capto Phenyl | Size Exclusion-HPLC Main [%] | Hydrophobic interaction HPLC | | |
| --- | --- | --- | --- | --- |
| | | anti-DR5/anti-FAP bispecific antibodies [%] | $LC_{DR5}$ mispaired antibody variants [%] | product-related byproducts [%] |
| Fraction 1.B.4 | 95.6 | 74.0 | 23.2 | 2.8 |
| Fraction 1.B.5 | 97.8 | 86.2 | 10.4 | 3.4 |
| Fraction 1.B.6 | 98.3 | 96.7 | 1.1 | 2.2 |
| Fraction 1.C.1 | 98.3 | 97.5 | 0 | 2.5 |
| Fraction 1.C.2 | 98.3 | 96.7 | 0 | 3.3 |
| Fraction 1.C.3 | 97.9 | 95.9 | 0 | 4.1 |
| Fraction 1.C.4 | 97.5 | 95.1 | 0 | 4.9 |
| Fraction 1.C.5 | 96.8 | 92.5 | 0 | 7.5 |
| Fraction 1.C.6 | 95.8 | 91.1 | 0 | 8.9 |
| Fraction 1.D.1 | 93.2 | 86.1 | 0 | 13.9 |
| Fraction 1.D.2 | 88.2 | 74.4 | 3.2 | 22.4 |
| Fraction 1.D.3 | 78.9 | 59.1 | 7.4 | 33.5 |
| Fraction 1.D.4 | 69.0 | 41.6 | 11.6 | 46.8 |
| Fraction 1.D.5 | 63.2 | 30.7 | 10.2 | 59.1 |
| Fraction 1.D.6 | 66.1 | 23.2 | 11.3 | 65.5 |

Example 4: Separation of Anti-DR5/Anti-FAP Antibodies from $LC_{DR5}$ Mispaired Variants Thereof Using Toyopearl Hexyl 650 c Anti-DR5/anti-FAP antibodies were expressed and purified as described in Example 1. The solution comprising the anti-DR5/anti-FAP antibodies and $LC_{DR5}$ mispaired variants thereof were subjected to a HIC medium using Capto Butyl and Capto Phenyl Impres with a negative ammonium sulfate gradient at pH5.5.

In detail, subsequent to the Protein A affinity purification as described above, protein A eluate comprising the anti-DR5/anti-FAP antibodies and $LC_{DR5}$ mispaired variants thereof has been adjusted to 1.5 M ammonium sulfate with 3.5 M ammonium sulfate in 35 mM sodium acetate at pH 5.5. This solution was subjected to hydrophobic interaction chromatography (8×20 mm, CV=1.0 ml) according to the following procedure:

TABLE 12

Procedure of separating anti-DR5/anti-FAP antibodies from $LC_{DR5}$ mispaired variants thereof using Toyopearl Hexyl 650 c.

| Equilibration | 10 CV | 35 mM sodium acetate, 1.5M ammonium sulfate, pH 5.5 |
| --- | --- | --- |
| Load | 5.0 mL | 19.6 mg/ml bed volume |
| Wash | 5 CV | 35 mM sodium acetate, 1.5M ammonium sulfate, pH 5.5 |
| Elution | 40 CV | linear gradient to 35 mM sodium acetate, pH 5.5 |
| | 5 CV | 35 mM sodium acetate, pH 5.5 |
| Cleaning 1 | 3 CV | 0.1M sodium hydroxide |
| Cleaning 2 | 3 CV | 1M Acetic acid, 20% ethanol |

The eluate has been fractionated and the product pools have analyzed by means of SE-HPLC and a HIC-HPLC. Toyopearl Hexyl 650 c showed breakthrough during load and post gradient elution indicating low binding capacity and too high hydrophobicity. Thus, when using Toyopearl Hexyl 650 c, the anti-DR5/anti-FAP antibodies were not visible separated from $LC_{DR5}$ mispaired variants thereof.

Example 5: Separation of Anti-DR5/Anti-FAP Antibodies from $LC_{DR5}$ Mispaired Variants Thereof Using Butyl Sepharose HP and Toyopearl PPG 600 M Anti-DR5/anti-FAP antibodies were expressed and purified as described in Example 1. The solution comprising the anti-DR5/anti-FAP antibodies and $LC_{DR5}$ mispaired variants thereof were subjected to a HIC medium using Butyl Sepharose HP or Toyopearl PPG 600 M with a negative ammonium sulfate gradient at pH5.5.

In detail, subsequent to the Protein A affinity purification as described above, protein A eluate comprising the anti-DR5/anti-FAP antibodies and $LC_{DR5}$ mispaired variants thereof has been adjusted to 1.5 M ammonium sulfate with 3.5 M ammonium sulfate in 35 mM sodium acetate at pH 5.5. This solution was subjected to hydrophobic interaction chromatography (8×20 mm, CV=1.0 ml) according to the following procedure:

TABLE 13

Procedure of separating anti-DR5/anti-FAP antibodies from $LC_{DR5}$ mispaired variants thereof using Butyl Sepharose HP or Toyopearl PPG 600 M.

| | | |
|---|---|---|
| Equilibration | 10 CV | 35 mM sodium acetate, 1.5M ammonium sulfate, pH 5.5 |
| Load | 2.5 mL | 9.8 mg/ml bed volume |
| Wash | 5 CV | 35 mM sodium acetate, 1.5M ammonium sulfate, pH 5.5 |
| Elution | 40 CV | linear gradient to 35 mM sodium acetate, pH 5.5 |
| | 5 CV | 35 mM sodium acetate, pH 5.5 |
| Cleaning 1 | 3 CV | 0.1M sodium hydroxide |
| Cleaning 2 | 3 CV | 1M Acetic acid, 20% ethanol |

The eluate has been fractionated and the product pools have analyzed by means of SE-HPLC and a HIC-HPLC (FIG. 10 A-B). Structural analysis of the total pool volume of the SE-HPLC and HIC-HPLC of the Butyl Sepharose HP and Toyopearl PPG 600 M HIC separation and the starting material comprising the protein A eluate were performed by SEC-MALS and ESI-MS. When comparing the starting material of the protein A eluate and the total pool volume of the SE-HPLC and the HIC-HPLC of the Butyl Sepharose HP HIC separation as shown in Table 14 the $LC_{DR5}$ mispaired variants in the pool were reduced, whereas in the total pool volume of the SE-HPLC and the HIC-HPLC of the Toyopearl PPG 600 M HIC separation the $LC_{DR5}$ mispaired variants in the pool were slightly reduced.

TABLE 14

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| | Yield [%] | Volume [CV] | SE-HPLC [%] |
|---|---|---|---|
| Starting material | n.a. | n.a. | 76.0 |
| Butyl HP pool | 57.7 | 6 | 89.5 |
| PPG 600M pool | 66.8 | 10 | 86.3 |

TABLE 14-continued

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| | Hydrophobic interaction HPLC | | |
|---|---|---|---|
| | anti-DR5/anti-FAP bispecific antibodies [%] | $LC_{DR5}$ mispaired antibody variants [%] | product-related byproducts [%] |
| Starting material | 53.9 | 6.8 | 39.3 |
| Butyl HP pool | 87.0 | 1.0 | 12.0 |
| PPG 600M pool | 80.9 | 3.6 | 15.5 |

Figure 11:
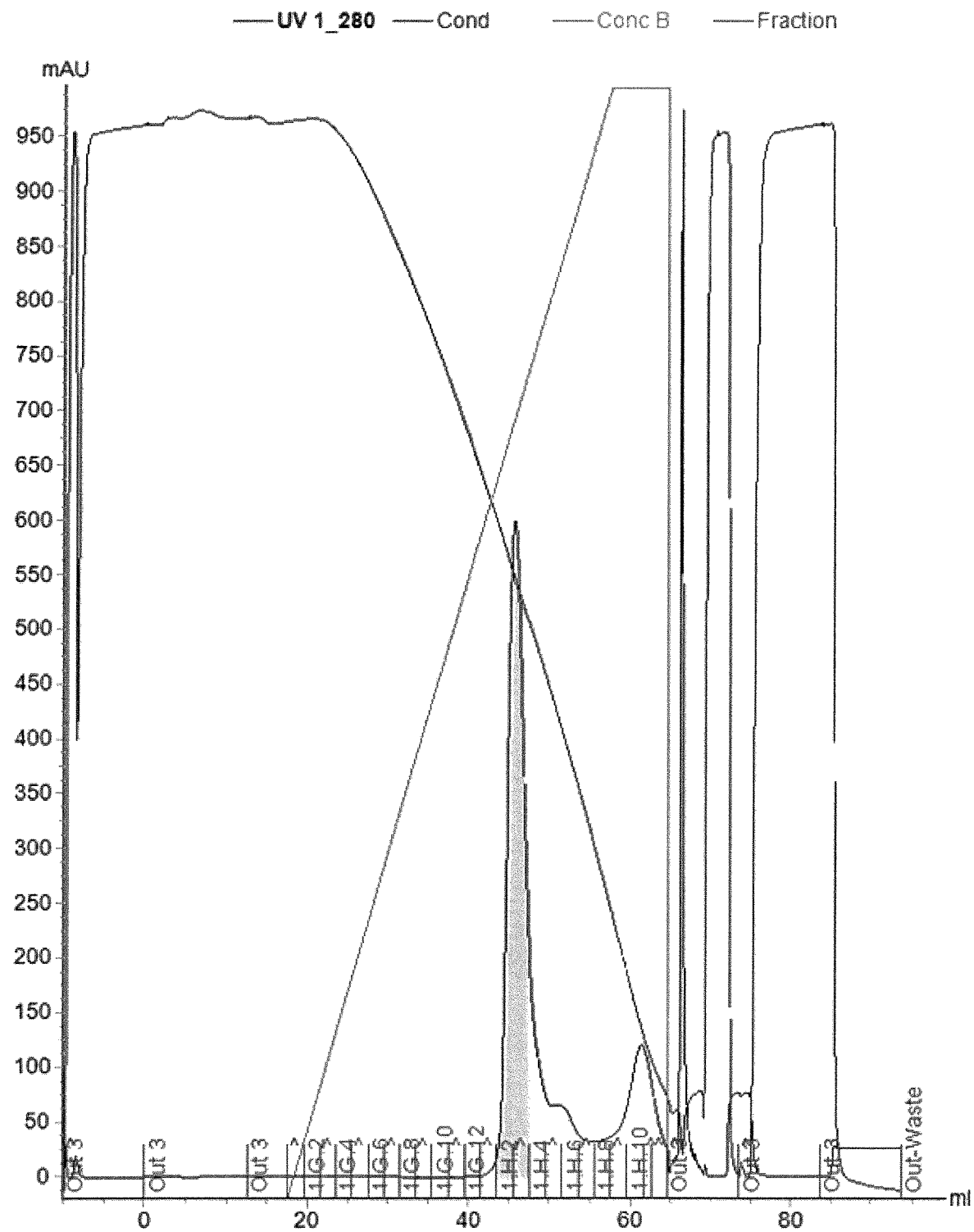
FIG. 11 A-B: Chromatogram of a HIC using Butyl Sepharose HP HIC medium (A) and Toyopearl Butyl 650C HIC medium (B) with a linear, negative ammonium sulfate gradient in 35 mM sodium acetate at pH 5.5. Fractions collected for the analysis with SE-HPLC (B) and HI-HPLC (C) are shown on the x-axis.
Figure 11:
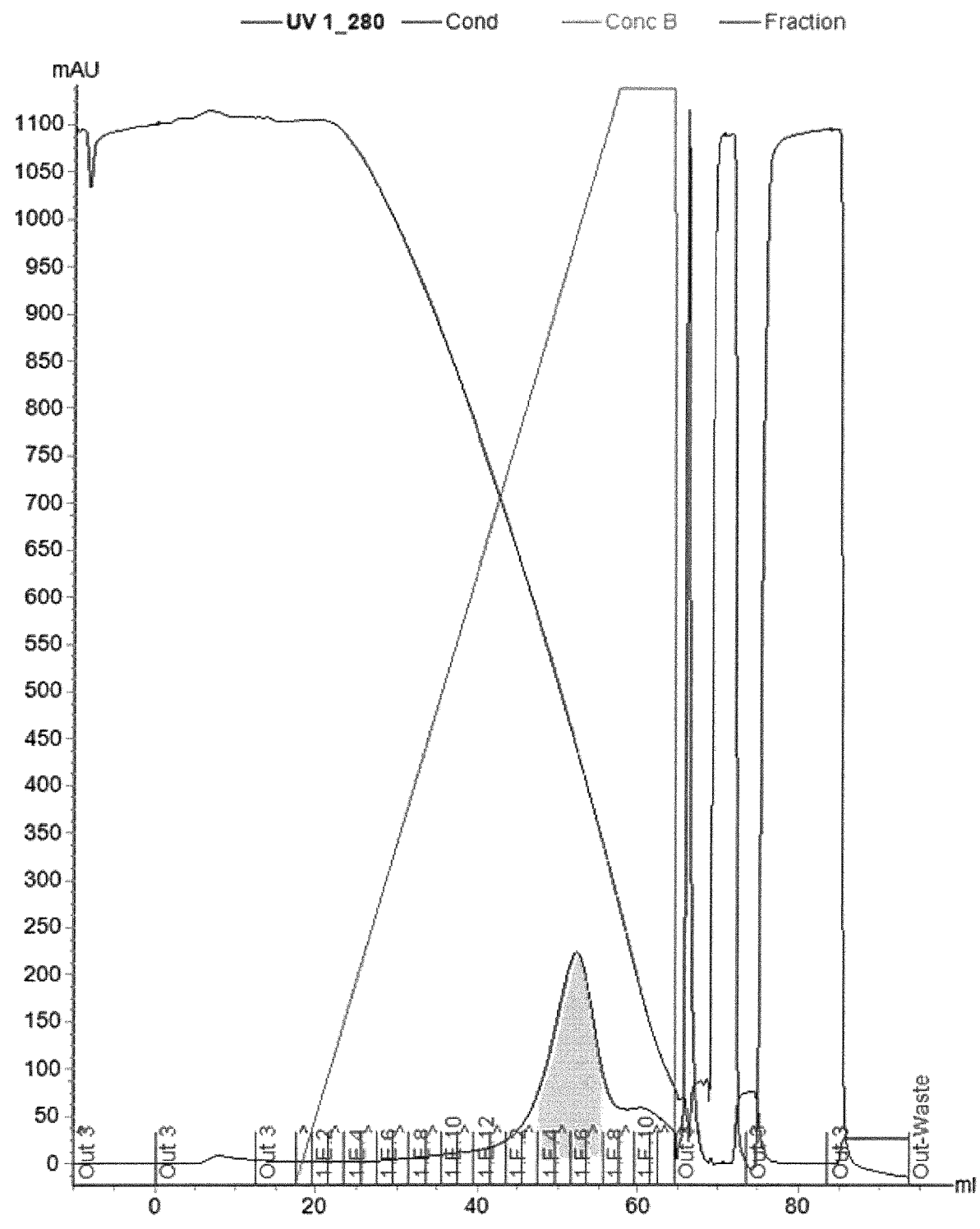

Example 6: Separation of Anti-DR5/Anti-FAP Antibodies from $LC_{DR5}$ Mispaired Variants Thereof Using Butyl Sepharose HP and Toyopearl Butyl 650 C Under the same conditions as in example 5, the separation of anti-DR5/anti-FAP antibodies from $LC_{DR5}$ mispaired variants thereof using Butyl Sepharose HP and Toyopearl Butyl 650 was compared (FIG. 11 A-B). It could be shown that in the total pool volume of the SE-HPLC and the HIC-HPLC of the Butyl Sepharose HP HIC separation, the $LC_{DR5}$ mispaired variants were reduced compared to the starting material while the $LC_{DR5}$ mispaired variants in the total pool volume of the SE-HPLC and the HIC-HPLC of the Toyopearl PPG 600 M HIC separation were only slightly reduced (Table 15).

TABLE 15

SE-HPLC and HIC-HPLC analysis of anti-DR5/anti-FAP antibodies, $LC_{DR5}$ mispaired variants thereof and other product-related byproducts, such as light chain missing variants, in the starting material and in the product pool determined by SEC-MALS and ESI-MS.

| | Yield [%] | Volume [CV] | SE-HPLC [%] |
|---|---|---|---|
| Starting material | n.a. | n.a. | 76.0 |
| Butyl Sepharose HP | 50.2 | 4 | 97.2 |
| Toyo Butyl 650 C | 47.0 | 8 | 93.1 |

| | Hydrophobic interaction HPLC | | |
|---|---|---|---|
| | anti-DR5/anti-FAP bispecific antibodies [%] | $LC_{DR5}$ mispaired antibody variants [%] | product-related byproducts [%] |
| Starting material | 53.9 | 6.8 | 39.3 |
| Butyl Sepharose HP | 94.4 | 0.8 | 4.8 |
| Toyo Butyl 650 C | 84.0 | 5.3 | 10.7 |

Example 7: Separation of Anti-pTau-PS422 Antibodies and $LC_{Tau-PS422}$ Mispaired Variants Thereof Using Butyl Sepharose HP Anti-pTau-PS422 antibodies were expressed and purified from culture supernatant using Protein A affinity chromatography as described above and the solution comprising the anti-pTau-PS422 antibodies and $LC_{Tau-PS422}$ mispaired variants thereof were subjected to Butyl-Sepharose HP HIC medium with a negative ammonium sulfate gradient at pH5.7.

In detail, subsequent to the Protein A affinity purification as described above, protein A eluate comprising the antipTau-PS422 antibodies and LC$_{Tau-PS422}$ mispaired variants thereof were adjusted to 1 M ammonium sulfate in 500 mM sodium acetate at pH 5.7. This solution was subjected to hydrophobic interaction chromatography (CV=1 ml) according to the following procedure:

TABLE 16

Procedure of separating anti-pTau-PS422 antibodies from LC$_{Tau-PS422}$ mispaired variants thereof using Butyl Sepharose HP.

| | | |
|---|---|---|
| Equilibration | | 500 mM sodium acetate, 1M ammonium sulfate, pH 5.7 |
| Elution | 20 CV | linear gradient to 40 mM sodium acetate, pH 5.7 |

Figure 12:
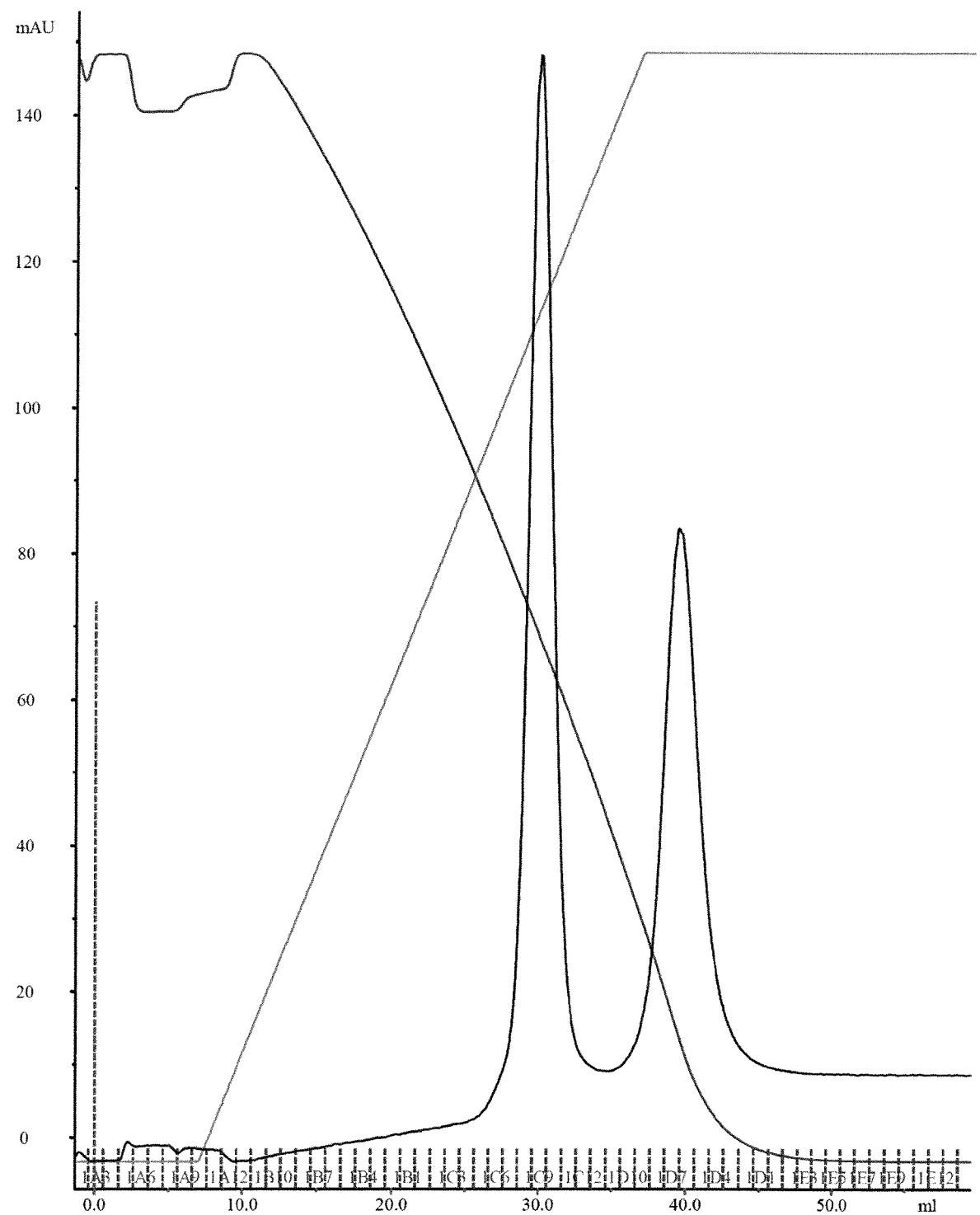
FIG. 12: Chromatogram of a HIC using Butyl Sepharose HP HIC medium with a linear, negative ammonium sulfate gradient sulfate in 500 mM sodium acetate at pH 5.5. Fractions collected for the analysis with SE-HPLC (B) and HI-HPLC (C) are shown on the x-axis.

For analytical assessment, the eluate was fractionated into peak 1 and 2 and characterized by analytical SEC, CE-SDS and MS (FIG. 12).

It could be confirmed by SEC, CE-SDS and MS that peak 1 comprised the anti-pTau-PS422 antibodies and was clearly separated from peak 2 comprising LC$_{Tau-PS422}$ mispaired variants thereof visible by two distinct peaks in the elution profile of the HIC separation (FIG. 12).

Example 8: Separation of Anti-pTau-PS422 Antibodies and LC$_{Tau-PS422}$ Mispaired Variants Thereof Using Capto Butyl ImpRes As in example 7, anti-pTau-PS422 antibodies were expressed and purified from culture supernatant using Protein A affinity chromatography as described above and the solution comprising the anti-pTau-PS422 antibodies and LC$_{Tau-PS422}$ mispaired variants thereof were subjected to Capto Butyl ImpRes HIC medium with a negative ammonium sulfate gradient at pH 5.7.

In detail, subsequent to the Protein A affinity purification as described above, protein A eluate comprising the anti-pTau-PS422 antibodies and LC$_{Tau-PS422}$ mispaired variants thereof were adjusted to 1 M ammonium sulfate in 500 mM sodium acetate at pH 5.5. This solution was subjected to hydrophobic interaction (CV=1 ml) according to the following procedure:

TABLE 17

Procedure of separating anti-pTau-PS422 antibodies from LC$_{Tau-PS422}$ mispaired variants thereof using Capto Butyl ImpRes.

| | | |
|---|---|---|
| Equilibration | | 500 mM sodium acetate, 1M ammonium sulfate, pH 5.5 |
| Elution | 30 CV | linear gradient to 40 mM sodium acetate, pH 5.5 |

The eluate was fractionated, only one peak eluted late in the gradient that was shown to be the intact product comprising the anti-pTau-PS422 antibodies. LC$_{Tau-PS422}$ mispaired variants thereof bound to strong and did not elute from the column under these conditions.

Example 9: Separation of Anti-pTau-PS422 Antibodies and LC$_{Tau-PS422}$ Mispaired Variants Thereof Using Capto Phenyl ImpRes Anti-pTau-PS422 antibodies were expressed and purified as described in Example 1. The solution comprising the anti-pTau-PS422 antibodies and LC$_{Tau-PS422}$ mispaired variants thereof were subjected to Capto Phenyl ImpRes HIC medium with a negative ammonium sulfate gradient at pH5.5.

In detail, subsequent to the Protein A affinity purification as described above, protein A eluate comprising the anti-pTau-PS422 antibodies and LC$_{Tau-PS422}$ mispaired variants thereof was adjusted to 1 M ammonium sulfate in 500 mM sodium acetate at pH 5.5. This solution was subjected to hydrophobic interaction chromatography (8CV=5 ml) according to the following procedure:

TABLE 18

Procedure of separating anti-pTau-PS422 antibodies and LC$_{Tau-PS422}$ mispaired variants thereof using Capto Phenyl ImpRes.

| | | |
|---|---|---|
| Equilibration | | 500 mM sodium acetate, 1M ammonium sulfate, pH 5.5 |
| Elution | 30 CV | linear gradient to 40 mM sodium acetate, pH 5.5 |

The eluate was fractionated, only one peak eluted late in the gradient that was shown to be the intact product comprising the anti-pTau-PS422 antibodies. LC$_{Tau-PS422}$ mispaired variants thereof bound to strong and did not elute from the column under these conditions.

The invention claimed is:

1. A method for separating a multispecific CrossMab antibody from a light chain (LC) mispaired variant thereof by using a hydrophobic interaction chromatography (HIC) medium, the medium comprising a matrix of particles substituted with ligands,
   (i) wherein said particles have an average size of 50 μm or less in diameter and said ligands are butyl groups;
   (ii) wherein said particles have an average size of from 35 μm to 60 μm in diameter and said ligands are phenyl groups; or
   (iii) wherein said particles have an average size of from 35 μm to 100 μm in diameter and said ligands are polypropylene glycol groups,
   wherein the method comprises contacting said multispecific CrossMab antibody and said LC mispaired variant thereof with the HIC medium, and eluting said multispecific CrossMab antibody, thus separating said multispecific CrossMab antibody from said LC mispaired variant thereof.

2. A method for separating a multispecific CrossMab antibody from a light chain (LC) mispaired variant thereof, comprising
   subjecting a solution comprising said CrossMab antibody and said LC mispaired variant thereof to a hydrophobic interaction chromatography (HIC) step, thereby obtaining said CrossMab antibody depleted of said LC mispaired variant thereof,
   wherein the chromatographic medium used in said HIC step comprises a matrix of particles substituted with ligands,
   (i) wherein said particles have an average size of 50 μm or less in diameter and said ligands are butyl groups;
   (ii) wherein said particles have an average size of from 35 μm to 60 μm in diameter and said ligands are phenyl groups; or
   (iii) wherein said particles have an average size of from 35 μm to 100 μm in diameter and said ligands are polypropylene glycol (PPG) groups.

3. The method for separating a multispecific CrossMab antibody according to claim 2, wherein at least one of the Fab regions of said antibody is a Fab region, in which the variable and/or constant domains of the heavy and light chain are exchanged and provided that not the same exchange is made in Fab regions of different binding specificity and provided that the same exchange is made in Fab regions having the same binding specificity.

4. The method according to claim 2, wherein the HIC medium is selected from the group consisting of:
   (i) an HIC medium having an average particle size of about 34 µm, having butyl groups as ligands, having a ligand density of about 50 µmol/ml medium, having a binding capacity of about 39 mg BSA/ml medium, and comprising a matrix of cross-linked agarose;
   (ii) an HIC medium having an average particle size of about 40 µm, having butyl groups as ligands, having a binding capacity of about 37 mg BSA/ml medium, and comprising a matrix of cross-linked agarose;
   (iii) an HIC medium having an average particle size of about 40 µm, having phenyl groups as ligands, having a ligand density of about 9 µmol/ml medium, having a binding capacity of about 19 mg BSA/ml medium, and comprising a matrix of cross-linked agarose; and
   (iv) an HIC medium having an average particle size of about 65 µm, having PPG groups as ligands, and comprising a matrix of cross-linked polymethylmethacrylate.

5. The method according to claim 2, wherein said multispecific CrossMab antibody is a multispecific antibody comprising
   (a) a first antigen binding region specifically binding to a first antigen, wherein the first antigen binding region comprises the light chain and heavy chain of an antibody specifically binding to a first antigen, and
   (b) a second antigen binding region specifically binding to a second antigen, wherein the second antigen binding region comprises the light chain and heavy chain of an antibody specifically binding to a second antigen, wherein in the second antigen binding region
      (i) the constant domains CL and CH1 are replaced by each other, and/or
      (ii) the constant domains VL and VH are replaced by each other.

6. The method according to claim 5, wherein said multispecific antibody is a bispecific bivalent antibody, a bispecific trivalent or a bispecific, tetravalent antibody.

7. The method according to claim 6, wherein the multispecific antibody is bivalent for the first antigen and bivalent for the second antigen.

8. The method according to claim 7, wherein the antibody comprises
   (a) two of said first antigen binding regions; and
   (b) two of said second antigen binding regions,
   wherein each of said second antigen binding regions is fused via a peptide connector either at the C- or N-terminus of the heavy chain of one of said first antigen binding regions.

9. The method according to claim 8, wherein the antibody is an IgG antibody and the heavy chains of said first antigen binding regions comprise CH2 and CH3 domains, and wherein each of said second antigen binding regions is fused via a peptide connector to the C-terminus of the heavy chain of one of said first antigen binding regions.

10. The method according to claim 7, wherein the antibody comprises
    a) two light chains and two heavy chains of an antibody, which specifically binds to a first antigen and comprises two Fab regions;
    b) two additional Fab regions of an antibody which specifically binds to a second antigen, wherein said additional Fab regions are fused both via a peptide connector either at the C- or N-termini of the heavy chains of a); wherein in the Fab regions the following modifications are performed:
       i) in both Fab regions of a), or in both Fab regions of b), the variable domains VL and VH are replaced by each other, and/or the constant domains CL and CH1 are replaced by each other,
       ii) in both Fab regions of a) the variable domains VL and VH are replaced by each other, and the constant domains CL and CH1 are replaced by each other, and in both Fab regions of b) the variable domains VL and VH are replaced by each other, or the constant domains CL and CH1 are replaced by each other,
       iii) in both Fab regions of a) the variable domains VL and VH are replaced by each other, or the constant domains CL and CH1 are replaced by each other, and in both Fab regions of b) the variable domains VL and VH are replaced by each other, and the constant domains CL and CH1 are replaced by each other,
       iv) in both Fab regions of a) the variable domains VL and VH are replaced by each other, and in both Fab regions of b) the constant domains CL and CH1 are replaced by each other, or
       v) in both Fab regions of a) the constant domains CL and CH1 are replaced by each other, and in both Fab regions of b) the variable domains VL and VH are replaced by each other.

11. The method according to claim 2, wherein the multispecific CrossMab antibody and said LC mispaired variant thereof are separately eluted from the HIC medium, thereby separating the multispecific CrossMab antibody from the LC mispaired variant thereof in the solution based on hydrophobicity.

12. The method according to claim 2, wherein the matrix is a polymeric matrix or an agarose-based matrix.

13. The method according to claim 2, wherein the substituted ligands have a concentration of between 9 and 50 µmol per ml HIC medium.

14. The method according to claim 2, wherein the medium used in HIC has a dynamic binding capacity of between 19 and 39 mg of bovine serum albumin per mL medium.

15. The method according to claim 2, wherein said method further comprises one or more further purification step(s) prior and/or after the HIC step.

16. The method according to claim 2, wherein the LC mispaired variant thereof is a variant of said multispecific CrossMab antibody, wherein one or more light chains are paired with a non-complementary heavy chain.

17. The method according to claim 12, wherein the agarose-based matrix comprises between 4 and 6% agarose.

* * * * *